US 7,989,587 B2

(12) United States Patent
Ayyoub et al.

(10) Patent No.: US 7,989,587 B2
(45) Date of Patent: Aug. 2, 2011

(54) SSX-2 PEPTIDES PRESENTED BY HLA CLASS II MOLECULES

(75) Inventors: Maha Ayyoub, New York, NY (US); Danila Valmori, New York, NY (US)

(73) Assignee: Ludwig Institute for Cancer Research Ltd., New York, NY (US)

( * ) Notice: Subject to any disclaimer, the term of this patent is extended or adjusted under 35 U.S.C. 154(b) by 178 days.

(21) Appl. No.: 12/233,964

(22) Filed: Sep. 19, 2008

(65) Prior Publication Data

US 2009/0099063 A1    Apr. 16, 2009

Related U.S. Application Data

(60) Division of application No. 10/937,794, filed on Sep. 9, 2004, now Pat. No. 7,429,639, which is a continuation-in-part of application No. 10/779,568, filed on Feb. 13, 2004, now abandoned, which is a continuation-in-part of application No. 09/408,036, filed on Sep. 29, 1999, now Pat. No. 6,800,730.

(51) Int. Cl.
*A61K 38/00* (2006.01)
*A61K 38/04* (2006.01)
*C07K 5/00* (2006.01)

(52) U.S. Cl. ........ 530/323; 530/326; 530/327; 530/328; 530/332

(58) Field of Classification Search .................. None
See application file for complete search history.

(56) References Cited

U.S. PATENT DOCUMENTS

| | | | |
|---|---|---|---|
| 5,965,535 A | 10/1999 | Chaux et al. | |
| 6,291,658 B1 | 9/2001 | Gure et al. | |
| 6,339,140 B1 | 1/2002 | Gure et al. | |
| 6,548,064 B1 | 4/2003 | Tureci et al. | |
| 6,686,147 B1 * | 2/2004 | Scanlan et al. | 435/6 |
| 2005/0079553 A1 | 4/2005 | Ayyoub et al. | |

FOREIGN PATENT DOCUMENTS

WO    WO 00/20581    4/2000

OTHER PUBLICATIONS

Li Zhu, Huang, and Xiong. Mutational analysis of the binding of staphylococcal enterotoxin D to the T cell receptor Vbeta chain and major histocompatibility complex class II. Immunology Letters, 2006. vol. 105, pp. 55-60.*

Kersh, Miley, Nelson, Grakoui, Horvath, Donermeyer, Kappler, Allen, and Fremont. Structural and functional consequences of altering a peptide MHC anchor residue. Journal of Immunology, 2001. vol. 166, pp. 3345-3354.*

Ayyoub, M. et al., SSX antigens as tumor vaccine targets in human sarcoma. Cancer Immunity 3: 13, 2003.

Ayyoub, M. et al., Tumor-reactive, SSX-2-specific CD8+ T cells are selectively expanded during immune responses to antigen-expressing tumors in melanoma patients. Cancer Res 63: 5601-5606, 2003.

Ayyoub, M. et al., An immunodominant SSX-2-derived epitope recognized by CD4+ T cells in association with HLA-DR. J Clin Invest 113(8): 1225-1233, 2004.

Ayyoub, M. et al., Proteasome-assisted identification of a SSX-2-derived epitope recognized by tumor-reactive CTL infiltrating metastatic melanoma. J Immunol 168(4): 1717-1722, 2002.

Ayyoub, M. et al., Identification of an SSX-2 epitope presented by dendritic cells to circulating autologous CD4+ T cells. J Immunol 172(11): 7206-7211, 2004.

Chaux et al., Identification of MAGE-3 epitopes presented by HLA-DR molecules to CD4(+) T lymphocytes. J Exp Med 189: 767-777, 1999.

Chen, Y.T. et al., A testicular antigen aberrantly expressed in human cancers detected by autologous antibody screening. Proc Natl Acad Sci USA 94(5): 1914-1918, 1997.

Consogno, G. et al., Identification of immunodominant regions among promiscuous HLA-DR-restricted CD4+ T-cell epitopes on the tumor antigen MAGE-3. Blood 101(3): 1038-1044, 2003.

Crew et al., Fusion of SYT to two genes, SSX1 and SSX2, encoding proteins with homology to the Kruppel-associated box in human synovial sarcoma. EMBO J. 14 (10) :2333-2340, 1995.

Dos Santos, N. R., et al., Heterogeneous expression of the SSX cancer/testis antigens in human melanoma lesions and cell lines. Cancer Res., 60:1654-1662, 2000.

Gnjatic, S. et al., Strategy for monitoring T cell responses to NY-ESO-1 in patients with any HLA class I allele. Proc Natl Acad Sci USA 97(20): 10917-10922, 2000.

Gure, A.O. et al., SSX: a multigene family with several members transcribed in normal testis and human cancer. Int J Cancer 72: 965-971, 1997.

Jäger, E. et al., Simultaneous humoral and cellular immune response against cancer-testis antigen NY-ESO-1: definition of human histocompatibility leukocyte antigen (HLA)-A2-binding peptide epitopes. J Exp Med 187(2): 265-270, 1998.

James, R.F. et al., The effect of class II gene transfection on the tumourigenicity of the H-2K-negative mouse leukemia cell line K36. 16. Immunology 72(2): 213-218, 1991.

Kobayashi, H. et al., Defining promiscuous MHC class II helper T-cell epitopes for the HER2/neu tumor antigen. Cancer Res., 60:5228-5236, 2000.

Kubuschok, et al., Gene-modified spontaneous Epstein-Barr virus-transformed lymphoblastoid cell lines as autologous cancer vaccines: mutated p21 ras oncogene as a model. Cancer Gene Ther 7(9): 1231-1240, 2000.

Mischo, et al., Recombinant antigen expression on yeast surface (RAYS) for the detection of serological immune responses in cancer patients. Cancer Immun. 3: 5, 2003.

(Continued)

*Primary Examiner* — Anne M. Gussow
(74) *Attorney, Agent, or Firm* — Wolf, Greenfield & Sacks, P.C.

(57) ABSTRACT

The invention describes HLA class II binding peptides encoded by the SSX-2 tumor associated gene, as well as nucleic acids encoding such peptides and antibodies relating to the peptides. The peptides stimulate the activity and proliferation of CD4+T lymphocytes. Methods and products also are provided for diagnosing and treating conditions characterized by expression of the SSX-2 gene.

8 Claims, 16 Drawing Sheets

OTHER PUBLICATIONS

Mumberg, D. et al., CD4(+) T cells eliminate MHC class II-negative cancer cells in vivo by indirect effects of IFN-gamma. Proc Natl Acad Sci USA 96(15): 8633-8638, 1999.

Old, L.J. Cancer/testis (CT) antigens—a new link between gametogenesis and cancer. Cancer Immunity 1: 1, 2001.

Rammensee et al., SYFPEITHI: database for MHC ligands and peptide motifs. Immunogenetics 41:178-228, 1995.

Stockert, E. et al., A survey of the humoral immune response of cancer patients to a panel of human tumor antigens. J Exp Med 187(8): 1349-1354, 1998.

Surman, S. et al., Localization of CD4+ T cell epitope hotspots to exposed strands of HIV envelope glycoprotein suggests structural influences on antigen processing. Proc Natl Acad Sci USA 98(8): 4587-4592, 2001.

Thurner, B. et al., Vaccination with mage-3A1 peptide-pulsed mature, monocyte-derived dendritic cells expands specific cytotoxic T cells and induces regression of some metastases in advanced stage IV melanoma. J. Exp. Med., 190(11):1669-1678, (1999).

Toes, R.E. et al., CD4T cells and their role in antitumor immune responses. J Exp Med 189(5): 753-756, 1999.

Tureci, O. et al., The SSX-2 gene, which is involved in the t(X;18) translocation of synovial sarcomas, codes for the human tumor antigen HOM-MEL-40. Cancer Res 56(20): 4766-4772, 1996.

Tureci, O. et al., Expression of SSX genes in human tumors. Int J Cancer 77(1): 19-23, 1998.

Tureci, O. et al., Identification of a meiosis-specific protein as a member of the class of cancer/testis antigens. Proc Natl Acad Sci USA 95(9): 5211-5216, 1998.

Valmori, D. et al., Modulation of proteasomal activity required for the generation of a cytotoxic T lymphocyte-defined peptide derived from the tumor antigen MAGE-3. J. Exp. Med., 189(6):895-906, (1999).

Valmori et al., Naturally occurring human lymphocyte antigen-A2 restricted CD8+ T-cell response to the cancer testis antigen NY-ESO-1 in melanoma patients. Cancer Res 60: 4499-4506, 2000.

Valmori et al., Frequent cytolytic T-cell responses to peptide MAGE-A10(254-262) in melanoma. Cancer Res 61: 509-512, 2001.

Zaks, T.Z. et al., Immunization with a peptide epitope (p. 369-377) from HER-2/neu leads to peptide-specific cytotoxic T lymphocytes that fail to recognize HER-2/neu+ tumors. Cancer Res 58(21): 4902-4908, 1998.

Zarour, H.M. et al., NY-ESO-1 encodes DRB1*0401-restricted epitopes recognized by melanoma-reactive CD4+ T cells. Cancer Res 60(17): 4946-4952, 2000.

Zarour, H.M. et al., NY-ESO-1 119-143 is a promiscuous major histocompatibility complex class II T-helper epitope recognized by Th1- and Th2-type tumor-reactive CD4+ T cells. Cancer Res 62(1): 213-218, 2002.

Zeng, G. et al., CD4(+) T cell recognition of MHC class II-restricted epitopes from NY-ESO-1 presented by a prevalent HLA DP4 allele: association with NY-ESO-1 antibody production. Proc Natl Acad Sci USA 98(7): 3964-3969, 2001.

Zeng, G. et al., Identification of CD4+ T cell epitopes from NY-ESO-1 presented by HLA-DR molecules. J Immunol 165(2): 1153-1159, 2000.

Coulie, P.G., et al., A new gene coding for a differentiation antigen recognized by autologous cytolytic T lymphocytes on HLA-A2 melanomas. J. Exp. Med. 180: 35-42, 1994.

Hammer J., et al., Precise prediction of major histocompatibility complex class II-peptide interaction based on peptide side chain scanning J Exp. Med. 180: 2353-2358, 1994.

Hung, K., et al., The Central Role of CD4+ T Cells in the Antitumor Immune Response. J. Exp. Med. 188(12): 2357-2368, 1998.

Kawakami, Y., et al., Identification of the immunodominant peptides of the MART-1 human melanoma antigen recognized by the majority of HLA-A2-restricted tumor infiltrating lymphocytes. J. Exp. Med. 180: 347-352, 1994.

Robbins, P.F., et al., A mutated beta-catenin gene encodes a melanoma-specific antigen recognized by tumor infiltrating lymphocytes. J. Exp. Med. 183: 1185-1192, 1996.

Jäger, E. et al., Induction of primary NY-ESO-1 immunity: CD8+ T lymphocyte and antibody responses in peptide-vaccinated patients with NY-ESO-1+ cancers. Proc. Natl. Acad. Sci. USA. 97: 12198-12203, 2000.

Chen, C.H. et al., Expressions of cancer-testis antigens in human hepatocellular carcinomas. Cancer Lett 164(2): 189-195, 2001.

Clark et al., Identification of novel genes, SYT and SSX, involved in the t(X;18)(p11.2;q11.2) translocation found in human synovial sarcoma. Nat Genet 7: 502-508, 1994.

Falcioni et al., Peptidomimetic compounds that inhibit antigen presentation by autoimmune disease-associated class II major histocompatibility molecules. Nature Biotechnology 17: 562-567, 1999.

Gure, A.O. et al., The SSX gene family: characterization of 9 complete genes. Int J Cancer 101(5): 448-453, 2002.

Klenerman et al., Tracking T cells with tetramers: new tales from new tools. Nat Rev Immunol 2: 263-272, 2002.

Naka et al., Expression of SSX genes in human osteosarcomas. Int J Cancer 98(4): 640-642, 2002.

Qin, Z. et al., CD4+ T cell—mediated tumor rejected involves inhibition of angiogenesis that is dependent on IFN gamma receptor expression by nonhematopoietic cells. Immunity 12(6): 677-686, 2000.

Rubio-Godoy et al., Combinatorial peptide library-based identification of peptide ligands for tumor-reactive cytolytic T lymphocytes of unknown specificity. Eur. J. Immunol 32 (8) : 2292-2299, 2002.

Scanlan, et al., Cancer/testis antigens: an expanding family of targets for cancer immunotherapy Immunol Rev 188: 22-32, 2002.

Sturniolo et al., Generation of tissue-specific and promiscuous HLA ligand databases using DNA microarrays and virtual HLA class II matrices. Nature Biotechnology 17: 555-561, 1999.

Tang, T.F. et al., DRB1 03 diversity and DRB3 associations in five major population groups in the United States. Immunol 63(3): 221-228, 2002.

Wang, R.F. The role of MHC class II-restricted tumor antigens and CD4+ T cells in antitumor immunity. Trends Immunol 22(5): 269-276, 2001.

Alexander, J., et al., Development of high potency universal DR-restricted helper epitopes by modification of high affinity DR-blocking peptides. *Immunity*., 1: 751-761, 1994.

Ayyoub et al., Lack of tumor recognition by hTERT peptide 540-548-specific CD8(+) T cells from melanoma patients reveals inefficient antigen processing. Eur J Immunol 31(9): 2642-2651, 2001.

Hammer et al., Techniques to identify the rules governing class II MHC-peptide interaction, MHC vol. 2 A Practical Approach, Oxford University Press, pp. 197-223, 1998.

Romero, P. et al., CD8+ T-cell response to NY-ESO-1: relative antigenicity and in vitro immunogenicity of natural and analogue sequences. *Clin.Cancer Res*., 7, 766s-772s, 2001.

Burgess et al., Possible dissociation of the heparin-binding and mitogenic activities of heparin-binding (acidic fibroblast) growth factor-1 from its receptor-binding activities by site-directed mutagenesis of a single lysine residue. Journal of Cell Biology, 1990; 111: 2129-2138.

Lazar et al., Transforming growth factor a: mutation of aspartic acid 47 and leucine 48 results in different biological activities. Molecular and Cellular Biology 1998; 8(3):1247-1252.

Schwartz et al., A superactive insulin: [B10-Aspartic acid] insulin (human). Proceedings of the National Academy of Sciences, 1987; 84: 6408-6411.

Lin et al., Structure-functino relationships in glucagon: properties of highly purified Des-His1-, Monoiodo-, and [Des-Asn28,Thr29](homoserine lactone27)-glucagon. Biochemistry 1975; 14(8): 1559-1563.

* cited by examiner

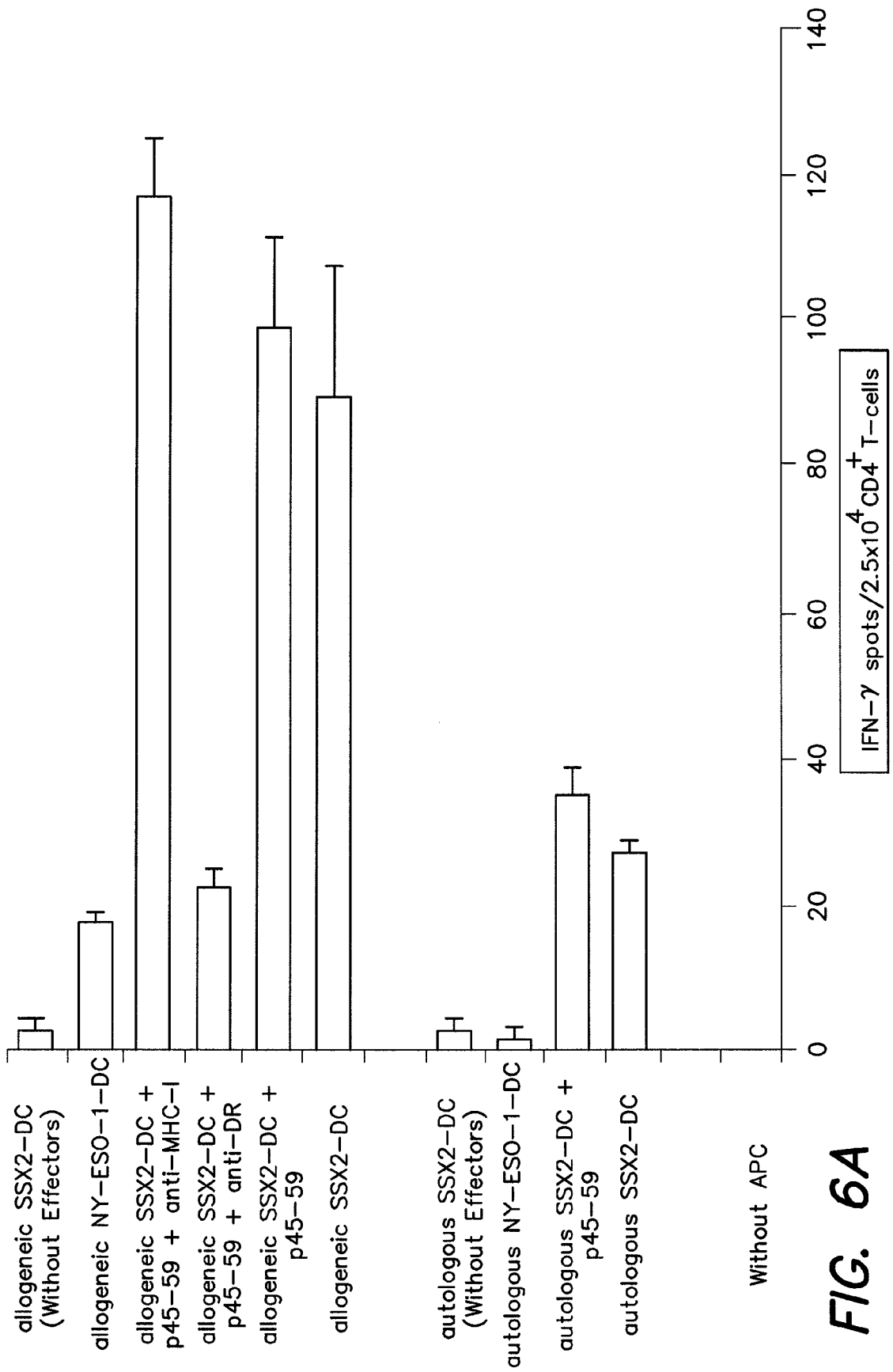

Predicted binding to DRB1* alleles

| DRB1* | Peptide SSX-2 | Sequence | Binding Score | Ranking |
|---|---|---|---|---|
| 1101 | 45-59 | KIFYVYMKRKYEAMT | 24 | 2nd |
| 0301 | 37-51 | WEKMKASEKIFYVYM | 26 | 3rd |
| 0301 | 44-58 | EKIFYVYMKRKYEAM | 23 | 4th |

|        | T331A | T567A | T465A |
|--------|-------|-------|-------|
| SSX-2  | +     | +     | −     |
| HLA-DR3| +     | −     | +     |
| HLA-A2 | −     | +     | +     |
| HLA-DR |       |       |       |
| − IFN-γ | 87   | 117   | 154   |
| + IFN-γ | 167  | 360   | 278   |
| MHC class I |  |       |       |
| − IFN-γ | 129  | 101   | 80    |
| + IFN-γ | 211  | 224   | 151   |

Predicted Binding of SSX 37-51 Homologous Sequences to DRB1* 0301

A

| Peptide 37-51 | Sequence | Binding Score | Ranking |
| --- | --- | --- | --- |
| SSX-2 | WEKMKASEKIFYVYM | 26 | 3rd |
| SSX-1 | WKKMKYSEKISYVYM | 26 | 1st |
| SSX-3 | WEKMKVSEKIVYVYM | 26 | 2nd |
| SSX-4 | WEKMKSSEKIVYVYM | 27 | 2nd |
| SSX-5 | WEKMKASEKIIYVYM | 26 | 1st |

US 7,989,587 B2

SSX-2 PEPTIDES PRESENTED BY HLA CLASS II MOLECULES

RELATED APPLICATIONS

This application is a divisional of U.S. application Ser. No. 10/937,794, filed Sep. 9, 2004, now issued as U.S. Pat. No. 7,429,639, which is a continuation-in-part of U.S. application Ser. No. 10/779,568, filed Feb. 13, 2004, now abandoned, which is a continuation-in-part of U.S. application Ser. No. 09/408,036, filed Sep. 29, 1999, now issued as U.S. Pat. No. 6,800,730, all of which are incorporated by reference herein.

FIELD OF THE INVENTION

This invention relates to fragments of the tumor associated gene product SSX-2 which bind to and are presented to T lymphocytes by HLA class II molecules. The peptides, nucleic acid molecules which code for such peptides, as well as related antibodies and CD4+ T lymphocytes, are useful, inter alia, in diagnostic and therapeutic contexts.

BACKGROUND OF THE INVENTION

The process by which the mammalian immune system recognizes and reacts to foreign or alien materials is complex. An important facet of the system is the T cell response, which in part comprises mature T lymphocytes which are positive for either CD4 or CD8 cell surface proteins. T lymphocytes can recognize and interact with other cells via cell surface complexes of peptides and molecules referred to as human leukocyte antigens ("HLAs") or major histocompatibility complexes ("MHCs"). These peptides are derived from larger molecules which are processed by the cells which also present the HLA/MHC molecule. See Male et al., *Advanced Immunology* (J. P. Lipincott Company, 1987), especially chapters 6-10. The interaction of T cells and complexes of HLA/peptide is restricted, requiring a specific T cell for a specific complex of an HLA molecule and a peptide. If a specific T cell is not present, there is no T cell response even if its partner complex is present. Similarly, there is no response if the specific complex is absent, but the T cell is present. The mechanisms described above are involved in the immune system's response to foreign materials, in autoimmune pathologies, cellular abnormalities, and in responses to cancer.

The ability of the T cell arm of the tumor immune response to distinguish tumor cells from normal tissues with exquisite specificity, provides the basis for the development of T cell based cancer immunotherapy. This specific recognition is the result of the preferential or exclusive expression of some antigens in tumors as compared to normal tissues. Several categories of antigens with more or less tumor-restricted expression have been identified during the last decade. Most of them correspond to non mutated self-antigens with tissue restricted expression, although tumor-specific mutated antigens have also been identified (Robbins et al., *J Exp Med*, 1996, 183:1185-1192). Tissue-specific differentiation antigens such as Melan-A or gp100 (Kawakami et al, *J Exp Med*, 1994, 180:347-352; Coulie, *J Exp Med*, 1994. 180:35-42) expressed by both normal cells of the melanocytic lineage and malignant melanoma cells, and often spontaneously immunogenic in melanoma patients, have been extensively studied. The group of tumor antigens most relevant for the development of generic cancer vaccines, however, is that of the so-called cancer/testis antigens (CTA) (Scanlan et al. *Immunol Rev* 2002. 188:22-32), whose gene expression is developmentally regulated, being mostly restricted to gametogenic cells but silent in adult normal cells. Possibly as the result of activation of a common gametogenic protein expression program in cancer cells (Old et al. *Cancer Immunity* 2001. 1:1). CTA are expressed in variable proportions of tumors of different histological types.

Numerous MHC Class I restricted epitopes recognized by tumor reactive CD8+ T cells and specific for antigens in each of the groups listed above have been identified. Interestingly, spontaneous CD8+ T cell responses directed against several of these epitopes have been detected in cancer patients (Valmori et al, *Cancer Res*, 2000. 60:4499-4506; Valmori et al., *Cancer Res*, 2001, 61:501-512). In contrast, the identification of MHC Class II restricted epitopes recognized by tumor antigen specific CD4+ T cells has proven to be more difficult possibly because of the relatively low frequency of the latter and/or to the lack of effective identification methods (Klenerman et al, *Nat Rev Immunol*, 2002, 2:263-272). Lately, however, because of important technical advances, the identification of CD4+ T cell epitopes derived from tumor antigens including CTA has been reported with increasing frequency (Chaux et al. *J Exp Med* 1999. 189:767-778; Zeng et al. *Proc Natl Acad Sci USA* 2001. 98:3964-3969).

Because most nonhematopoietic tumors express MHC Class I but not Class II molecules, it has been assumed that the predominant antitumor T cell mediated effector mechanism in vivo is direct killing of tumor cells by tumor antigen specific CD8+ T lymphocytes (CTL). CTL can indeed directly and efficiently lyse tumor cells resulting sometimes in in vivo regression of large tumor masses. It is, however, becoming increasingly clear that both tumor antigen specific CD8+ and CD4+ T cell responses are important for efficient tumor immune response to occur in vivo (Wang, *Trends Immunol.* 2001. 22:269-276).

The multiple roles that tumor antigen specific CD4+ T cells can potentially play in mediating antitumor functions are being progressively unveiled. These involve different mechanisms from providing help for both priming and maintenance of tumor antigen specific CD8+ T cells, to activation of B cells for production of tumor antigen specific antibodies, and even including more direct effects in the effector phase of tumor rejection. The identification of CD4+ T cell epitopes toward which spontaneous responses arise in cancer patients is of particular interest as it gives the opportunity to analyze such responses and their underlying molecular mechanisms in vivo. Furthermore, there exist many patients who would not benefit from any therapy which includes helper T cell stimulation via the aforementioned peptides. Accordingly, there is a need for the identification of additional tumor associated antigens which contain epitopes presented by MHC Class II molecules and recognized by CD4+ lymphocytes.

SUMMARY OF THE INVENTION

It now has been discovered that the SSX-2 gene (also known as HOM-MEL-40) encodes HLA class II binding peptides that are epitopes presented by HLA-DR. These peptides, when presented by an antigen presenting cell having the appropriate HLA class II molecule, effectively induce the activation and proliferation of CD4+ T lymphocytes.

The invention provides isolated SSX-2 peptides which bind HLA class II molecules, and functional variants of such peptides. The functional variants contain one or more amino acid additions, substitutions or deletions to the SSX-2 peptide sequence. The invention also provides isolated nucleic acid molecules encoding such peptides, expression vectors containing those nucleic acid molecules, host cells transfected with those nucleic acid molecules, and antibodies to those peptides and complexes of the peptides and HLA class II antigen presenting molecules. T lymphocytes which recognize complexes of the peptides and HLA class II antigen presenting molecules are also provided. Kits and vaccine compositions containing the foregoing molecules additionally are provided. The foregoing can be used in the diagnosis or treatment of conditions characterized by the expression of SSX-2. As it is known that the members of the SSX family of polypeptides and nucleic acids share significant sequence identity and functional homology (e.g., as tumor antigens and precursors), the invention also embraces HLA binding peptides of similar amino acid sequence derived from members of the SSX family other than SSX-2 (see, e.g., Table III and Table IV). Therefore, it is understood that the disclosure contained herein of SSX-2 HLA class II binding peptides, compositions containing such peptides, and methods of identifying and using such peptides applies also to other members of the SSX tumor associated antigen family.

According to one aspect of the invention, isolated SSX-2 HLA class II-binding peptides are provided. The peptides include an amino acid sequence set forth as SEQ ID NO:25, or a functional variant thereof comprising 1-5 amino acid substitutions. The HLA class II-binding peptide or functional variant does not include a full length SSX protein, particularly a full length SSX-2 protein. In certain embodiments, the isolated includes comprises an amino acid sequence selected from the group consisting of SEQ ID NO:10, SEQ ID NO:22, SEQ ID NO:23, SEQ ID NO:24 and SEQ ID NO:42. More preferably the isolated peptide consists of an amino acid sequence selected from the group consisting of SEQ ID NO:10, SEQ ID NO:22, SEQ ID NO:23, SEQ ID NO:24, SEQ ID NO:25 and SEQ ID NO:42, most preferably SEQ ID NO:25 or SEQ ID NO:42. Preferred functional variants include SEQ ID NOs:32-38, as shown in Table IV, and fragments thereof that bind HLA class II molecules.

In further embodiments, the isolated peptide includes an endosomal targeting signal, preferably including an endosomal targeting portion of human invariant chain Ii.

In other embodiments, the isolated peptide is non-hydrolyzable. Preferred non-hydrolyzable peptides include peptides comprising D-amino acids, peptides comprising a -psi[CH$_2$NH]-reduced amide peptide bond, peptides comprising a -psi[COCH$_2$]-ketomethylene peptide bond, peptides comprising a -psi[CH(CN)NH]-(cyanomethylene)amino peptide bond, peptides comprising a -psi[CH$_2$CH(OH)]-hydroxyethylene peptide bond, peptides comprising a -psi[CH$_2$O]-peptide bond, and peptides comprising a -psi[CH$_2$S]-thiomethylene peptide bond.

According to another aspect of the invention, compositions are provided that include an isolated HLA class I-binding peptide and an isolated SSX-2 HLA class II-binding peptide. The isolated SSX-2 HLA class II-binding peptide includes an amino acid sequence set forth as SEQ ID NO:25, or a functional variant thereof comprising 1-5 amino acid substitutions (but not including the full length of a SSX protein, particularly a full length SSX-2 protein). Preferably the HLA class I-binding peptide and the SSX-2 HLA class II-binding peptide are combined as a polytope polypeptide.

In preferred embodiments, the isolated SSX-2 HLA class II-binding peptide includes an amino acid sequence selected from the group consisting of SEQ ID NO:10, SEQ ID NO:22, SEQ ID NO:23, SEQ ID NO:24 and SEQ ID NO:42. More preferably the isolated peptide consists of an amino acid sequence selected from the group consisting of SEQ ID NO:10, SEQ ID NO:22, SEQ ID NO:23, SEQ ID NO:24, SEQ ID NO:25 and SEQ ID NO:42, most preferably SEQ ID NO:25 or SEQ ID NO:42. Preferred functional variants include SEQ ID NOs:32-38, as shown in Table IV, and fragments thereof that bind HLA class II molecules.

In further embodiments, the isolated SSX-2 HLA class II-binding peptide includes an endosomal targeting signal, preferably including an endosomal targeting portion of human invariant chain Ii.

According to a further aspect of the invention, compositions including one or more of the foregoing isolated SSX-2 HLA class II-binding peptides complexed with one or more isolated HLA class II molecules are provided. Preferably the number of isolated SSX-2 HLA class II-binding peptides and the number of isolated HLA class II molecules are equal. More preferably, the isolated SSX-2 HLA class II-binding peptides and the isolated HLA class II molecules are coupled as a tetrameric molecule of individual isolated SSX-2 HLA class II-binding peptides bound to individual isolated HLA class II molecules. Even more preferably, the HLA class II molecules are DR molecules.

According to still another aspect of the invention, isolated nucleic acid molecules are provided that encode the foregoing SSX-2 HLA class II-binding peptides, provided that the nucleic acid molecule does not encode a full length SSX protein, particularly a full length SSX-2 protein. Also provided are expression vectors including these isolated nucleic acid molecules operably linked to a promoter. In certain embodiments, the nucleic acid molecule includes a nucleotide sequence selected from the group consisting of SEQ ID NO:46, SEQ ID NO:47, SEQ ID NO:48, SEQ ID NO:49, SEQ ID NO:50 and SEQ ID NO:51, preferably SEQ ID NO:46 and SEQ ID NO:47. The foregoing expression vectors, in other embodiments, also include a nucleic acid molecule that encodes an HLA-DR molecule. Host cells transfected or transformed with the foregoing expression vectors also are provided; in some embodiments, the host cell expresses an HLA-DR molecule.

In another aspect of the invention, methods for selectively enriching a population of T lymphocytes with CD4$^+$ T lymphocytes specific for a SSX-2 HLA class II-binding peptide are provided. The methods include contacting an isolated population of T lymphocytes with an agent presenting a complex of the SSX-2 HLA class II-binding peptide and an HLA class II molecule in an amount sufficient to selectively enrich the isolated population of T lymphocytes with the CD4$^+$ T lymphocytes.

According to another aspect of the invention, methods for diagnosing a cancer characterized by expression of SSX-2 HLA class II-binding peptide are provided. The methods include contacting a biological sample isolated from a subject with an agent that is specific for the SSX-2 HLA class II-binding peptide, and determining the interaction between the agent and the SSX-2 HLA class II-binding peptide as a determination of the disorder. Preferably the agent is an antibody or an antigen binding fragment thereof.

According to yet another aspect of the invention, methods for diagnosing a cancer characterized by expression of a SSX-2 HLA class II-binding peptide which forms a complex with an HLA class II molecule are provided. The methods include contacting a biological sample isolated from a subject with an agent that binds the complex, and determining binding between the complex and the agent as a determination of the disorder.

In still a further aspect of the invention, methods for treating a subject having a cancer characterized by expression of SSX-2 HLA class II-binding peptide are provided. The methods include administering to the subject an amount of a SSX-2 HLA class II-binding peptide effective to ameliorate the disorder.

According to a further aspect of the invention, additional methods for treating a subject having a cancer characterized by expression of SSX-2 HLA class II-binding peptide are provided. These methods include administering to the subject an amount of a HLA class I-binding peptide and an amount of a SSX-2 HLA class II-binding peptide effective to ameliorate the disorder. In some preferred embodiments, the HLA class I-binding peptide and the SSX-2 HLA class II-binding peptide are combined as a polytope polypeptide. Preferably the HLA class I-binding peptide is a SSX-2 HLA class I-binding peptide.

According to another aspect of the invention, methods for treating a subject having a cancer characterized by expression of SSX-2 are provided. The methods include administering to the subject an amount of a SSX-2 HLA class II-binding peptide effective to ameliorate the cancer.

In another aspect of the invention, methods are provided for treating a subject having a cancer characterized by expression of SSX-2 HLA class II-binding peptide. The methods include administering to the subject an amount of autologous CD4$^+$ T lymphocytes sufficient to ameliorate the disorder, wherein the CD4$^+$ T lymphocytes are specific for complexes of an HLA class II molecule and a SSX-2 HLA class II-binding peptide.

In the foregoing methods, the SSX-2 HLA class II-binding peptide preferably includes an amino acid sequence set forth as SEQ ID NO:25, or a functional variant thereof comprising 1-5 amino acid substitutions. In certain preferred embodiments of the foregoing methods, the SSX-2 HLA class II-binding peptide includes an amino acid sequence selected from the group consisting of SEQ ID NO:10, SEQ ID NO:22, SEQ ID NO:23, SEQ ID NO:24 and SEQ ID NO:42. More preferably the isolated peptide consists of an amino acid sequence selected from the group consisting of SEQ ID NO:10, SEQ ID NO:22, SEQ ID NO:23, SEQ ID NO:24, SEQ ID NO:25 and SEQ ID NO:42, most preferably SEQ ID NO:25 or SEQ ID NO:42. Preferred functional variants include SEQ ID NOs:32-38, as shown in Table IV, and fragments thereof that bind HLA class II molecules. In some embodiments, the HLA class II molecule is an HLA-DR molecule. In other embodiments, the SSX-2 HLA class II binding peptide includes an endosomal targeting signal, preferably an endosomal targeting portion of human invariant chain Ii.

In a further aspect of the invention, methods for identifying functional variants of a SSX-2 HLA class II-binding peptide are provided. The methods include selecting a SSX-2 HLA class II-binding peptide which includes an amino acid sequence selected from the group consisting of SEQ ID NO:10, SEQ ID NO:22, SEQ ID NO:23, SEQ ID NO:24, SEQ ID NO:25 and SEQ ID NO:42, an HLA class II-binding molecule which binds the SSX-2 HLA class II-binding peptide, and a T cell which is stimulated by the SSX-2 HLA class II-binding peptide presented by the HLA class II-binding molecule; mutating a first amino acid residue of the SSX-2 HLA class II-binding peptide to prepare a variant peptide; and determining the binding of the variant peptide to HLA class II-binding molecule and the stimulation of the T cell. Binding of the variant peptide to the HLA class II-binding molecule and stimulation of the T cell by the variant peptide presented by the HLA class II-binding molecule indicates that the variant peptide is a functional variant. Exemplary functional variants that can be tested using such methods and used as controls in such methods include the preferred functional variants (SEQ ID NOs:32-38, and fragments thereof that bind HLA class II molecules).

In some embodiments, the methods include a step of comparing the stimulation of the T cell by the SSX-2 HLA class II-binding peptide and the stimulation of the T cell by the functional variant as a determination of the effectiveness of the stimulation of the T cell by the functional variant.

According to another aspect of the invention, isolated polypeptides are provided that bind selectively the foregoing SSX-2 HLA class II-binding peptides, provided that the isolated polypeptide is not an HLA class II molecule. Also provided are isolated polypeptides that bind selectively a complex of the foregoing SSX-2 HLA class II-binding peptides and an HLA class II molecule, provided that the isolated polypeptide is not a T cell receptor. The foregoing isolated polypeptides preferably are antibodies, more preferably monoclonal antibodies. Preferred monoclonal antibodies include human antibodies, humanized antibodies, chimeric antibodies and single chain antibodies. In other embodiments, the isolated polypeptides are antibody fragments selected from the group consisting of Fab fragments, F(ab)$_2$ fragments, Fv fragments or fragments including a CDR3 region selective for a SSX-2 HLA class II-binding peptide.

The invention also provides isolated CD4$^+$ T lymphocytes that selectively bind a complex of an HLA class II molecule and a SSX-2 HLA class II-binding peptide, preferably wherein the HLA class II molecule is an HLA-DR molecule and wherein the SSX-2 HLA class II-binding peptide includes an amino acid sequence set forth as SEQ ID NO:25 or a functional variant thereof. More preferably, the SSX-2 HLA class II-binding peptide includes an amino acid sequence selected from the group consisting of SEQ ID NO:10, SEQ ID NO:22, SEQ ID NO:23, SEQ ID NO:24 and SEQ ID NO:42. Still more preferably the isolated peptide consists of an amino acid sequence selected from the group consisting of SEQ ID NO:10, SEQ ID NO:22, SEQ ID NO:23, SEQ ID NO:24, SEQ ID NO:25 and SEQ ID NO:42, most preferably SEQ ID NO:25 or SEQ ID NO:42. Preferred functional variants include SEQ ID NOs:32-38, as shown in Table IV, and fragments thereof that bind HLA class II molecules.

In a further aspect, the invention provides isolated antigen presenting cells that include a complex of an HLA class II molecule and a SSX-2 HLA class II-binding peptide, preferably wherein the HLA class II molecule is an HLA-DR molecule and wherein the SSX-2 HLA class II-binding peptide comprises an amino acid sequence set forth as SEQ ID NO:25 or a functional variant thereof. More preferably, the SSX-2 HLA class II-binding peptide includes an amino acid sequence selected from the group consisting of SEQ ID NO:10, SEQ ID NO:22, SEQ ID NO:23, SEQ ID NO:24 and SEQ ID NO:42. Still more preferably the isolated peptide consists of an amino acid sequence selected from the group consisting of SEQ ID NO:10, SEQ ID NO:22, SEQ ID NO:23, SEQ ID NO:24, SEQ ID NO:25 and SEQ ID NO:42, most preferably SEQ ID NO:25 or SEQ ID NO:42. Preferred functional variants include SEQ ID NOs:32-38, as shown in Table IV, and fragments thereof that bind HLA class II molecules.

According to another aspect of the invention, methods for identification of HLA class II-binding epitopes of a protein are provided. The methods include obtaining a peptide library of peptides that span the amino acid sequence of the protein; and contacting a population of cells containing CD4$^+$ T lymphocytes with the peptide library in the presence of antigen presenting cells to stimulate proliferation and/or cytokine production by CD4+ T lymphocytes that selectively bind a peptide in the peptide library. The stimulation of CD4+ T lymphocytes indicates that a peptide in the library contains at least one HLA class II epitope. In certain embodiments, the peptides are at least about 12 amino acids in length. In other embodiments, the peptides are between about 14 and about 50 amino acids in length. Preferably the peptides are between about 20 and about 22 amino acids in length.

In other embodiments, the peptides overlap each other by at least about 4 amino acids, more preferably by at least about 10 amino acids.

In still other embodiments, the antigen presenting cells are autologous peripheral blood mononuclear cells.

The method can include additional steps of screening the isolated CD4+ T lymphocytes with submixtures or single peptides, and/or clonally expanding the stimulated CD4+ T lymphocytes by periodic stimulation with the selected peptide and/or isolating the stimulated CD4+ T lymphocytes. In the last case, it is preferred that the isolation of the stimulated CD4+ T lymphocytes is carried out by cytokine guided flow cytometry cell sorting.

In some embodiments, the population of cells containing CD4+ T lymphocytes also includes CD8+ T lymphocytes. In these embodiments, the stimulation of both CD4+ and CD8+ T lymphocytes indicates that a peptide in the synthetic library contains both HLA class I and HLA class II epitopes.

The invention further include the products and methods described above, which include or use SSX-2 peptides p98-112 and p101-115 (SEQ ID NO:40 and SEQ ID NO:43, respectively).

The invention also provides pharmaceutical preparations containing any one or more of the medicaments described above or throughout the specification. Such pharmaceutical preparations can include pharmaceutically acceptable diluents, carriers and/or excipients.

The use of the foregoing compositions, peptides, cells and nucleic acids in the preparation of a medicament, particularly a medicament for treatment of cancer, or for treating an immune response is also provided.

The compositions and methods described herein could also include or be performed using peptides SEQ ID NO:81 and SEQ ID NO:82. It is preferred in these methods that the HLA molecules are DRB1*0101 and DRB1*1501, respectively.

These and other objects of the invention will be described in further detail in connection with the detailed description of the invention.

BRIEF DESCRIPTION OF THE DRAWINGS

As shown in FIG. 1, the presence of specific CD4+ T cells in the culture from patient LAU 672 was assessed by intracellular staining with anti-IFN-γ after stimulation with autologous PBMC alone ("no peptide"), with a mixture of all peptides ("all peptides") or with the peptide submixtures P1-3 (containing SSX-2 peptides 1-22, 13-34, 25-46) or P4-6 (containing SSX-2 peptides 37-58, 49-70, 61-82). FIG. 1A shows FACS analysis of stimulated cells. Numbers in upper right quadrants are percent of cytokine producing cells among CD4+ T cells. The data obtained for all peptide submixtures (P1-3, P4-6, P7-9, P10-12 and P13-15) is shown in FIG. 1B.

In FIG. 2A, cells were treated with no peptide, a mixture of all peptides, or the individual peptides as shown. In FIG. 2B, cells were treated with a mixture of all peptides and with antibodies to HLA-DR, HLA-DP or HLA-DQ as shown.

FIG. 5A: Demonstration of the HLA-DR restriction. In contrast to the anti-DP-clone B7/21, both the anti-pan DR clone L243 and anti-pan MHC-II clone WR18 inhibit the reaction of p45-59 primed effector T-cells from donor Col7 with p45-59 pulsed autologous PBMC. Treatment of these APC with anti-pan MHC-I antibody (clone W6/32) did not influence the T-cell response excluding an MHC-I mediated CD8+ T-cell response and, hence, a cross-reactivity of p45-59 with the partially overlapping MHC-I restricted p41-49. FIG. 5B: Dissection of the HLA-DR restriction against p45-59. The reactivity of T-cells from donor Col7 with allogeneic LCL 40, that were used as APC in this ELISPOT assay and share only the HLA-DRB1*0701 subtype with the responding T-cells, demonstrate that the reaction against p45-59 in this experiment is mediated by HLA-DRB1*0701.

FIG. 6 shows natural processing of the HOM-MEL-40/SSX-2 derived epitope p45-59 by dendritic cells and tumor cells. FIG. 6A: Following exogenous administration of the whole-protein antigen, autologous as well as allogeneic DC both induced T-cells from healthy donor Col7 prestimulated with p45-59 to secrete IFN-γ, while the control protein (NY-ESO-1) remained unrecognized. The T-cell response against the naturally processed epitope p45-59 was blocked by anti-pan-MHC-II and anti-DR antibodies, respectively.

SSX-2 specific CD4+ T cells were isolated by cytokine secretion guided cell sorting. (B) Peptide recognition by an SSX-2 37-58 specific CD4+ T cell clone was assessed either in the absence or in the presence of anti HLA-DR or -DP mAbs. (C) The ability of molecularly typed APC to present peptide SSX-2 37-58 to specific CD4+ T cells was assessed by intracellular IFN-g secretion. Numbers in upper right quadrants are percent of cytokine producing cells among CD4+ T cells.

FIG. 8 shows determination of the minimal sequence optimally recognized by SSX-2 specific DR3 restricted CD4+ T cells. (A) Binding score and ranking of SSX-2 peptides (SEQ ID NOs:42, 52 and 53) to the indicated HLA class II alleles were calculated using the SYFPEITHI binding prediction program. (B and C) Synthetic peptides truncated at the N- or C-terminus of the SSX-2 37-58 sequence were used to determine the optimal length of the epitope recognized by SSX-2 specific DR3 restricted CD4+ T cells. Peptide activity of truncated peptides was assessed in peptide titration experiments (B). Peptide activity was calculated relative to that of SSX-2 37-58 (C) (SEQ ID NOs:10, 22, 23, 24, 25, 26, 27, 28, 29, 30, 31, 54 and 55).

FIG. 9 shows assessment of recognition of native SSX-2 antigen by 37-51 specific DR3 restricted CD4+ T cells. (A) Recognition of tumor cell lines T331A, T465A and T567A by SSX-2 specific CD4+ T cells was assessed by ELISA measurement of IFN-γ secretion in the culture supernatant in the absence or in the presence of exogenously added peptide (P). Where indicated, cells were treated with IFN-g (200 IU/ml) during 48 h. Recognition was similarly assessed using a CD8+ T cell clone specific for the previously described HLA-A2 restricted CD8+ T cell epitope SSX-2 41-49. (B) Characteristics of the tumor cell lines used to assess recognition of endogenous SSX-2 antigen and effect of IFN-g treatment on their MHC class I and HLA-DR surface expression. HLA-DR expression was assessed by staining with L243 mAb. MHC class I expression was assessed by staining with W6/32 mAb. Where indicated, IFN-γ (200 U/ml) was added to the culture medium during 48 hrs prior to analysis. Values correspond to mean fluorescence intensity (MFI). Staining with isotype matched control mAbs resulted in a MFI of 4-6. Staining of an EBV cell line as internal control gave a MFI of 271 for W6/32 and 787 for L243. (C) Processing and presentation of SSX-2 antigen by EBV cells after incubation with soluble recombinant SSX-2 protein. NY-ESO-1 protein was used as negative control.

Figure 10:
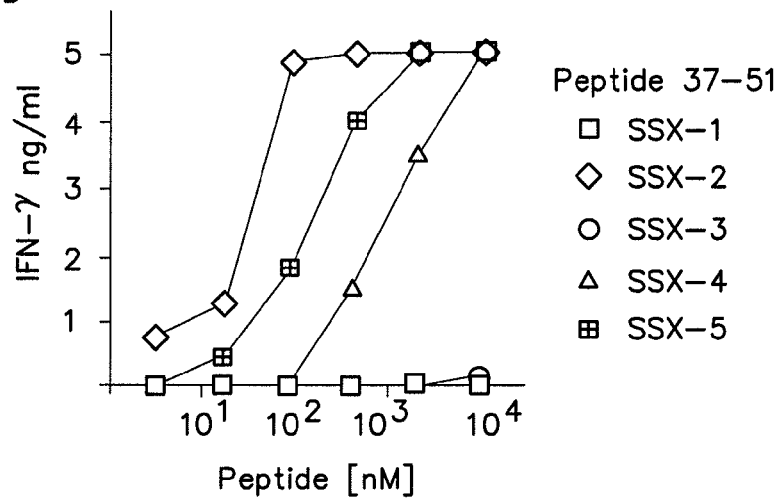
Figure 10:
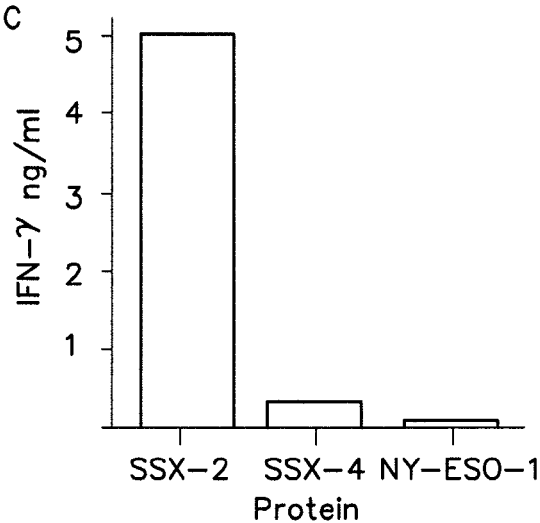

FIG. 10 shows assessment of cross-recognition of homologous sequences from other SSX antigens. (A) Binding score and ranking of SSX 37-51 homologous peptides (SEQ ID NOs:52, 83, 84, 85 and 86) was calculated using the SYFPEITHI binding prediction program (refer to the Institute for Cell Biology, Department of Immunology website for a database of MHC ligands and peptide motifs). (B) Cross-recognition of 37-51 homologous peptides by SSX-2 specific CD4+ T cells was assessed in peptide titration experiments by ELISA measurement of IFN-γ secretion in the culture supernatant. (C) Cross-recognition of SSX-4 recombinant protein was similarly assessed after overnight incubation of CD4+ T cells with protein loaded EBV cells.

BRIEF DESCRIPTION OF THE SEQUENCES

SEQ ID NOs:1 and 2 are the nucleotide and amino acid sequences, respectively, for SSX-2 polypeptide isoform b/transcript variant 2 (nucleic acid=NM_175698.1, GI:28559005; polypeptide=NP_783629.1 GI:28559006).

SEQ ID NOs:3 and 4 are the nucleotide and amino acid sequences, respectively, for SSX-2 polypeptide isoform a/transcript variant 1 (nucleic acid=NM_003147.4, GI:28559004; polypeptide=NP_003138.3 GI:27659724).

SEQ ID NOs:5 and 6 are nucleotide and amino acid sequences, respectively, for a protein that is similar to SSX-2 isoform b/transcript variant 2 (nucleic acid=XM_300501.1, GI:30157775; polypeptide=XP_300501.1, GI:30157776).

SEQ ID NO: 7 is a $SSX-2_{1-22}$ peptide (MNGDDAFARRPTVGAQIPEKIQ).

SEQ ID NO: 8 is a $SSX-2_{13-34}$ peptide (VGAQIPEKIQKAFDDIAKYFSK).

SEQ ID NO: 9 is a $SSX-2_{25-46}$ peptide (FDDIAKYFSKEEWEKMKASEKI).

SEQ ID NO: 10 is a $SSX-2_{37-58}$ peptide (WEKMKASEKIFYVYMKRKYEAM).

SEQ ID NO: 11 is a $SSX-2_{49-70}$ peptide (VYMKRKYEAMTKLGFKATLPPF).

SEQ ID NO: 12 is a $SSX-2_{61-82}$ peptide (LGFKATLPPFMCNKRAEDFQGN).

SEQ ID NO: 13 is a $SSX-2_{73-94}$ peptide (NKRAEDFQGNDLDNDPNRGNQV).

SEQ ID NO: 14 is a $SSX-2_{87-105}$ peptide (DPNRGNQVERPQMTFGRLQ).

SEQ ID NO: 15 is a $SSX-2_{97-118}$ peptide (PQMTFGRLQGISPKIMPKKPAE).

SEQ ID NO: 16 is a $SSX-2_{109-130}$ peptide (PKIMPKKPAEEGNDSEEVPEAS).

SEQ ID NO: 17 is a $SSX-2_{121-142}$ peptide (NDSEEVPEASGPQNDGKELCPP).

SEQ ID NO: 18 is a $SSX-2_{133-154}$ peptide (QNDGKELCPPGKPTTSEKIHER).

SEQ ID NO: 19 is a $SSX-2_{145-166}$ peptide (PTTSEKIHERSGPKRGEHAWTH).

SEQ ID NO: 20 is a $SSX-2_{157-178}$ peptide (PKRGEHAWTHRLRERKQLVIYE).

SEQ ID NO: 21 is a $SSX-2_{169-188}$ peptide (RERKQLVIYEEISDPEEDDE).

SEQ ID NO: 22 is a $SSX-2_{39-58}$ peptide (KMKASEKIFYVYMKRKYEAM).

SEQ ID NO: 23 is a $SSX-2_{41-58}$ peptide (KASEKIFYVYMKRKYEAM).

SEQ ID NO: 24 is a $SSX-2_{43-58}$ peptide (SEKIFYVYMKRKYEAM).

SEQ ID NO: 25 is a $SSX-2_{45-58}$ peptide (KIFYVYMKRKYEAM).

SEQ ID NO: 26 is a $SSX-2_{47-58}$ peptide (FYVYMKRKYEAM).

SEQ ID NO: 27 is a $SSX-2_{49-58}$ peptide (VYMKRKYEAM).

SEQ ID NO: 28 is a $SSX-2_{37-56}$ peptide (WEKMKASEKIFYVYMKRKYE).

SEQ ID NO: 29 is a $SSX-2_{37-54}$ peptide (WEKMKASEKIFYVYMKRK).

SEQ ID NO: 30 is a $SSX-2_{37-52}$ peptide (WEKMKASEKIFYVYMK).

SEQ ID NO: 31 is a SSX-2$_{37-50}$ peptide
(WEKMKASEKIFYVY).

SEQ ID NO: 32 is a peptide corresponding to
SSX-5 isoform b amino acids 45-58,
SSX-5 isoform a amino acids 86-99, and
SSX-9 amino acids 45-58
(KIIYVYMKRKYEAM).

SEQ ID NO: 33 is a SSX-7$_{45-58}$ peptide
(KISYVYMKRKYEAM).

SEQ ID NO: 34 is a SSX-3$_{45-58}$ peptide
(KIVYVYMKRKYEAM).

SEQ ID NO: 35 is a SSX-8$_{45-58}$ peptide
(KISYVYMKRNYEAM).

SEQ ID NO: 36 is a SSX-1$_{45-58}$ peptide
(KISYVYMKRNYKAM).

SEQ ID NO: 37 is a SSX-6$_{45-58}$ peptide
(KISCVHMKRKYEAM).

SEQ ID NO: 38 is a SSX-4$_{45-58}$ peptide
(KIVYVYMKLNYEVM).

SEQ ID NO: 39 is a SSX-2$_{60-74}$ peptide
(KLGFKATLPPFMCNK).

SEQ ID NO: 40 is a SSX-2$_{98-112}$ peptide
(QMTFGRLQGISPKIM).

SEQ ID NO: 41 is a SSX-2$_{171-185}$ peptide
(RKQLVIYEEISDPEE).

SEQ ID NO: 42 is a SSX-2$_{45-59}$ peptide
(KIFYVYMKRKYEAMT).

SEQ ID NO: 43 is a SSX-2$_{101-115}$ peptide
(FGRLQGISPKIMPKK).

SEQ ID NO: 44 is a control peptide
(YAFRASAKA) that binds to different HLA-DR
molecules.

SEQ ID NO: 45 is a test peptide
(PLKMLNIPSINVHHY, amino acids 117-131) from the
pp65 antigen of human CMV.

SEQ ID NO: 46 is a nucleotide sequence
(aaa atc ttc tat gtg tat atg aag aga aag tat gag
gct atg) coding for SEQ ID NO: 25.

SEQ ID NO: 47 is a nucleotide sequence
(aaa atc ttc tat gtg tat atg aag aga aag tat gag
gct atg act) coding for SEQ ID NO: 42.

SEQ ID NO: 48 is a nucleotide sequence
(tgg gaa aag atg aaa gcc tcg gag aaa atc ttc tat
gtg tat atg aag aga aag tat gag gct atg) coding
for SEQ ID NO: 10.

SEQ ID NO: 49 is a nucleotide sequence
(aag atg aaa gcc tcg gag aaa atc ttc tat gtg tat
atg aag aga aag tat gag gct atg) coding for
SEQ ID NO: 22.

SEQ ID NO: 50 is a nucleotide sequence
(aaa gcc tcg gag aaa atc ttc tat gtg tat atg aag
aga aag tat gag gct atg) coding for SEQ ID NO: 23.

SEQ ID NO: 51 is a nucleotide sequence
(tcg gag aaa atc ttc tat gtg tat atg aag aga aag
tat gag gct atg) coding for SEQ ID NO: 24.

SEQ ID NO: 52 is a SSX-2$_{37-51}$ peptide
(WEKMKASEKIFYVYM).

SEQ ID NO: 53 is a SSX-2$_{44-58}$ peptide
(EKIFYVYMKRKYEAM).

SEQ ID NO: 54 is a SSX-2$_{37-48}$ peptide
(WEKMKASEKIFY).

SEQ ID NO: 55 is a SSX-2$_{37-46}$ peptide
(WEKMKASEKI).

SEQ ID NO: 56 is a SSX-2$_{37-57}$ peptide
(WEKMKASEKIFYVYMKRKYEA).

SEQ ID NO: 57 is a SSX-2$_{37-55}$ peptide
(WEKMKASEKIFYVYMKRKY).

SEQ ID NO: 58 is a SSX-2$_{37-53}$ peptide
(WEKMKASEKIFYVYMKR).

SEQ ID NO: 59 is a SSX-2$_{37-51}$ peptide
(WEKMKASEKIFYVYM).

SEQ ID NO: 60 is a SSX-2$_{37-49}$ peptide
(WEKMKASEKIFYV).

SEQ ID NO: 61 is a SSX-2$_{38-57}$ peptide
(EKMKASEKIFYVYMKRKYEA).

SEQ ID NO: 62 is a SSX-2$_{38-55}$ peptide
(EKMKASEKIFYVYMKRKY).

SEQ ID NO: 63 is a SSX-2$_{38-53}$ peptide
(EKMKASEKIFYVYMKR).

SEQ ID NO: 64 is a SSX-2$_{38-51}$ peptide
(EKMKASEKIFYVYM).

SEQ ID NO: 65 is a SSX-2$_{38-49}$ peptide
(EKMKASEKIFYV).

SEQ ID NO: 66 is a SSX-2$_{39-57}$ peptide
(KMKASEKIFYVYMKRKYEA).

SEQ ID NO: 67 is a SSX-2$_{39-55}$ peptide
(KMKASEKIFYVYMKRKY).

SEQ ID NO: 68 is a SSX-2$_{39-53}$ peptide
(EKMKASEKIFYVYMKR).

SEQ ID NO: 69 is a SSX-2$_{39-51}$ peptide
(EKMKASEKIFYVYM).

SEQ ID NO: 70 is a SSX-2$_{39-49}$ peptide
(KMKASEKIFYV).

SEQ ID NO: 71 is a SSX-2$_{38-56}$ peptide
(EKMKASEKIFYVYMKRKYE).

SEQ ID NO: 72 is a SSX-2$_{38-54}$ peptide
(EKMKASEKIFYVYMKRK).

SEQ ID NO: 73 is a SSX-2$_{38-52}$ peptide
(EKMKASEKIFYVYMK).

SEQ ID NO: 74 is a SSX-2$_{38-50}$ peptide
(EKMKASEKIFYVY).

SEQ ID NO: 75 is a SSX-2$_{38-48}$ peptide
(EKMKASEKIFY).

SEQ ID NO: 76 is a SSX-2$_{39-56}$ peptide
(KMKASEKIFYVYMKRKYE).

SEQ ID NO: 77 is a SSX-2$_{39-54}$ peptide
(KMKASEKIFYVYMKRK).

SEQ ID NO: 78 is a SSX-2$_{39-52}$ peptide
(EKMKASEKIFYVYMK).

SEQ ID NO: 79 is a SSX-2$_{39-50}$ peptide
(EKMKASEKIFYVY).

SEQ ID NO: 80 is a SSX-2$_{39-48}$ peptide
(KMKASEKIFY).

-continued

SEQ ID NO: 81 is a SSX-2$_{34-48}$ peptide
(KEEWEKMKASEKIFY).

SEQ ID NO: 82 is a SSX-2$_{49-63}$ peptide
(VYMKRKYEAMTKLGF).

SEQ ID NO: 83 is a SSX-1$_{37-51}$ peptide
(WKKMKYSEKISYVYM).

SEQ ID NO: 84 is a SSX-3$_{37-51}$ peptide
(WEKMKVSEKIVYVYM).

SEQ ID NO: 85 is a SSX-4$_{37-51}$ peptide
(WEKMKSSEKIYYVYM).

SEQ ID NO: 86 is a SSX-5$_{37-51}$ peptide
(WEKMKASEKIFIVYM).

DETAILED DESCRIPTION OF THE INVENTION

The invention provides isolated SSX-2 peptides presented by HLA class II molecules, which peptides stimulate the proliferation and activation of CD4$^+$ T lymphocytes. Such peptides are referred to herein as "SSX-2 HLA class II binding peptides," "HLA class II binding peptides" and "MHC class II binding peptides." Hence, one aspect of the invention is an isolated peptide which includes the amino acid sequence of SEQ ID NO:25, preferably any one of SEQ ID NOs:10, 22, 23, 24, 28, 29, 30, 31, 42, 52, 53, 54 and 55. Likewise SEQ ID NO:81 and SEQ ID NO:82 could be used in a similar manner. The peptides referred to herein as "SSX-2 HLA class II binding peptides" include fragments of SSX-2 protein, but do not include full-length SSX-2 protein (e.g., SEQ ID NOs:2, 4 or 6). Likewise, nucleic acids that encode the "SSX-2 HLA class II binding peptides" include fragments of the SSX-2 gene coding region, but do not include the full-length SSX-2 coding region (e.g., as found in SEQ ID NOs:1, 2 or 3).

The examples below show the isolation of peptides which are SSX-2 HLA class II binding peptides. These exemplary peptides are processed translation products of an SSX-2 nucleic acid (e.g., SEQ ID NOs:1, 2 and 3; the encoded polypeptide sequences are given as SEQ ID NOs:2, 4 and 6). As such, it will be appreciated by one of ordinary skill in the art that the translation products from which a SSX-2 HLA class II binding peptide is processed to a final form for presentation may be of any length or sequence so long as they encompass the SSX-2 HLA class II binding peptide. As demonstrated in the examples below, peptides or proteins as small as 14 amino acids and as large as the amino acid sequence of a SSX-2 protein (SEQ ID NOs:2, 4 and 6) are appropriately processed, presented by HLA class II molecules and effective in stimulating CD4$^+$ T lymphocytes. SSX-2 HLA class II binding peptides, such as the peptides of SEQ ID NO:10, SEQ ID NO:22, SEQ ID NO:23, SEQ ID NO:24, SEQ ID NO:25 SEQ ID NO:28, SEQ ID NO:29, SEQ ID NO:30, SEQ ID NO:31, SEQ ID NO:42, SEQ ID NO:52, SEQ ID NO:53, SEQ ID NO:54 and SEQ ID NO:55 may have one, two, three, four, five, six, seven, eight, nine, ten, 15, 20, 25, 30, 40, 50 or more amino acids added to either or both ends. Likewise SEQ ID NO:81 and SEQ ID NO:82 could be used in a similar manner. The antigenic portion of such a peptide is cleaved out under physiological conditions for presentation by HLA class II molecules. It is also well known in the art that HLA class II peptide length is variable between about 10 amino acids and about 30 amino acids (Engelhard, *Ann. Rev. Immunol.* 12:181-201, 1994). Most of the HLA class II binding peptides fall in to the length range of 12-19 amino acids. Nested sets of HLA class II binding peptides have been identified, wherein the peptides share a core sequence but have different amino acids at amino and/or carboxyl terminal ends (see, e.g., Chicz et al., *J. Exp. Med.* 178:27-47, 1993). Thus additional SSX-2 HLA class II binding peptides comprising at least a portion of the sequences of the peptides reported herein, preferably comprising SEQ ID NO:25, as well as homologous SSX family HLA class II binding peptides (e.g., of similar sequence from other SSX proteins such as SSX-1, SSX-3 and SSX-4), can be identified by one of ordinary skill in the art according to the procedures described herein.

The procedures described in the Examples that were utilized to identify SSX-2 HLA class II binding peptides also can be utilized to identify other HLA class II binding peptides, including homologous SSX family HLA class II binding peptides. Thus, for example, one can load antigen presenting cells, such as dendritic cells of normal blood donors, with a recombinant SSX protein (or a number of overlapping peptide fragments thereof as is described herein) by contacting the cells with the SSX polypeptide (or a series of peptides) or by introducing into the cells a nucleic acid molecule which directs the expression of the SSX protein (or peptide) of interest. The antigen-presenting cells then can be used to induce in vitro the activation and/or proliferation of specific CD4 lymphocytes that recognize SSX HLA class II binding peptides. The CD4 lymphocytes can be isolated according to standard methods, including cytokine guided flow cytometry cell sorting as described herein.

The sequence of the peptide epitope then can be determined as described in the Examples, e.g., by stimulating cells with peptide fragments of the SSX protein used to stimulate the activation and/or proliferation of CD4 lymphocytes. If a peptide library is used in the initial screening, then subsets of these peptides or individual peptides can be used for the subsequent screening. Preferably the peptides are at least about 12 amino acids in length for efficient binding to HLA class II molecules. More preferably, the peptides are between about 14 and about 50 amino acids in length, still more preferably between about 20 and about 22 amino acids in length. By using overlapping peptides, all possible epitopes can be screened. In some embodiments, the peptides overlap each other by at least about 4 amino acids, but preferably the peptides overlap each other by at least about 10 amino acids.

In addition, one can make predictions of peptide sequences derived from SSX family proteins which are candidate HLA class II binding peptides based on the consensus amino acid sequences for binding HLA class II molecules. Peptides which are thus selected can be used in the assays described herein for inducing activation and/or proliferation of specific CD4 lymphocytes and identification of peptides. Additional methods of selecting and testing peptides for HLA class II binding are well known in the art. The foregoing methods also can be used to simultaneously screen a protein sequence for the presence of both HLA class I and HLA class II epitopes by contacting the antigen presenting cells with a population of cells that contains both CD4$^+$ T lymphocytes and CD8$^+$ T lymphocytes. The stimulation of both CD4$^+$ and CD8$^+$ T lymphocytes indicates that a peptide in the synthetic library contains both HLA class I and HLA class II epitopes. Stimulation of CD8$^+$ or CD4$^+$ T lymphocytes indicates that only HLA class I or HLA class II epitopes exist in a reactive peptide.

As noted above, the invention embraces functional variants of SSX-2 HLA class II binding peptides. As used herein, a "functional variant" or "variant" of a HLA class II binding peptide is a peptide which contains one or more modifications to the primary amino acid sequence of a HLA class II binding peptide and retains the HLA class II and T cell receptor binding properties disclosed herein. Modifications which create a SSX-2 HLA class II binding peptide functional variant can be made for example 1) to enhance a property of a SSX-2 HLA class II binding peptide, such as peptide stability in an expression system or the stability of protein-protein binding such as HLA-peptide binding; 2) to provide a novel activity or property to a SSX-2 HLA class II binding peptide, such as addition of an antigenic epitope or addition of a detectable moiety; or 3) to provide a different amino acid sequence that produces the same or similar T cell stimulatory properties. Modifications to SSX-2 (as well as SSX family) HLA class II binding peptides can be made to nucleic acids which encode the peptide, and can include deletions, point mutations, truncations, amino acid substitutions and additions of amino acids. Alternatively, modifications can be made directly to the polypeptide, such as by cleavage, addition of a linker molecule, addition of a detectable moiety, such as biotin, addition of a fatty acid, substitution of one amino acid for another and the like.

Preferably the substitutions are not made at anchor residues of a MHC binding epitope. For example, for HLA-DRB1*0301, the anchor residues are at relative position 1 (L, I, F, M, or V), relative position 4 (D), relative position 6 (K, R, E, Q, or N), and relative position 9 (Y, L, or F) (Rammensee, H-G. et al., 1995, Immunogenetics, 41:178-228; Steven, G. E., et al., The HLA Facts Book, Academic Press, 2000). Anchor residues of other MHC binding epitopes are well known in the art; see for example, the website of the European Bioinformatics Institute, Immunogenetics database.

Variants also can be selected from libraries of peptides, which can be random peptides or peptides based on the sequence of the SSX peptides including substitutions at one or more positions (preferably 1-5). For example, a peptide library can be used in competition assays with complexes of SSX peptides bound to HLA class II molecules (e.g. dendritic cells loaded with SSX peptide). Peptides which compete for binding of the SSX peptide to the HLA class II molecule can be sequenced and used in other assays (e.g. CD4 lymphocyte proliferation) to determine suitability as SSX peptide functional variants. Preferred functional variants include SEQ ID NOs:32-38 (related to SEQ ID NO:25-containing peptides) as shown in Table IV, and fragments thereof that bind HLA class II molecules.

Modifications also embrace fusion proteins comprising all or part of a SSX HLA class II binding peptide amino acid sequence, such as the invariant chain-SSX-2 fusion proteins described herein. The invention thus embraces fusion proteins comprising SSX-2 HLA class II binding peptides and endosomal targeting signals such as the human invariant chain (Ii). As is disclosed below, fusion of an endosomal targeting portion of the human invariant chain to SSX-2 resulted in efficient targeting of SSX-2 to the HLA class II peptide presentation pathway. An "endosomal targeting portion" of the human invariant chain or other targeting polypeptide is that portion of the molecule which, when fused or conjugated to a second polypeptide, increases endosomal localization of the second polypeptide. Thus endosomal targeting portions can include the entire sequence or only a small portion of a targeting polypeptide such as human invariant chain Ii. One of ordinary skill in the art can readily determine an endosomal targeting portion of a targeting molecule.

Prior investigations (PCT/US99/21230) noted that fusion of an endosomal targeting portion of LAMP-1 protein did not significantly increase targeting of MAGE-A3 to the HLA class II peptide presentation pathway. It is possible that this was a MAGE-A3 specific effect. Therefore, the SSX-2 peptides of the invention can be tested as fusions with LAMP-1 to determine if such fusion proteins are efficiently targeted to the HLA class II peptide presentation pathway. Additional endosomal targeting signals can be identified by one of ordinary skill in the art, fused to SSX-2 or a SSX-2 HLA class II binding portion thereof, and tested for targeting to the HLA class II peptide presentation pathway using no more than routine experimentation.

The amino acid sequence of SSX HLA class II binding peptides may be of natural or non-natural origin, that is, they may comprise a natural SSX HLA class II binding peptide molecule or may comprise a modified sequence as long as the amino acid sequence retains the ability to stimulate helper T cells when presented and retains the property of binding to an HLA class II molecule such as an HLA DR molecule. For example, SSX-2 HLA class II binding peptides in this context may be fusion proteins including a SSX-2 HLA class II binding peptide and unrelated amino acid sequences, synthetic SSX-2 HLA class II binding peptides, labeled peptides, peptides isolated from patients with a SSX-2 expressing cancer, peptides isolated from cultured cells which express SSX-2, peptides coupled to nonpeptide molecules (for example in certain drug delivery systems) and other molecules which include the amino acid sequence of SEQ ID NOs: 10, 22-25, 28, 29, 30, 31, 42, 52, 53, 54 and 55. Likewise SEQ ID NO: 81 and 82 could be used in the same manner.

Preferably, the SSX-2 HLA class II binding peptides are non-hydrolyzable. To provide such peptides, one may select SSX-2 HLA class II binding peptides from a library of non-hydrolyzable peptides, such as peptides containing one or more D-amino acids or peptides containing one or more non-hydrolyzable peptide bonds linking amino acids. Alternatively, one can select peptides which are optimal for inducing $CD4^+$ T lymphocytes and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of a SSX-2 HLA class II binding peptide with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include, but are not limited to, -psi[$CH_2NH$]— reduced amide peptide bonds, -psi[$COCH_2$]-ketomethylene peptide bonds, -psi[CH(CN)NH]-(cyanomethylene)amino peptide bonds, -psi[$CH_2CH(OH)$]-hydroxyethylene peptide bonds, -psi[$CH_2O$]-peptide bonds, and -psi[$CH_2S$]-thiomethylene peptide bonds.

Nonpeptide analogs of peptides, e.g., those which provide a stabilized structure or lessened biodegradation, are also contemplated. Peptide mimetic analogs can be prepared based on a selected SSX-2 HLA class II binding peptide by replacement of one or more residues by nonpeptide moieties. Preferably, the nonpeptide moieties permit the peptide to retain its natural conformation, or stabilize a preferred, e.g., bioactive, confirmation. Such peptides can be tested in molecular or cell-based binding assays to assess the effect of the substitution(s) on conformation and/or activity. One example of methods for preparation of nonpeptide mimetic analogs from peptides is described in Nachman et al., *Regul. Pept.* 57:359-370 (1995). Peptide as used herein embraces all of the foregoing.

If a variant involves a change to an amino acid of SEQ ID NOs: 10, 22-25 28, 29, 30, 31, 42, 52, 53, 54 and 55 functional variants of the SSX-2 HLA class II binding peptide having conservative amino acid substitutions typically will be preferred, i.e., substitutions which retain a property of the original amino acid such as charge, hydrophobicity, conformation, etc. Likewise SEQ ID NO:81 and SEQ ID NO:82 could be used in a similar manner. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Other methods for identifying functional variants of the SSX-2 HLA class II binding peptides are provided in a published PCT application of Strominger and Wucherpfennig (PCT/US96/03182). These methods rely upon the development of amino acid sequence motifs to which potential epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For example, a motif might specify that the residue at a first position may be any one of the residues valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; and that the residue at the fifth position must be lysine.

Other computational methods for selecting amino acid substitutions, such as iterative computer structural modeling, can also be performed by one of ordinary skill in the art to prepare variants. Sequence motifs for SSX-2 HLA class II binding peptide functional variants can be developed by analysis of the binding domains or binding pockets of major histocompatibility complex HLA-DR proteins and/or the T cell receptor ("TCR") contact points of the SSX-2 HLA class II binding peptides disclosed herein. By providing a detailed structural analysis of the residues involved in forming the HLA class II binding pockets, one is enabled to make predictions of sequence motifs for binding of SSX peptides to any of the HLA class II proteins.

Using these sequence motifs as search, evaluation, or design criteria, one is enabled to identify classes of peptides (e.g. SSX HLA class II binding peptides, particularly the SSX-2 peptides disclosed herein, and functional variants thereof) which have a reasonable likelihood of binding to a particular HLA molecule and of interacting with a T cell receptor to induce T cell response. These peptides can be synthesized and tested for activity as described herein. Use of these motifs, as opposed to pure sequence homology (which excludes many peptides which are antigenically similar but quite distinct in sequence) or sequence homology with unlimited "conservative" substitutions (which admits many peptides which differ at critical highly conserved sites), represents a method by which one of ordinary skill in the art can evaluate peptides for potential application in the treatment of disease.

The Strominger and Wucherpfennig PCT application, and references cited therein, all of which are incorporated by reference, describe the HLA class II and TCR binding pockets which contact residues of an HLA class II peptide. By keeping the residues which are likely to bind in the HLA class II and/or TCR binding pockets constant or permitting only specified substitutions, functional variants of SSX HLA class II binding peptides can be prepared which retain binding to HLA class II and T cell receptor.

Thus methods for identifying additional SSX family HLA class II peptides, in particular SSX-2 HLA class II binding peptides, and functional variants thereof, are provided. In general, any SSX protein can be subjected to the analysis noted above, peptide sequences selected and the tested as described herein. With respect to SSX-2, for example, the methods include selecting a SSX-2 HLA class II binding peptide, an HLA class II binding molecule which binds the SSX-2 HLA class II binding peptide, and a T cell which is stimulated by the SSX-2 HLA class II binding peptide presented by the HLA class II binding molecule. In preferred embodiments, the SSX-2 HLA class II binding peptide comprises the amino acid sequence of SEQ ID NOs: 10, 22-25 28, 29, 30, 31, 42, 52, 53, 54 and 55. More preferably, the peptide consists essentially of or consists of the amino acid sequences of SEQ ID NOs: 10, 22-25 28, 29, 30, 31, 42, 52, 53, 54 and 55. Likewise SEQ ID NO:81 and SEQ ID NO:82 could be used in a similar manner. The first amino acid residue of the SSX-2 HLA class II binding peptide is mutated to prepare a variant peptide. The amino acid residue can be mutated according to the principles of HLA and T cell receptor contact points set forth in the Strominger and Wucherpfennig PCT application described above. Any method for preparing variant peptides can be employed, such as synthesis of the variant peptide, recombinantly producing the variant peptide using a mutated nucleic acid molecule, and the like.

The binding of the variant peptide to HLA class II binding molecules and stimulation of the T cell are then determined according to standard procedures. For example, as exemplified below, the variant peptide can be contacted with an antigen presenting cell which contains the HLA class II molecule which binds the SSX-2 peptide to form a complex of the variant peptide and antigen presenting cell. This complex can then be contacted with a T cell which recognizes the SSX-2 HLA class II binding peptide presented by the HLA class II binding molecule. T cells can be obtained from a patient having a condition characterized by expression of SSX-2, such as cancer. Recognition of variant peptides by the T cells can be determined by measuring an indicator of T cell stimulation such as cytokine production (e.g., TNF or IFN-γ) or proliferation of the T cells. Similar procedures can be carried out for identification and characterization of other SSX family HLA class II binding peptides.

Binding of a variant peptide to the HLA class II binding molecule and stimulation of the T cell by the variant peptide presented by the HLA class II binding molecule indicates that the variant peptide is a functional variant. The methods also can include the step of comparing the stimulation of the T cell by the SSX-2 HLA class II binding peptide and the stimulation of the T cell by the functional variant as a determination of the effectiveness of the stimulation of the T cell by the functional variant. By comparing the functional variant with the SSX-2 HLA class II binding peptide, peptides with increased T cell stimulatory properties can be prepared.

The foregoing methods can be repeated sequentially with a second, third, fourth, fifth, sixth, seventh, eighth, ninth, and tenth substitutions to prepare additional functional variants of the disclosed SSX-2 HLA class II binding peptides.

Variants of the SSX-2 HLA class II binding peptides prepared by any of the foregoing methods can be sequenced, if necessary, to determine the amino acid sequence and thus deduce the nucleotide sequence which encodes such variants.

Also a part of the invention are those nucleic acid sequences which code for a SSX HLA class II binding peptides or variants thereof and other nucleic acid sequences which hybridize to a nucleic acid molecule consisting of the above described nucleotide sequences, under high stringency conditions. Preferred nucleic acid molecules include those comprising the nucleotide sequences that encode SEQ ID NOs: 10, 22-25 and 42, which are SEQ ID NOs:48-51, 46 and 47, respectively, and SEQ ID NOs:28, 29, 30, 31, 52, 53, 54 and 55. Likewise SEQ ID NO:81 and SEQ ID NO:82 could be used in a similar manner. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, high stringency conditions, as used herein, refers to hybridization at 65° C. in hybridization buffer (3.5×SSC, 0.02% Ficoll, 0.02% Polyvinyl pyrolidone, 0.02% Bovine Serum Albumin, 25 mM $NaH_2PO_4$ (pH7), 0.5% SDS, 2 mM EDTA). SSC is 0.15M Sodium Chloride/ 0.015M Sodium Citrate, pH 7; SDS is Sodium Dodecyl Sulphate; and EDTA is Ethylene diaminetetraacetic acid. After hybridization, the membrane upon which the DNA is transferred is washed at 2×SSC at room temperature and then at 0.1-0.5×SSC/0.1×SDS at temperatures up to 68° C., e.g., 55° C., 60° C., 65° C. or 68° C. Alternatively, high stringency hybridization may be performed using a commercially available hybridization buffer, such as ExpressHyb™ buffer (Clontech) using hybridization and washing conditions described by the manufacturer.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids encoding the SSX HLA class II binding peptides of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 75% nucleotide identity and/or at least 90% amino acid identity to the nucleic acids that encode a SSX-2 HLA class II binding peptide (such as SEQ ID NOs:10, 22-25, 28, 29, 30, 31, 42, 52, 53, 54 and 55) or to the amino acid sequence of such a peptide, respectively. Likewise SEQ ID NO:81 and SEQ ID NO:82 could be used in a similar manner. In some instances homologs and alleles will share at least 90% nucleotide identity and/or at least 95% amino acid identity, in other embodiments homologs and alleles will share at least 95% nucleotide identity and/or at least 98% amino acid identity, in further embodiments homologs and alleles will share at least 97% nucleotide identity and/or at least 99% amino acid identity and in still other instances will share at least 99% nucleotide identity and/or at least 99.5% amino acid identity. Complements of the foregoing nucleic acids also are embraced by the invention.

In screening for nucleic acids which encode a SSX HLA class II binding peptide, a nucleic acid hybridization such as a Southern blot or a Northern blot may be performed using the foregoing conditions, together with a detectably labeled probe (e.g., radioactive such as $^{32}P$, chemiluminescent, fluorescent labels). After washing the membrane to which DNA encoding a SSX HLA class II binding peptide was finally transferred, the membrane can be placed against X-ray film, phosphorimager or other detection device to detect the detectable label.

The invention also includes the use of nucleic acid sequences which include alternative codons that encode the same amino acid residues of the SSX HLA class II binding peptides. For example, as disclosed herein, the peptide WEK-MKASEKIFYVYMKRKYEAM (SEQ ID NO:10) is a SSX-2 HLA class II binding peptide. The lysine residues (amino acids No. 3, 5, 9, 16 and 18 of SEQ ID NO:10) can be encoded by the codons AAA, and AAG. Each of the two codons is equivalent for the purposes of encoding a lysine residue. Thus, it will be apparent to one of ordinary skill in the art that any of the lysine-encoding nucleotide triplets may be employed to direct the protein synthesis apparatus, in vitro or in vivo, to incorporate a lysine residue. Similarly, nucleotide sequence triplets which encode other amino acid residues comprising the SSX-2 HLA class II binding peptide of SEQ ID NO:10 include: GUA, GUC, GUG and GUU (valine codons); GAA and GAG (glutamine codons); UUC and UUU (phenylalanine codons) and UAC and UAU (tyrosine codons). Other amino acid residues may be encoded similarly by multiple nucleotide sequences. Thus, the invention embraces degenerate nucleic acids that differ from the native SSX HLA class II binding peptide encoding nucleic acids in codon sequence due to the degeneracy of the genetic code.

It will also be understood that the invention embraces the use of the sequences in expression vectors, as well as to transfect host cells and cell lines, be these prokaryotic (e.g., *E. coli*), or eukaryotic (e.g., dendritic cells, CHO cells, COS cells, yeast expression systems and recombinant baculovirus expression in insect cells). The expression vectors require that the pertinent sequence, i.e., those described supra, be operably linked to a promoter. As it has been found that human HLA-DR molecules present a SSX-2 HLA class II binding peptide, the expression vector may also include a nucleic acid sequence coding for a HLA-DR molecule. In a situation where the vector contains both coding sequences, it can be used to transfect a cell which does not normally express either one. The SSX-2 HLA class II binding peptide coding sequence may be used alone, when, e.g. the host cell already expresses a HLA-DR molecule, as appropriate for the peptide. Of course, there is no limit on the particular host cell which can be used as the vectors which contain the two coding sequences may be used in host cells which do not express HLA-DR molecules if desired, and the nucleic acid coding for the SSX-2 HLA class II binding peptide can be used in antigen presenting cells which express a HLA-DR molecule.

As described herein, SSX-2 HLA class II binding peptides bind to HLA class II molecules, preferably HLA-DR molecules. As used herein, "an HLA-DR molecule" includes, but is not limited to, the preferred subtypes DRB1*0101, *0301, *0701, *1101, *1302 and *1501, DRB3*0202 and *0301, and DRB5*0101, including: DRB1*010101, DRB1*010102, DRB1*030101, DRB1*030102, DRB1*070101, DRB1*070102, DRB1*110101, DRB1*110102, DRB1*110103, DRB1*110104, DRB1*110105, DRB1*130201, DRB1*130202, DRB1*150101, DRB1*150102, DRB1*150103, DRB1*150104, DRB1*150105, DRB3*020201, DRB3*020202, DRB3*020203, DRB3*020204, DRB3*030101, DRB3*030102, DRB5*010101, DRB5*010102, and other subtypes known to one of ordinary skill in the art. Other subtypes, including those related to DRB1*0101, *0301, *0701, *1101, *1302 and *1501, DRB3*0202 and *0301, and DRB5*0101 can be found in various publications and internet resources that update HLA allele lists.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate autonomously or after integration into the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

Preferably the expression vectors contain sequences which target a SSX family polypeptide, e.g. SSX-2, or a HLA class II binding peptide derived therefrom, to the endosomes of a cell in which the protein or peptide is expressed. HLA class II molecules contain an invariant chain (Ii) which impedes binding of other molecules to the HLA class II molecules. This invariant chain is cleaved in endosomes, thereby permitting binding of peptides by HLA class II molecules. Therefore in a preferred embodiment, the SSX-2 HLA class II binding peptides and precursors thereof (e.g. the SSX-2 protein) are targeted to the endosome, thereby enhancing the binding of SSX-2 HLA class II binding peptide to HLA class II molecules. Targeting signals for directing molecules to endosomes are known in the art and these signals conveniently can be incorporated in expression vectors such that fusion proteins which contain the endosomal targeting signal are produced. Sanderson et al. (*Proc. Nat'l. Acad. Sci. USA* 92:7217-7221, 1995), Wu et al. (*Proc. Nat'l. Acad. Sci. USA* 92:11671-11675, 1995) and Thomson et al (*J. Virol.* 72:2246-2252, 1998) describe endosomal targeting signals (including invariant chain Ii and lysosomal-associated membrane protein LAMP-1) and their use in directing antigens to endosomal and/or lysosomal cellular compartments.

Endosomal targeting signals such as invariant chain also can be conjugated to SSX-2 protein or peptides by non-peptide bonds (i.e. not fusion proteins) to prepare a conjugate capable of specifically targeting SSX-2. Specific examples of covalent bonds include those wherein bifunctional cross-linker molecules are used. The cross-linker molecules may be homobifunctional or heterobifunctional, depending upon the nature of the molecules to be conjugated. Homobifunctional cross-linkers have two identical reactive groups. Heterobifunctional cross-linkers are defined as having two different reactive groups that allow for sequential conjugation reaction. Various types of commercially available cross-linkers are reactive with one or more of the following groups; primary amines, secondary amines, sulfhydryls, carboxyls, carbonyls and carbohydrates. One of ordinary skill in the art will be able to ascertain without undue experimentation the preferred molecule for linking the endosomal targeting moiety and SSX-2 peptide or protein, based on the chemical properties of the molecules being linked and the preferred characteristics of the bond or bonds.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a SSX-2 HLA class II binding peptide. That heterologous DNA (RNA) is placed under operable control of transcriptional elements to permit the expression of the heterologous DNA in the host cell. As described herein, such expression constructs optionally also contain nucleotide sequences which encode endosomal targeting signals, preferably human invariant chain or a targeting fragment thereof.

Preferred systems for mRNA expression in mammalian cells are those such as pRc/CMV and pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extra-chromosomal element. Another expression vector is the pEF-B OS plasmid containing the promoter of polypeptide Elongation Factor 1a, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710-4716, 1996). Still another preferred expression vector is an adenovirus, described by Stratford-Perricaudet, which is defective for E1 and E3 proteins (*J. Clin. Invest.* 90:626-630, 1992). The use of the adenovirus as an Adeno.P1A recombinant is disclosed by Warnier et al., in intradermal injection in mice for immunization against P1A (*Int. J. Cancer,* 67:303-310, 1996). Recombinant vectors including viruses selected from the group consisting of adenoviruses, adeno-associated viruses, poxviruses including vaccinia viruses and attenuated poxviruses such as ALVAC, NYVAC, Semliki Forest virus, Venezuelan equine encephalitis virus, retroviruses, Sindbis virus, Ty virus-like particle, other alphaviruses, VSV, plasmids (e.g. "naked" DNA), bacteria (e.g. the bacterium Bacille Calmette Guerin, attenuated *Salmonella*), and the like can be used in such delivery, for example, for use as a vaccine.

The invention also embraces so-called expression kits, which allow the artisan to prepare a desired expression vector or vectors. Such expression kits include at least separate portions of at least two of the previously discussed materials. Other components may be added, as desired.

The invention as described herein has a number of uses, some of which are described herein. The following uses are described for SSX-2 HLA class II binding peptides but are equally applicable to use of other SSX family HLA class II binding peptides that are described herein. First, the invention permits the artisan to diagnose a disorder characterized by expression of a SSX-2 HLA class II binding peptide. These methods involve determining expression or presence in a biological sample of a SSX-2 HLA class II binding peptide, or a complex of a SSX-2 HLA class II binding peptide and an HLA class II molecule. The expression of a peptide or complex of peptide and HLA class II molecule can be determined by assaying with a binding partner for the peptide or complex, such as an antibody, a T lymphocyte, a multimeric complex of T cell receptors specific for the complex, and the like. Assays that are well known in the immunological arts can be employed, such as ELISA, ELISPOT, flow cytometry, and the like.

The invention further includes nucleic acid or protein microarrays with components that bind SSX-2 HLA class II peptides or nucleic acids encoding such polypeptides. In this aspect of the invention, standard techniques of microarray technology are utilized to assess expression of the SSX-2 polypeptides and/or identify biological constituents that bind such polypeptides. The constituents of biological samples include antibodies, lymphocytes (particularly T lymphocytes), T cell receptor molecules and the like. Protein microarray technology, which is also known by other names including: protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," *Science* 289(5485): 1760-1763, 2000. Nucleic acid arrays, particularly arrays that bind SSX-2 peptides also can be used for diagnostic applications, such as for identifying subjects that have a condition characterized by SSX-2 polypeptide expression.

Microarray substrates include but are not limited to glass, silica, aluminosilicates, borosilicates, metal oxides such as alumina and nickel oxide, various clays, nitrocellulose, or nylon. The microarray substrates may be coated with a compound to enhance synthesis of a probe (peptide or nucleic acid) on the substrate. Coupling agents or groups on the substrate can be used to covalently link the first nucleotide or amino acid to the substrate. A variety of coupling agents or groups are known to those of skill in the art. Peptide or nucleic acid probes thus can be synthesized directly on the substrate in a predetermined grid. Alternatively, peptide or nucleic acid probes can be spotted on the substrate, and in such cases the substrate may be coated with a compound to enhance binding of the probe to the substrate. In these embodiments, presynthesized probes are applied to the substrate in a precise, predetermined volume and grid pattern, preferably utilizing a computer-controlled robot to apply probe to the substrate in a contact-printing manner or in a non-contact manner such as ink jet or piezo-electric delivery. Probes may be covalently linked to the substrate.

Targets are peptides or proteins and may be natural or synthetic. The tissue may be obtained from a subject or may be grown in culture (e.g. from a cell line).

In some embodiments of the invention one or more control peptide or protein molecules are attached to the substrate. Preferably, control peptide or protein molecules allow determination of factors such as peptide or protein quality and binding characteristics, reagent quality and effectiveness, binding success, and analysis thresholds and success.

Nucleic acid microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast*, Nature Genetics, Vol. 21, January 1999, the entire contents of which is incorporated by reference herein.

According to the present invention, nucleic acid microarray substrates may include but are not limited to glass, silica, aluminosilicates, borosilicates, metal oxides such as alumina and nickel oxide, various clays, nitrocellulose, or nylon. In all embodiments a glass substrate is preferred. According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length may be determined by one of ordinary skill in the art by following art-known procedures. In one embodiment, preferred probes are sets of two or more molecule that bind the nucleic acid molecules that encode the SSX-2 HLA class II binding peptides set forth herein. Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or olignucleotide to the substrate. These agents or groups may include, for example, amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, probes are synthesized directly on the substrate in a predetermined grid pattern using methods such as light-directed chemical synthesis, photochemical deprotection, or delivery of nucleotide precursors to the substrate and subsequent probe production.

In another embodiment, the substrate may be coated with a compound to enhance binding of the probe to the substrate. Such compounds include, but are not limited to: polylysine, amino silanes, amino-reactive silanes (Chipping Forecast, 1999) or chromium. In this embodiment, presynthesized probes are applied to the substrate in a precise, predetermined volume and grid pattern, utilizing a computer-controlled robot to apply probe to the substrate in a contact-printing manner or in a non-contact manner such as ink jet or piezoelectric delivery. Probes may be covalently linked to the substrate with methods that include, but are not limited to, UV-irradiation. In another embodiment probes are linked to the substrate with heat.

Targets for microarrays are nucleic acids selected from the group, including but not limited to: DNA, genomic DNA, cDNA, RNA, mRNA and may be natural or synthetic. In all embodiments, nucleic acid target molecules from human tissue are preferred. The tissue may be obtained from a subject or may be grown in culture (e.g. from a cell line).

In embodiments of the invention one or more control nucleic acid molecules are attached to the substrate. Preferably, control nucleic acid molecules allow determination of factors such as nucleic acid quality and binding characteristics, reagent quality and effectiveness, hybridization success, and analysis thresholds and success. Control nucleic acids may include but are not limited to expression products of genes such as housekeeping genes or fragments thereof.

The invention also permits the artisan to treat a subject having a disorder characterized by expression of a SSX-2 HLA class II binding peptide. Treatments include administering an agent which enriches in the subject a complex of a SSX-2 HLA class II binding peptide and an HLA class II molecule, and administering $CD4^+$ T lymphocytes which are specific for such complexes. Agents useful in the foregoing treatments include SSX-2 HLA class II binding peptides and functional variants thereof, proteins including such SSX-2 HLA class II binding peptides, optionally containing endosome targeting sequences fused to the SSX-2 sequences, nucleic acids which express such proteins and peptides (including viruses and other vectors that contain the nucleic acids), complexes of such peptides and HLA class II binding molecules (e.g., HLA-DR), antigen presenting cells bearing complexes of a SSX-2 HLA class II binding peptide and an HLA class II binding molecule (such as dendritic cells bearing one or more SSX-2 HLA class II binding peptides bound to HLA class II molecules), and the like. The invention also permits an artisan to selectively enrich a population of T lymphocytes for $CD4^+$ T lymphocytes specific for a SSX-2 HLA class II binding peptide. Similar methods can be practiced using the SSX family peptides described herein as being structurally related to the SSX-2 HLA class II binding peptides.

The isolation of the SSX-2 HLA class II binding peptides also makes it possible to isolate and/or synthesize nucleic acids that encode the SSX-2 HLA class II binding peptides. Nucleic acids can be used to produce in vitro or in prokaryotic or eukaryotic host cells the SSX-2 HLA class II binding peptides.

Peptides comprising the SSX-2 HLA class II binding peptide of the invention may be synthesized in vitro, using standard methods of peptide synthesis, preferably automated peptide synthesis. In addition, a variety of other methodologies well-known to the skilled practitioner can be utilized to obtain isolated SSX-2 HLA class II binding peptides. For example, an expression vector may be introduced into cells to cause production of the peptides. In another method, mRNA transcripts may be microinjected or otherwise introduced into cells to cause production of the encoded peptides. Translation of mRNA in cell-free extracts such as the reticulocyte lysate system also may be used to produce peptides. Those skilled in the art also can readily follow known methods for isolating peptides in order to obtain isolated SSX-2 HLA class II binding peptides. These include, but are not limited to, immunochromatography, HPLC, size-exclusion chromatography, ion-exchange chromatography and immune-affinity chromatography.

These isolated SSX-2 HLA class II binding peptides, proteins which include such peptides, or complexes of the peptides and HLA class II molecules, such as HLA-DR, may be combined with materials such as adjuvants to produce vaccines useful in treating disorders characterized by expression of the SSX-2 HLA class II binding peptide. Preferably, vaccines are prepared from antigen presenting cells that present the SSX-2 HLA class II binding peptide/HLA class II complexes on their surface, such as dendritic cells, B cells, non-proliferative transfectants, etcetera. In all cases where cells are used as a vaccine, these can be cells transfected with coding sequences for one or both of the components necessary to stimulate $CD4^+$ lymphocytes, or can be cells which already express both molecules without the need for transfection. For example, autologous antigen presenting cells can be isolated from a patient and treated to obtain cells which present SSX-2 epitopes in association of HLA class I and HLA class II molecules. These cells would be capable of stimulating both $CD4^+$ and $CD8^+$ cell responses. Such antigen presenting cells can be obtained by infecting dendritic cells with recombinant viruses encoding an Ii.SSX-2 fusion protein. Dendritic cells also can be loaded with HLA class I and HLA class II peptide epitopes.

Vaccines also encompass naked DNA or RNA, encoding a SSX-2 HLA class II binding peptide or precursor thereof, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (*Science* 259:1745-1748, 1993). Vaccines also include nucleic acids packaged in a virus, liposome or other particle, including polymeric particles useful in drug delivery.

The immune response generated or enhanced by any of the treatments described herein can be monitored by various methods known in the art. For example, the presence of T cells specific for a SSX-2 antigen can be detected by direct labeling of T cell receptors with soluble fluorogenic MHC molecule tetramers (or multimers) which present the antigenic SSX-2 peptide (Altman et al., *Science* 274:94-96, 1996; Dunbar et al., *Curr. Biol.* 8:413-416, 1998). Briefly, soluble MHC class 1 molecules are folded in vitro in the presence of β2-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio of 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein. The use of MHC class II molecules as tetramers was recently demonstrated by Crawford et al. (*Immunity* 8:675-682, 1998; see also Dunbar and Ogg, *J. Immunol. Methods* 268(1):3-7, 2002; Arnold et al., *J. Immunol. Methods* 271(1-2):137-151, 2002). Multimeric soluble MHC class II molecules were complexed with a covalently attached peptide (which can be attached with or without a linker molecule), but peptides also can be loaded onto class II molecules. The class II tetramers were shown to bind with appropriate specificity and affinity to specific T cells. Thus tetramers can be used to monitor both $CD4^+$ and $CD8^+$ cell responses to vaccination protocols. Methods for preparation of multimeric complexes of MHC class II molecules are described in Hugues et al., *J. Immunological Meth.* 268: 83-92 (2002) and references cited therein, each of which is incorporated by reference.

The SSX-2 HLA class II binding peptide, as well as complexes of SSX-2 HLA class II binding peptide and HLA molecule, also may be used to produce antibodies, using standard techniques well known to the art. Standard reference works setting forth the general principles of antibody production include Catty, D., *Antibodies, A Practical Approach*, Vol. 1, IRL Press, Washington D.C. (1988); Klein, J., *Immunology: The Science of Cell-Non-Cell Discrimination*, John Wiley and Sons, New York (1982); Kennett, R., et al., *Monoclonal Antibodies, Hybridoma, A New Dimension In Biological Analyses*, Plenum Press, New York (1980); Campbell, A., *Monoclonal Antibody Technology*, in *Laboratory Techniques and Biochemistry and Molecular Biology*, Vol. 13 (Burdon, R. et al. EDS.), Elsevier Amsterdam (1984); and Eisen, H. N., *Microbiology*, third edition, Davis, B. D. et al. EDS. (Harper & Rowe, Philadelphia (1980).

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816, 567, 5,225,539, 5,585,089, 5,693,762 and 5,859,205.

Fully human monoclonal antibodies also can be prepared by immunizing mice transgenic for large portions of human immunoglobulin heavy and light chain loci. See, e.g., U.S. Pat. Nos. 5,545,806, 6,150,584, and references cited therein. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The antibodies of the present invention thus are prepared by any of a variety of methods, including administering protein, fragments of protein, cells expressing the protein or fragments thereof and an appropriate HLA class II molecule, and the like to an animal to induce polyclonal antibodies. The production of monoclonal antibodies is according to techniques well known in the art. Antibodies prepared according to the invention also preferably are specific for the peptide/HLA complexes described herein.

The antibodies of this invention can be used for experimental purposes (e.g., localization of the HLA/peptide complexes, immunoprecipitations, Western blots, flow cytometry, ELISA etc.) as well as diagnostic or therapeutic purposes (e.g., assaying extracts of tissue biopsies for the presence of the SSX-2 peptides, HLA/peptide complexes, targeting delivery of cytotoxic or cytostatic substances to cells expressing the appropriate HLA/peptide complex). The antibodies of this invention are useful for the study and analysis of antigen presentation on tumor cells and can be used to assay for changes in the HLA/peptide complex expression before, during or after a treatment protocol, e.g., vaccination with peptides, antigen presenting cells, HLA/peptide tetramers, adoptive transfer or chemotherapy.

The antibodies and antibody fragments of this invention may be coupled to diagnostic labeling agents for imaging of cells and tissues that express the HLA/peptide complexes or may be coupled to therapeutically useful agents by using standard methods well-known in the art. The antibodies also may be coupled to labeling agents for imaging e.g., radiolabels or fluorescent labels, or may be coupled to, e.g., biotin or antitumor agents, e.g., radioiodinated compounds, toxins such as ricin, methotrexate, cytostatic or cytolytic drugs, etc. Examples of diagnostic agents suitable for conjugating to the antibodies of this invention include e.g., barium sulfate, diatrizoate sodium, diatrizoate meglumine, iocetamic acid, iopanoic acid, ipodate calcium, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium. As used herein, "therapeutically useful agents" include any therapeutic molecules, which are preferably targeted selectively to a cell expressing the HLA/peptide complexes, including antineoplastic agents, radioiodinated compounds, toxins, other cytostatic or cytolytic drugs. Antineoplastic therapeutics are well known and include: aminoglutethimide, azathioprine, bleomycin sulfate, busulfan, carmustine, chlorambucil, cisplatin, cyclophosphamide, cyclosporine, cytarabidine, dacarbazine, dactinomycin, daunorubicin, doxorubicin, taxol, etoposide, fluorouracil, interferon-.alpha., lomustine, mercaptopurine, methotrexate, mitotane, procarbazine HCl, thioguanine, vinblastine sulfate and vincristine sulfate. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division). Toxins can be proteins such as, for example, pokeweed anti-viral protein, cholera toxin, pertussis toxin, ricin, gelonin, abrin, diphtheria exotoxin, or *Pseudomonas* exotoxin. Toxin moieties can also be high energy-emitting radionuclides such as cobalt-60. The antibodies may be administered to a subject having a pathological condition characterized by the presentation of the HLA/peptide complexes of this invention, e.g., melanoma or other cancers, in an amount sufficient to alleviate the symptoms associated with the pathological condition.

When "disorder" or "condition" is used herein, it refers to any pathological condition where the SSX-2 HLA class II binding peptide is expressed. Such disorders include cancers, such as biliary tract cancer; bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS-associated leukemias and adult T-cell leukemia lymphoma; intraepithelial neoplasms including Bowen's disease and Paget's disease; liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilms tumor.

Some therapeutic approaches based upon the disclosure are premised on inducing a response by a subject's immune system to SSX HLA class II binding peptide presenting cells. One such approach is the administration of autologous $CD4^+$ T cells specific to the complex of SSX-2 HLA class II binding peptide and an HLA class II molecule to a subject with abnormal cells of the phenotype at issue. It is within the skill of the artisan to develop such $CD4^+$ T cells in vitro. Generally, a sample of cells taken from a subject, such as blood cells, are contacted with a cell presenting the complex and capable of provoking $CD4^+$ T lymphocytes to proliferate. The target cell can be a transfectant, such as a COS cell, or an antigen presenting cell bearing HLA class II molecules, such as dendritic cells or B cells preferably autologous APCs such as dendritic cells (DC) purified from PBMC. DC could be transfected of pulsed with antigen, either full length protein or peptide. (Ayyoub, M et al J. Immunol. 2004 172:7206-7211, Ayyoub M. et al. J Clin Invest 2004 113:1225-33.) These transfectants present the desired complex of their surface and, when combined with a $CD4^+$ T lymphocyte of interest, stimulate its proliferation. COS cells are widely available, as are other suitable host cells. Specific production of $CD4^+$ T lymphocytes is described below. The clonally expanded autologous $CD4^+$ T lymphocytes then are administered to the subject. The $CD4^+$ T lymphocytes then stimulate the subject's immune response, thereby achieving the desired therapeutic goal.

CTL proliferation can be increased by increasing the level of tryptophan in T cell cultures, by inhibiting enzymes which catabolizes tryptophan, such as indoleamine 2,3-dioxygenase (IDO), or by adding tryptophan to the culture (see, e.g., PCT application WO99/29310). Proliferation of T cells is enhanced by increasing the rate of proliferation and/or extending the number of divisions of the T cells in culture. In addition, increasing tryptophan in T cell cultures also enhances the lytic activity of the T cells grown in culture.

The foregoing therapy assumes that at least some of the subject's abnormal cells present the relevant HLA/peptide complex. This can be determined very easily, as the art is very familiar with methods for identifying cells which present a particular HLA molecule, as well as how to identify cells expressing DNA of the pertinent sequences, in this case a SSX-2 sequence.

The foregoing therapy is not the only form of therapy that is available in accordance with the invention. $CD4^+$ T lymphocytes can also be provoked in vivo, using a number of approaches. One approach is the use of non-proliferative cells expressing the complex. The cells used in this approach may be those that normally express the complex, such as dendritic cells or cells transfected with one or both of the genes necessary for presentation of the complex. Chen et al., (*Proc. Natl. Acad. Sci. USA* 88: 110-114, 1991) exemplifies this approach, showing the use of transfected cells expressing HPV-E7 peptides in a therapeutic regime. Various cell types may be used. Similarly, vectors carrying one or both of the genes of interest may be used. Viral or bacterial vectors are especially preferred. For example, nucleic acids which encode a SSX-2 HLA class II binding peptide may be operably linked to promoter and enhancer sequences which direct expression of the SSX-2 HLA class II binding peptide in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding SSX-2 HLA class II binding peptides. Nucleic acids encoding a SSX-2 HLA class II binding peptide also may be inserted into a retroviral genome, thereby facilitating integration of the nucleic acid into the genome of the target tissue or cell type. In these systems, the gene of interest is carried by a microorganism, e.g., a *Vaccinia* virus, poxviruses in general, adenovirus, herpes simplex virus, retrovirus or the bacteria BCG, and the materials de facto "infect" host cells. The cells which result present the complex of interest, and are recognized by autologous CD4$^+$ T cells, which then proliferate.

A similar effect can be achieved by combining a SSX HLA class II binding peptide with an adjuvant to facilitate incorporation into HLA class II presenting cells in vivo. If larger than the HLA class II binding portion (e.g., SEQ ID NOs:10, 22-25 28, 29, 30, 31, 42, 52, 53, 54 and 55), the SSX-2 HLA class II binding peptide can be processed if necessary to yield the peptide partner of the HLA molecule while the peptides disclosed herein are believed to be presented without the need for further processing. Likewise SEQ ID NO:81 and SEQ ID NO:82 could be used in a similar manner. Generally, subjects can receive an intradermal, intravenous, subcutaneous or intramuscular injection of an effective amount of the SSX-2 HLA class II binding peptide. Initial doses can be followed by bi- or tri-weekly, weekly or monthly booster doses, following immunization protocols standard in the art.

A preferred method for facilitating incorporation of SSX-2 HLA class II binding peptides into HLA class II presenting cells is by expressing in the presenting cells a polypeptide which includes an endosomal targeting signal fused to a SSX-2 polypeptide which includes the class II binding peptide. Particularly preferred are SSX-2 fusion proteins which contain human invariant chain Ii.

Any of the foregoing compositions or protocols can include also SSX HLA class I binding peptides for induction of a cytolytic T lymphocyte response. For example, the SSX-2 protein can be processed in a cell to produce both HLA class I and HLA class II responses. SSX-2 peptides have been described in U.S. Pat. No. 6,548,064, and by Ayyoub et al. (*J Immunol* 168(4):1717-22, 2002) and Rubio-Godoy et al. (*Eur J Immunol*. 32:2292-2299, 2002). SSX gene and protein family members are disclosed in U.S. Pat. Nos. 6,291,658 and 6,339,140. By administering SSX-2 peptides which bind HLA class I and class II molecules (or nucleic acid encoding such peptides), an improved immune response may be provided by inducing both T helper cells and cytotoxic T cells.

In addition, non-SSX-2 tumor associated peptides also can be administered to increase immune response via HLA class I and/or class II. It is well established that cancer cells can express more that one tumor associated gene. It is within the scope of routine experimentation for one of ordinary skill in the art to determine whether a particular subject expresses additional tumor associated genes, and then include HLA class I and/or HLA class II binding peptides derived from expression products of such genes in the foregoing SSX-2 compositions and vaccines.

Especially preferred are nucleic acids encoding a series of epitopes, known as "polytopes". The epitopes can be arranged in sequential or overlapping fashion (see, e.g., Thomson et al., *Proc. Natl. Acad. Sci. USA* 92:5845-5849, 1995; Gilbert et al., *Nature Biotechnol.* 15:1280-1284, 1997), with or without the natural flanking sequences, and can be separated by unrelated linker sequences if desired. The polytope is processed to generated individual epitopes which are recognized by the immune system for generation of immune responses.

Thus, for example, SSX-2 HLA class II binding peptides can be combined with peptides from other tumor rejection antigens (e.g. by preparation of hybrid nucleic acids or polypeptides) and with SSX-2 HLA class I binding peptides (some of which are listed below) to form "polytopes". Exemplary tumor associated peptide antigens that can be administered to induce or enhance an immune response are derived from tumor associated genes and encoded proteins including MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), tyrosinase, brain glycogen phosphorylase, Melan-A, MAGE-C1 (CT-7), MAGE-C2, NY-ESO-1, LAGE-1, SSX-1, SSX-3, SSX-4, SSX-5, SCP-1 and CT-10. For example, antigenic peptides characteristic of tumors include those listed in published PCT application WO 00/20581 (PCT/US99/21230).

Other examples of HLA class I and HLA class II binding peptides will be known to one of ordinary skill in the art (for example, see Coulie, *Stem Cells* 13:393-403, 1995), and can be used in the invention in a like manner as those disclosed herein. One of ordinary skill in the art can prepare polypeptides comprising one or more SSX-2 peptides and one or more of the foregoing tumor rejection peptides, or nucleic acids encoding such polypeptides, according to standard procedures of molecular biology.

Thus polytopes are groups of two or more potentially immunogenic or immune response stimulating peptides which can be joined together in various arrangements (e.g. concatenated, overlapping). The polytope (or nucleic acid encoding the polytope) can be administered in a standard immunization protocol, e.g. to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., *Proc. Acad. Natl. Acad. Sci. USA* 92(13):5845-5849, 1995; Gilbert et al., *Nature Biotechnol.* 15(12):1280-1284, 1997; Thomson et al., *J. Immunol.* 157(2):822-826, 1996; Tam et al., *J. Exp. Med.* 171(1):299-306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type. Polytopes can be introduced to a patient in need of such treatment as polypeptide structures, or via the use of nucleic acid delivery systems known in the art (see, e.g., Allsopp et al., *Eur. J. Immunol.* 26(8):1951-1959, 1996). Adenovirus, pox virus, Ty-virus like particles, adeno-associated virus, plasmids, bacteria, etc. can be used in such delivery. One can test the polytope delivery systems in mouse models to determine efficacy of the delivery system. The systems also can be tested in human clinical trials.

As part of the immunization compositions, one or more substances that potentiate an immune response are administered along with the peptides described herein. Such substances include adjuvants and cytokines. An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella minnesota* Re 595 lipopolysaccharide; saponins including QS21 (SmithKline Beecham), a pure QA-21 saponin purified from *Quillja saponaria* extract; DQS21, described in PCT application WO96/33739 (SmithKline Beecham); ISCOM (CSL Ltd., Parkville, Victoria, Australia) derived from the bark of the *Quillaia saponaria* molina tree; QS-7, QS-17, QS-18, and QS-L1 (So et al., *Mol. Cells.* 7:178-186, 1997); incomplete Freund's adjuvant; complete Freund's adjuvant; montanide; immunostimulatory oligonucleotides (see e.g. CpG oligonucleotides described by Kreig et al., *Nature* 374:546-9, 1995); reagents that bind to one of the toll-like receptors; vitamin E and various water-in-oil emulsions prepared from biodegradable oils such as squalene and/or tocopherol; and factors that are taken up by the so-called 'toll-like receptor 7' on certain immune cells that are found in the outside part of the skin, such as imiquimod (3M, St. Paul, Minn.). Preferably, the peptides are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 µg to about 100 µg. Other adjuvants are known in the art and can be used in the invention (see, e.g. Goding, *Monoclonal Antibodies: Principles and Practice*, 2nd Ed., 1986). Methods for the preparation of mixtures or emulsions of peptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., *Science* 268: 1432-1434, 1995), GM-CSF, IL-18 and IL-15 (Klebanoff et al. Proc. Natl. Acad. Sci. USA 2004 101:1969-74). Thus cytokines can be administered in conjunction with antigens and adjuvants to increase the immune response to the antigens. There are a number of additional immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation, and effector function. B7 also interacts with CTLA4 (CD152) on T cells and studies involving CTLA4 and B7 ligands indicate that the B7-CTLA4 interaction can enhance antitumor immunity and CTL proliferation (Zheng et al., *Proc. Nat'l Acad. Sci. USA* 95:6284-6289, 1998).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol.* 154:5637-5648, 1995). Tumor cell transfection with B7 has been discussed in relation to in vitro CTL expansion for adoptive transfer immunotherapy by Wang et al. (*J. Immunother.* 19:1-8, 1996). Other delivery mechanisms for the B7 molecule would include nucleic acid (naked DNA) immunization (Kim et al., *Nature Biotechnol.* 15:7:641-646, 1997) and recombinant viruses such as adeno and pox (Wendtner et al., *Gene Ther.* 4:726-735, 1997). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-ICOS antibodies (Hutloff et al., *Nature* 397:263-266, 1999).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.*, 158:637-642, 1997; Fenton et al., *J. Immunother.*, 21:95-108, 1998).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., 1998). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., *Nature* 393:474, 1998; Bennett et al., *Nature* 393:478, 1998; Schoenberger et al., *Nature* 393:480, 1998). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor associated antigens which are normally encountered outside of an inflammatory context or are presented by non-professional APCs (tumor cells). Other methods for inducing maturation of dendritic cells, e.g., by increasing CD40-CD40L interaction, or by contacting DCs with CpG-containing oligodeoxynucleotides or stimulatory sugar moieties from extracellular matrix, are known in the art. In these situations Th help and B7 costimulation signals are not provided. This mechanism might be used in the context of antigen pulsed DC based therapies or in situations where Th epitopes have not been defined within known tumor associated antigen precursors.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. In the case of inducing an immune response, the desired response is an increase in antibodies or T lymphocytes which are specific for the SSX-2 immunogen(s) employed. These desired responses can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 milligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

EXAMPLES

Because of its expression in different tumor types, the cancer/testis antigen SSX-2 is among the most promising candidates for the development of generic cancer vaccines. SSX-2 is a classical cancer testis antigen belonging to a multigene family mapping to chromosome X. Some family members, including SSX-2, are expressed in a wide variety of tumors (Naka et al. *Int J Cancer* 2002. 98:640-642). The SSX-2 encoding gene was initially described as one of two partner genes found in a recurrent chromosomal translocation in synovial sarcoma (Clark et al. *Nat Genet*. 1994. 7:502-508; Crew et al. *EMBO J*. 1995. 14:2333-2340), and more recently identified by SEREX analysis of serum from a melanoma patient. The potential spontaneous immunogenicity of the SSX-2 antigen was initially suggested by detection of specific antibodies in 10% of melanoma patients (Tureci et al, *Cancer Res* 1996. 56:4766-4772). By analyzing CD8$^+$ T lymphocytes from an SSX-2 expressing melanoma patient, an epitope was identified mapping to the 41-49 region of the SSX-2 protein and recognized by tumor-reactive CD8$^+$ T lymphocytes in association with the MHC Class I allele HLA-A2 (Rubio-Godoy et al., *Eur J Immunol*. 32:2292-2299, 2002; Ayyoub et al. *J Immunol* 168:1717-1722, 2002). Importantly, whereas a large functional avidity of antigen recognition and tumor reactivity has been found among isolated SSX2 41-49 specific CD8$^+$ T cells, those isolated from both tumor infiltrating and circulating lymphocytes of patients bearing SSX-2 expressing tumor lesions uniformly exhibited high functional avidity of antigen recognition and tumor reactivity. These findings indicate that spontaneous T cell responses to SSX-2 frequently occur in antigen expressing melanoma patients, encouraging the search for additional MHC class I and class II restricted epitopes in this patient population.

A CD4$^+$ T cell epitope encoded by SSX-2 now has been identified, as described herein.

Materials and Methods

Cell lines and tissue culture. Melanoma cell lines and anti HLA-DR (D1.12), HLA-DP (B7.21.3) and HLA-DQ (BT3/4) antibodies were kindly provided by Dr. D. Rimoldi (Ludwig Institute for Cancer Research, Lausanne, Switzerland). Cell lines were maintained in RPMI 1640 (Life Technologies, Gaithersburg, Md.) supplemented with 10% heat inactivated fetal calf serum (FCS). Culture medium for lymphocytes was IMDM (Life Technologies, Basel, Switzerland) supplemented with 8% heat inactivated pooled human serum (CTL medium), human recombinant IL-2 (Glaxo, Geneva, Switzerland) and IL-7 (Biosource International, Camarillo, Calif.).

Generation of SSX-2 specific CD4$^+$ T cells. In vitro sensitization of CD4$^+$ T cells was carried out as described previously for CD8$^+$ T cells. Briefly, 1 to 2×10$^6$ CD4$^+$ T cells highly enriched from peripheral blood mononuclear cells (PBMC) by magnetic cell sorting using a miniMACS device (Miltenyi Biotec, Sunnyvale, Calif., USA) were stimulated with a mixture containing peptides spanning the entire SSX-2 protein sequence (Ayyoub et al, *J Immunol* 2002. 32:2292-2299) (2 µM each) in the presence of irradiated autologous cells from the CD4$^-$ fraction in CTL medium containing rhIL-2 (10 U/ml) and IL-7 (10 pg/ml). The enriched CD4$^+$ T cells were cultured 2-3 weeks prior to being tested. CD4$^+$ T cells secreting cytokines in response to peptide stimulation were isolated by cytokine guided flow cytometry cell sorting using the cytokine secretion detection kit (Miltenyi Biotec) and cloned by limiting dilution culture in the presence of PHA (Sigma), allogenic irradiated PBMC and rhIL-2 as described (Valmori et al., 2001, *Cancer Res*. 61:501-512). Clones were subsequently expanded by periodic (3-4 weeks) stimulation under the same conditions.

The SSX-2 plasmid contained the SSX-2 cDNA cloned into pcDNA3.1 vector. Tumor cells were transiently transfected with plasmids using FuGENE according to the manufacture's instructions (Roche Diagnostics, Rotkreuz, Switzerland).

Antigen recognition assays. For detection of cytokine secretion in the culture supernatant T cells (10,000) were incubated with stimulating cells (15,000/well) in 96-well round-bottom plates in 200 µl/well of IMDM containing 10% human serum and 20 U/ml hrIL2. After 24 h incubation at 37° C., culture supernatants were collected and the content of IFN-γ determined by ELISA (BioSource Europe, Fleurus, Belgium). IFN-γ ELISPOT assay was performed as described previously (Ayyoub M. et al, 2002, *J Immunol* 32:2292-2299) using nitrocellulose-lined 96-well microplates (MAHA S45: Millipore, Bedford, Mass.) and an IFN-γ ELISPOT kit (DIA-CLONE, Besancon, France). Stimulator cells (5×10⁴/well) were added together with the indicated number of T cells and peptide (2 µM) where indicated. Spots were counted using a stereomicroscope with a magnification of ×15.

Example 1

Isolation of SSX-2 Specific CD4⁺ T Cells from Circulating Lymphocytes of an Antigen Expressing Melanoma Patient As recombinant SSX-2 protein became available, we initiated a study to identify CD4⁺ T cell epitopes. To that purpose, we prepared monocyte-derived dendritic cells (DC) from patient LAU672 by isolating CD 14+ monocytes from PBMC by magnetic cell sorting. The obtained population (containing >95% CD14⁺ cells) was cultured in CTL medium containing 1,000 U/ml of rhGM-CSF and 1,000 U/ml of rhIL-4 during 6 days. At the end of the culture period, DC were incubated with recombinant SSX-2 protein for 12 hours and used to stimulate autologous CD4⁺ T cells isolated from PBMC by magnetic cell sorting.

Figure 1:
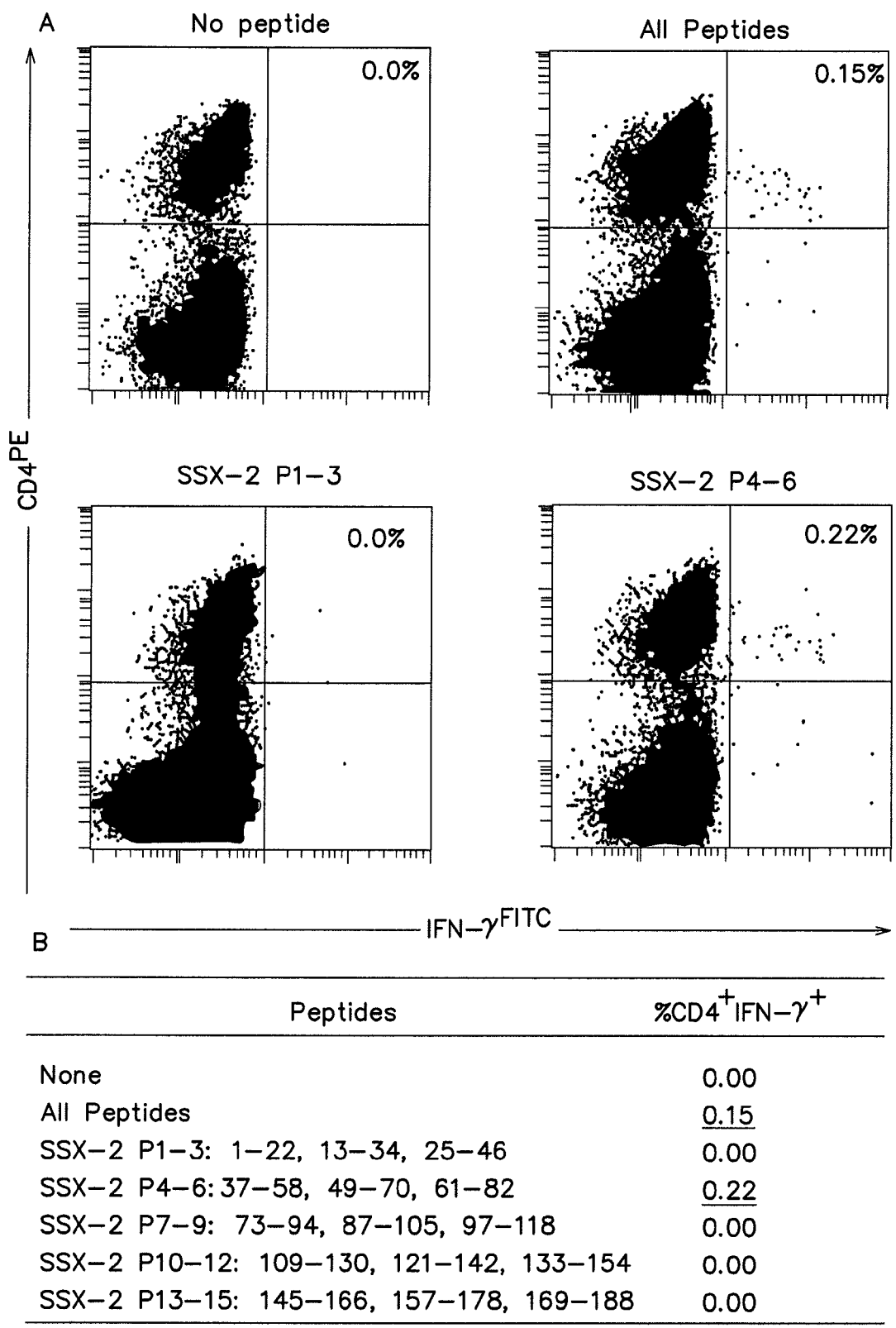
FIG. 1 depicts detection of additional SSX-2 specific CD4+ T cells in peptide stimulated cultures.

Two weeks after stimulation, culture aliquots were tested using either a pool containing all SSX-2 overlapping peptides or submixtures, each composed of 3 peptides (P1-3, P4-6 etc., FIG. 1). The submixtures were composed as follows: P1-3 was composed of the peptides as set forth in SEQ ID NO:7, SEQ ID NO:8, SEQ ID NO:9; P4-6 was composed of the peptides as set forth in SEQ ID NO:10, SEQ ID NO:11, SEQ ID NO:12; P7-9 was composed of the peptides as set forth in SEQ ID NO:13, SEQ ID NO:14, SEQ ID NO:15; P10-12 was composed of the peptides as set forth in SEQ ID NO:16, SEQ ID NO:17, SEQ ID NO:18; and P13-15 was composed of the peptides as set forth in SEQ ID NO:19, SEQ ID NO:20, SEQ ID NO:21.

The presence of specific CD4⁺ T cells was monitored by intracellular staining with INF-γ specific antibodies (FIG. 1A). One peptide submixture (P4-6, containing peptides SSX-2 37-58, 49-70 and 61-82; SEQ ID NOs:10-12) stimulated a significant proportion of IFN-γ secreting CD4⁺ T cells, as compared to controls containing either no peptide or other peptide mixtures (FIG. 1). It is noteworthy that the proportion of IFN-γ secreting CD4⁺ T cells in the P4-6 stimulated culture was equivalent to that obtained upon stimulation with the peptide mix containing all overlapping peptides (FIG. 1A).

Figure 2:
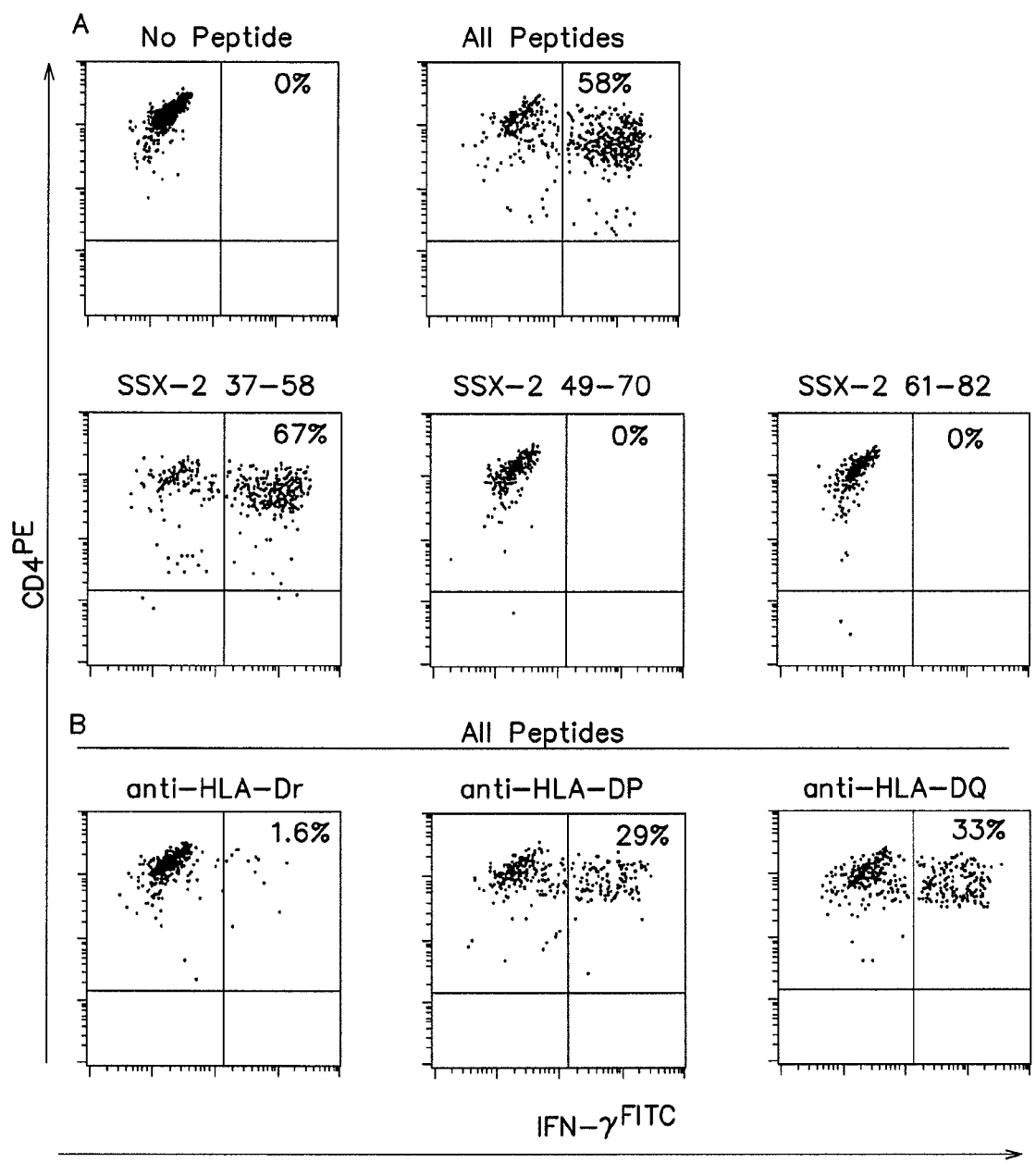
FIG. 2 shows FACS analysis of stimulated cells that were cloned under limiting dilution conditions.

SSX-2 specific CD4⁺ T cells were isolated from the culture by cytokine secretion guided magnetic cell sorting as described previously and expanded either as bulk populations or cloned under limiting dilution conditions. The obtained CD4⁺ T cell populations were used to further determine and characterize the identified epitope(s). Assessment of reactivity to single peptides in the submixture P4-6 was done using these populations. As shown in FIG. 2A for one representative clone, this analysis revealed that SSX-2 37-58 was the active peptide, whereas no significant activity was detected in response to the other two peptides in the submixture, SSX-2 49-70 and SSX-2 61-82.

Example 2

SSX-2 37-58 is Recognized by Specific CD4⁺ T cells from LAU672 in the Context of HLA-DR11

To identify the restriction element used by SSX-2 37-58 specific CD4⁺ T cells from patient LAU672, peptide presentation experiments were performed in the presence of antibodies that specifically block the recognition of antigens restricted by different MHC Class II elements (HLA-DR, -DP or -DQ). As illustrated in FIG. 2B, anti-HLA-DR antibodies almost completely inhibited peptide recognition by T cells. In contrast, only partial inhibition was observed using anti-HLA-DP or anti-HLA-DQ antibodies (FIG. 2B). The latter was to be considered non-specific as it was similarly observed when using an MHC-Class-I restricted CD8 + T cell clone.

To establish the presenting allele(s) we first analyzed the HLA-DR alleles of the patient. LAU 672 expressed HLA-DR11 and DR17. We then assessed presentation by partially matched APC from other melanoma patients. In the case of two patients expressing DR11 but not DR17, LAU567 (DR11, DR15) and, LAU14 (DR11, DR13) we obtained efficient presentation whereas in the case of two patients expressing DR17 but not DR11, LAU465 (DR17, DR4) and LAU203 (DR17, DR15) no presentation was observed. Thus, DR11 was the presenting allele in the case of patient LAU 672.

To then establish the frequency at which MHC-class II molecules in the local population were able to present the SSX-2 epitope to specific CD4⁺ T cells from LAU 672, PBMC from healthy donors were tested for their capacity to present peptide SSX-2 37-58. We obtained presentation by 8 out of 20 PBMC analyzed suggesting a frequency of the presenting allele(s) in the Caucasian test population of about 40% (not shown). As the frequency of DR11 is expected to be lower (i.e. is of about 10% in the Caucasian USA population) these data suggest that the identified peptide can be recognized by T cells in the context of multiple DR alleles. HLA-DR typing of the 8 presenting healthy donors is pending.

Example 3

Figure 3:
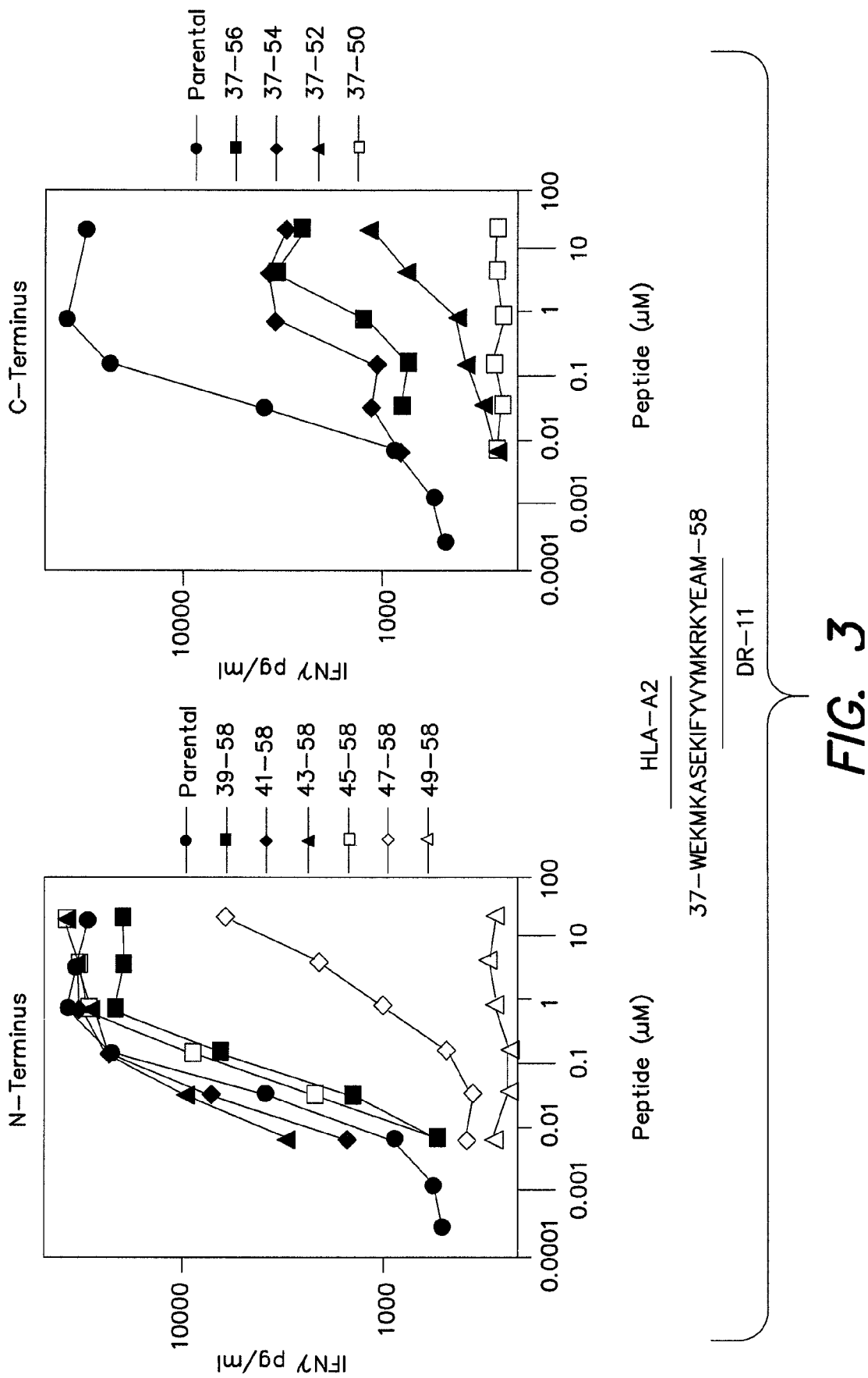
FIG. 3 shows an analysis of the relative capacity of truncated variants of SSX-2 37-58 to stimulate IFN-γ secretion by specific T cells. N-terminal and C-terminal truncations of peptide SSX-2 37-58 (WEKMKASEKIFYVYMKRK-YEAM; SEQ ID NO:10) were used as shown: SSX-2 39-58 (KMKASEKIFYVYMKRKYEAM; SEQ ID NO:22); SSX-2 41-58 (KASEKIFYVYMKRKYEAM; SEQ ID NO:23); SSX-2 43-58 (SEKIFYVYMKRKYEAM; SEQ ID NO:24); SSX-2 45-58 (KIFYVYMKRKYEAM; SEQ ID NO:25); SSX-2 47-58 (FYVYMKRKYEAM; SEQ ID NO:26); SSX-2 49-58 (VYMKRKYEAM; SEQ ID NO:27); SSX-2 37-56 (WEKMKASEKIFYVYMKRKYE; SEQ ID NO:28); SSX-2 37-54 (WEKMKASEKIFYVYMKRK; SEQ ID NO:29); SSX-2 37-52 (WEKMKASEKIFYVYMK; SEQ ID NO:30); and SSX-2 37-50 (WEKMKASEKIFYVY; SEQ ID NO:31). The truncated peptide exhibiting the best binding properties as evidenced by IFN-γ release (i.e., the "optimal" peptide) is SSX-2 45-58: KIFYVYMKRKYEAM; SEQ ID NO:25.
Figure 4A:
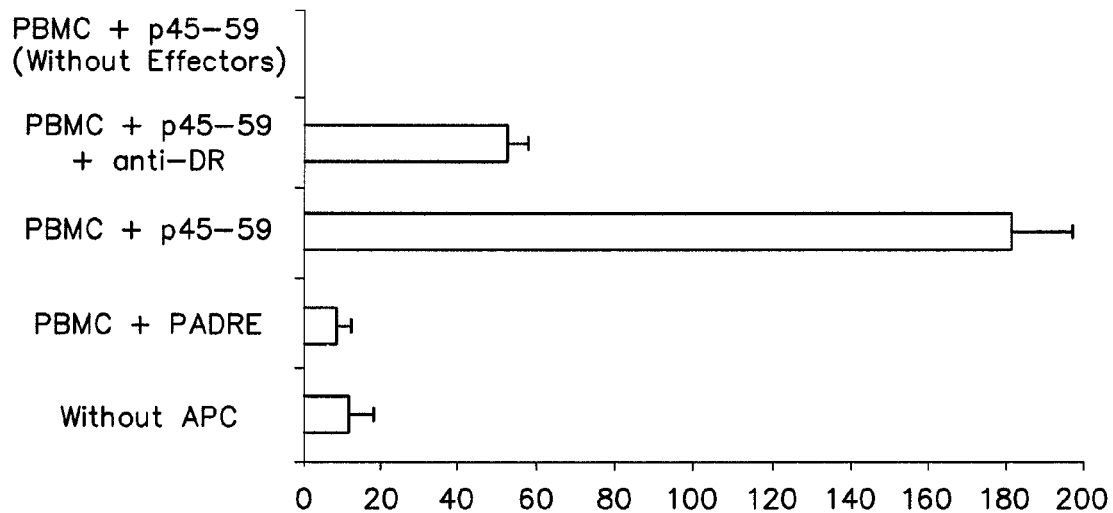
FIG. 4 shows T-cell responses against the HOM-MEL40/SSX2 derived peptide p45-59. Interferon-γ ELISPOT assay of three responding breast cancer patients (FIG. 4A: BC 355.
FIG. 4B: BC400.
FIG. 4C: BC403) and one healthy control (FIG. 4D: Col7). X axes represent the number of IFN-γ spots/ $2.5 \times 10^4$ CD4+ T-cells.
Figure 4B:
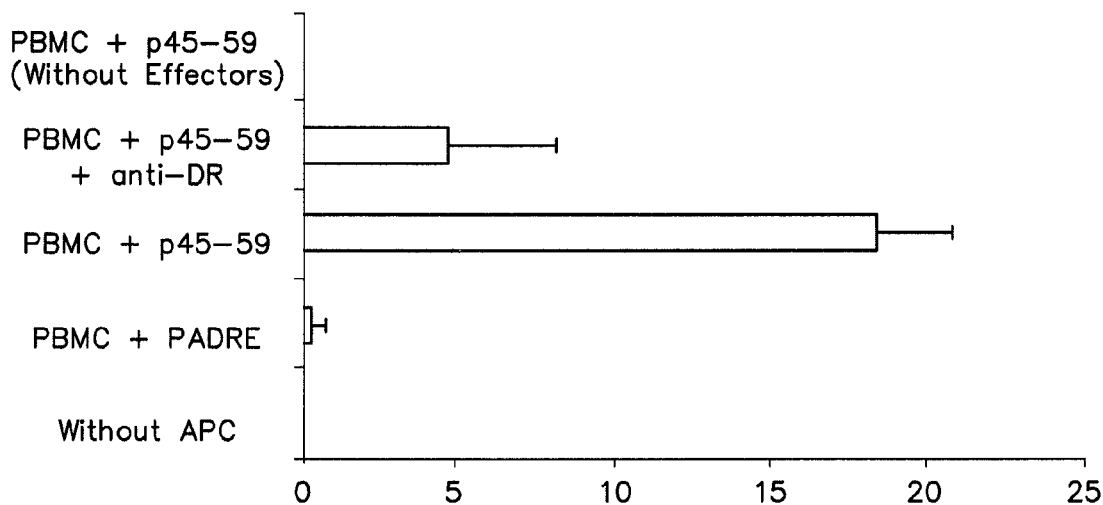
Figure 4C:
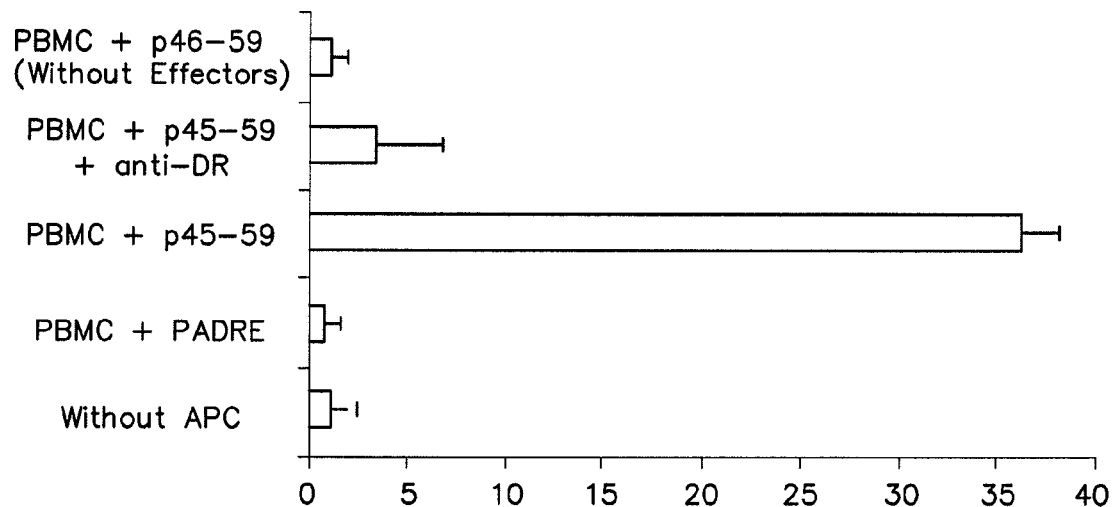
Figure 4D:
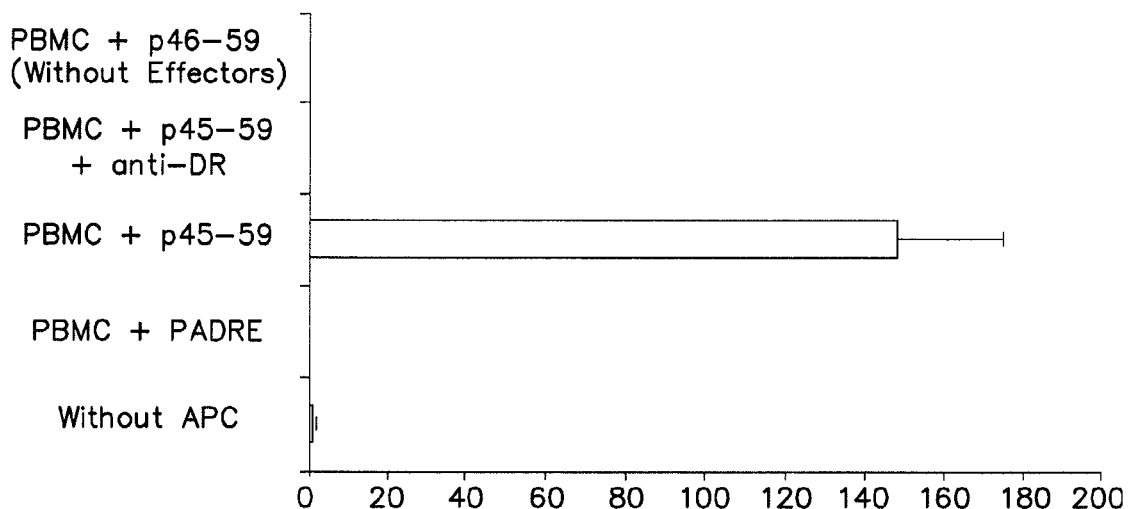

Identification of the Minimal Peptide Sequence Optimally Recognized by SSX-2 Specific DR11-Restricted CD4⁺ T cells To more precisely define the SSX-2-derived peptide optimally recognized by DR11-restricted specific CD4⁺ T cells from patient LAU 672, we analyzed the relative capacity of truncated variants of SSX-2 37-58 to stimulate IFN-γ secretion by specific T cells. As illustrated in FIG. 3, truncation of the peptide C-terminus resulted in decreased peptide recognition. In contrast, truncation of the first 8 amino acids at the N-terminus did not significantly affect recognition (peptides having SSX-2 amino acids 39-58 (SEQ ID NO:22), 41-58 (SEQ ID NO:23), 43-58 (SEQ ID NO:24), and 45-58 (SEQ ID NO:25)) relative to the parental peptide (SSX-2 37-58 (SEQ ID NO:10)). It is expected that the peptides having amino acid sequences differing from the foregoing peptides by one amino acid also would retain activity (i.e., peptides having SSX-2 amino acids 38-58, 40-58, 42-58, and 44-58). In contrast, truncation of 2 or 4 additional N-terminal amino acids resulted in a significant reduction of peptide activity (peptides having SSX-2 amino acids 47-58 (SEQ ID NO:26), 49-58 (SEQ ID NO:27)). Therefore, this experiment allowed us to define a region, corresponding to the minimal epitope recognized by the DR-restricted T cells and located between SSX-2 residues 45 and 58, which is partially overlapping with a previously defined HLA-A2 restricted CD8+ T cell epitope (SSX-2 41-49). It is believed that a shorter peptide having amino acids 46-58 of SSX-2 also would retain activity. Interestingly, peptide SSX-2 45-58 perfectly fits with the peptide sequence predicted to optimally bind to DR11 using the SYFPEITHI prediction program (Rammensee et al., *Immunogenetics*, 50:213-219, 1999).

In view of the above-noted high degree of homology between SSX-2 and other SSX family members, we identified regions of other SSX proteins that correspond to the DR11-presented peptide. In particular, the sequence of the SSX-2 45-58 CD4+ T cell epitope identified here is highly similar to that of SSX-5 and SSX-9 (both of which have the sequence of SEQ ID NO:32), SSX-7 (SEQ ID NO:33) and SSX-3 (SEQ ID NO:34) whereas in the case of other SSX family members (e.g., SSX-8, SSX-1, SSX-6, SSX-4; see Gure et al., Int. J. Cancer 101 (5), 448-453, 2002) differences of two or more amino acids are present in this region of the corresponding proteins. For some of the shorter peptides demonstrated herein as having HLA class II binding activity and other activities, several of the peptides encoded by other SSX genes are very similar or identical. These related peptides (see Table I; including equivalent fragments as shown elsewhere herein for SSX-2) and longer peptides that include flanking amino acids of the respective protein sequences are believed to be functional variants of the SSX-2 peptides presented herein

TABLE I

Related SSX family peptides (amino acid 45-58 regions)

| Gene/ Location | Accession No. | Amino Acid Sequence | SEQ ID NO |
|---|---|---|---|
| SSX-2$_{45-58}$ | NM_003147 (isoform a); NM_175698 (isoform b) | KIFYVYMKRKYEAM | 25 |
| SSX-1$_{45-58}$ | NM_005635 | KISYVYMKRNYKAM | 36 |
| SSX-3$_{45-58}$ | NM_021014 (isoform a); NM_175711 (isoform b) | KIVYVYMKRKYEAM | 34 |
| SSX-4$_{45-58}$ | NM_005636 (isoform a); NM_175729 (isoform b) | KIVYVYMKLNYEVM | 38 |
| SSX-5$_{86-99}$ | NM_021015 (isoform a) | KIIYVYMKRKYEAM | 32 |
| SSX-5$_{45-58}$ | NM_175723 (isoform b) | KIIYVYMKRKYEAM | 32 |
| SSX-6$_{45-58}$ | NM_173357 | KISCVHMKRKYEAM | 37 |
| SSX-7$_{45-58}$ | NM_173358 | KISYVYMKRKYEAM | 33 |
| SSX-8$_{45-58}$ | BK000688 | KISYVYMKRNYEAM | 35 |
| SSX-9$_{45-58}$ | BK000689 | KIIYVYMKRKYEAM | 32 |

Amino acid differences in this area of SSX peptides relative to SEQ ID NO: 25 are underlined in bold.

Example 4

In silico Identification and Testing of SSX-2 HLA-DR Binding Peptides

The following protocol was used to determine peptide sequences from SSX-2 which might bind to HLA-DR molecules.

Hammer, et al., J. Exp. Med. 180:2353-2358 (1994), the discussion of which is incorporated by reference, presents a methodology for determining such peptides. This procedure is also described at tepitope.com, and in Hammer et al., "Techniques To Identify The Rules Governing Class II MHC-Peptide Interaction," in Fernandez et al., ed., "MHC Volume 2 A Practical Approach," Oxford University Press, 1998, pages 197-219, incorporated by reference. Further, in a paper by Sturniolo, et al., Nature Biotechnology 17: 555-567 (1999), the disclosure of which is incorporated by reference, a method is described for generating peptide sequences which might bind to particular HLA-Class II molecules. These methodologies were used in connection with the amino acid sequence of SSX-2, and with HLA-DR molecules. These peptides were then synthesized, using standard methods.

The peptides were then combined with autologous dendritic cells. These were obtained by isolating peripheral blood mononuclear cells ("PBMCs"), from HLA-DR+donors, using Ficoll-Hypaque methods. These PBMCs were then incubated for 1-2 hours at 37° C., on plastic surfaces. Adherent monocytes were then cultured for 5 days in medium that had been supplemented with interleukin-4 (IL-4) and GM-CSF. To elaborate, AIMV medium supplemented with 1000 U/ml of IL-4, and 1000 U/ml of GM-CSF was used. This incubation stimulates differentiation into dendritic cells.

Samples of dendritic cells ($8 \times 10^5$) were then loaded with 50 μg/ml of endogenously added peptide. The loading proceeded for 2 hours, at 37° C., in medium supplemented with 1000 U/ml of TNF-α and 10,000 U/ml of IL-1β. Peptide pulsed dendritic cells were then washed twice, in excess peptide free medium. Then, autologous peripheral blood lymphocytes ($4 \times 10^7$) were combined with $8 \times 10^5$ peptide loaded dendritic cells (ratio of 50:1), in medium which contained 5 ng/ml of IL-7 and 20 U/ml of IL-2. Incubation was carried out at 37° C.

Cultures were restimulated weekly with peptide loaded, irradiated PBMCs.

The ability of the peptides to form complexes with HLA-DR molecules and to stimulate CD4+ cell proliferation was determined by measuring BrdU uptake.

The specificity of the resulting CD4+ cells was then tested by combing them with autologous dendritic cells that had been loaded with peptide, admixed with full length recombinant SSX-2 protein, or with an unrelated protein.

The following peptides were identified, and synthesized, using standard methods.

```
Lys Leu Gly Phe Lys Ala Thr Leu Pro Pro Phe Met Cys Asn Lys;  (SEQ ID NO: 39)

Gln Met Thr Phe Gly Arg Leu Gln Gly Ile Ser Pro Lys Ile Met;  (SEQ ID NO: 40)

Arg Lys Gln Leu Val Ile Tyr Glu Glu Ile Ser Asp Pro Glu Glu;  (SEQ ID NO: 41)

Lys Ile Phe Tyr Val Tyr Met Lys Arg Lys Tyr Glu Ala Met Thr;  (SEQ ID NO: 42)
and Phe Gly Arg Leu Gln Gly Ile Ser Pro Lys Ile Met Pro Lys Lys.  (SEQ ID NO: 43)
```

These peptides were then tested in competitive binding assays using purified HLA-DR molecules.

The assay was described by Falcioni, et al., Nature Biotechnology 17: 562-567 (1999), incorporated by reference. In brief, the assay is a "scintillation proximity assay" using HLA-DR molecules that had been affinity purified using a monoclonal antibody. The HLA-DR molecules used were DR*0101, DR*1501, DR*0301, DR*1101, DR*0701, and DR*0801. Peptides were tested for their ability to compete with control peptide Tyr Ala Phe Arg Ala Ser Ala Lys Ala (SEQ ID NO:44) which Falcioni et al., 1999 show binds to different HLA-DR molecules.

Example 5

Proliferation of T Cells by SSX-2 HLA-DR Binding Peptides

The results presented in Example 4 led to additional experiments using T cells that had been isolated from two donors using standard protocols. In these experiments, autologous dendritic cells were prepared, as described, and combined with T cells whose proliferation was determined in a BrdU assay. In a first set of experiments, the 5 peptides set forth in Example 4 were mixed, and the mixture was compared to an equal amount of full length SSX-2 protein, and an irrelevant protein, "TALL." TALL did not stimulate proliferation at all. The SSX-2 full length molecule provoked just slightly less than 60% proliferation, while the peptide mixture provoked about 85% proliferation.

In a second set of experiments, cells taken from a donor who had been typed as positive for HLA-DR*0101 and HLA-DR*1301 were tested with the individual peptides of Example 4, a mix of the peptides, the full length SSX-2 molecule, and the TALL protein described supra. As measured in this set of experiments, the peptide of SEQ ID NO:39 provoked more proliferation than the other individual peptides or mixture of these, and performed equally as well as the full length molecule.

Six individual experiments were carried out, and in all cases, greater T cell proliferation was induced consistently by dendritic cells that had been pulsed with SEQ ID NO:39 or full length SSX-2 than with any of the other peptides, or the TALL molecule. This indicates that the full length molecule is processed to at least one Class II molecule, and that the peptide of SEQ ID NO:39 can provoke specific CD4$^+$ cells.

Example 6

Identification of SSX-2 Peptide Recognized by Several HLA-DR Haplotypes

Aiming at tumor antigen-derived epitopes binding to HLA-DR subtypes that cover a significant proportion of the population, we decided to pursue a strategy that allows for the identification of binding properties which are shared by several HLA-DR haplotypes. This should be feasible, because class II-restricted peptides have a less stringent binding pattern than class-I peptides. Employing the "SYFPEITHI" algorithm [Rammensee, et al., 1999], it became evident that the six DRB1 molecules: *0101, *0301, *0401, *0701, *1101, and *1501, which have a high prevalence among the Caucasian population [Ayyoub, et al., 2002], partially share such peptide binding properties. Screening the entire amino acid sequence of the SSX2 molecule with the SYFPEITHI algorithm for binding motifs for these DRB1 subtypes, we were able to identify one pentadecamer peptide that fulfills the criteria for a widely applicable HLA-DR restricted peptide vaccine.

Materials and Methods

The study had been approved by the local ethics review committee (Ethikkommission der Ärztekammer des Saarlandes) and was done in accordance with the declaration of Helsinki. Recombinant DNA work was done with the permission and according to the regulations of the local authorities (Regierung des Saarlandes).

Patients

Five healthy individuals and six patients with breast cancer were included in this study. All patients gave written informed consent. The breast cancer patients were studied at the time of operation and had not received chemo- or radiotherapy. HLA-DR typing was performed in 5/6 (including all responding) patients and in one of the five healthy controls who showed a T-cell response.

Cell Lines

The melanoma cell line SK-MEL-37 was kindly provided by Elisabeth Stockert (Ludwig Institute for Cancer Research (LICR), New York). SK-MEL-37 is positive for the HLA-DRB1 subtypes *0101 and *0301 and for DRB3 *0202. Me 275, which is homozygous for DRB1*1302 and for DRB3*0301, and Me 290, which expresses HLA-DRB1*0301, *1501, B3*0101 and B5*0101, were kindly provided by Daniel Speiser (LICR, Lausanne). All three cell lines express SSX2 and HLA-DR as determined by RT-PCR and immunocytology [dos Santos, et al., 2000], respectively. Cell lines were cultured in RPMI 1640/10% FCS, 2 mM L-glutamine and 1% penicillin/streptomycin (GIBCO, Invitrogen GmbH, Karlsruhe, Germany). Before used for T-cell assay, Me 275 and Me 290 were cultured for 48 h with 150 U/ml interferon-γ to increase their HLA-DR expression, which is considerably lower than that on SK-MEL-37 cells (data not shown). In addition to these three melanoma cell lines, allogeneic lymphoblastoid cell lines (LCL) were used to delineate more exactly the subtype-specific HLA-DR restriction of the T-cell responses under study. LCL were generated as described by our group previously [Kubuschok, et al., 2000].

Generation of Dendritic cells

Monocyte-derived dendritic cells (DC) were generated according to a protocol reported by others previously [Thurner, et al., 1999]. PBMC from patients or healthy controls were isolated from 60-70 ml EDTA blood by density gradient centrifugation with Ficoll-Paque™ Plus (Amersham Pharmacia Biotech AB, Uppsala, Sweden). CD14+ monocytes were separated by magnetic activated positive selection (MACS) with CD14+ microbeads (Miltenyi, Bergisch Gladbach, Germany) according to the manufacturer's instructions. $5 \times 10^6$ CD14$^+$ cells/1.5 ml were plated into the wells of a 6-well plate (Nunc GmbH & Co. KG, Wiesbaden, Germany) which had been coated with 10% human serum albumin in PBS. The cells were cultured for 16 h without cytokines in RPMI 1640/10% FCS, 2 mM L-glutamine and 1% penicillin/streptomycin (GIBCO). On days 1 and 3, 500 µl fresh medium containing GM-CSF (800 U/ml) and IL-4 (1,000 U/ml) were added to each well. On day 5 all non-adherent cells were collected and transferred into new 6-well plates at a concentration of $5 \times 10^5$ cells per 2 ml of cytokine-supplemented fresh medium, and the respective whole-protein antigens (SSX2 or NY-ESO-1) were added at a concentration of 10 µg/ml for incubation overnight. On day 6, TNF-α (10,000 ng/ml), IL-1β (10,000 ng/ml), IL-6 (1,000 U/ml) and prostaglandin E2 (1 µg/ml; Sigma, Taufkirchen, Germany) were added to induce full maturation. All cytokines were purchased from R&D Systems GmbH (Wiesbaden, Germany). On day 8, DC were harvested and used as antigen presenting cells (APC) in the ELISPOT assays at $1 \times 10^4$ cells per well. The stage of DC maturation was assessed by the reactivity of the DC with a panel of monoclonal antibodies as analyzed by flow cytometry using a FACScan (Becton-Dickinson, Heidelberg, Germany). Fully matured DC had the phenotype CD14$^-$, CD1a$^+$, CD83$^+$, CD86$^{+++}$, HLA-DR$^{+++}$ and MHC-I$^{+++}$ (data not shown).

Analysis of SSX2 mRNA Expression by Tumors

Fresh tumor biopsies were frozen within 15 min after surgical excision. The transcription of SSX2 mRNA was checked by RT-PCR, using conditions as described previously [Tureci, et al., 1996].

Prediction of HLA-Binding Peptides by the SYFPEITHI Algorithm

Peptides were derived on the basis of the previously published HOM-MEL-40/SSX2 sequence [Tureci, et al., 1996]. The SYFPEITHI algorithm (refer to the Institute for Cell Biology, Department of Immunology website for a database of MHC ligands and peptide motifs; Rammensee, et al., 1999) was used for the prediction of SSX2 peptides binding to the DRB1 subtypes *0101, *0301, *0401, *0711, *1101, and 1501. As a result we chose the following 3 peptides with a predicted high probability to bind to the six selected HLA-DRB1 molecules: p45-59 (KIFYVYMKRKYEAMT; SEQ ID NO:42), p60-74 (KLGFKATLPPFMCNK; SEQ ID NO:39) and p171-185 (RKQLVIYEEISDPEE; SEQ ID NO:41). The pan-DR binding epitope PADRE which has a high affinity to the six selected DRB1 subtypes [Alexander, et al., 1994] was chosen as a negative control. A mix of 7 peptides (p32, p117, p243, p269, p299, p520, and p524) derived from the pp65 antigen of the human cytomegalovirus (CMV) was used as a positive control. Except for PADRE, which consists of 13 amino acids, all peptides used in this study were 15 amino acid residues long. Peptides were synthesized following the Fmoc/tBu strategy as described [Zarour et al., 2002]. Purity was >90% as assessed by HPLC and mass spectrometry. All peptides were dissolved in a mixture of water and DMSO. The concentration for each peptide during pulsing was 2 µg/ml, resulting in a molarity of 0.9 µM for SSX2-derived p45-59, 1.03 µM for p60-74, and 0.95 µM for p171-185. The DMSO concentration during APC pulsing remained <1% (v/v).

In Vitro Stimulation of T-Cells with Peptides

PBMC from patients were isolated by Ficoll-Paque™ PLUS separation (Amersham Pharmacia Biotech AB, Uppsala, Sweden). For in-vitro priming, $1 \times 10^7$ and $2 \times 10^6$ unseparated PBMC, respectively, were suspended in 500 µl serum-free medium (X-Vivo 15 (Biowhittaker Europe s.p.r.l., Verviers, Belgium) supplemented with 2 mM L-glutamine (Gibco) and 1% penicillin/streptomycin (Gibco). For pulsing, the pool of the 3 SSX2-derived peptides (each at a concentration of 2 µg/ml) was added to the suspension of $1 \times 10^7$ cells, while the suspension of $2 \times 10^6$ PBMC was pulsed with the mix of 7 peptides (each at 2 µg/ml) derived from the pp65 antigen of the human CMV. Pulsing was performed for 90-120 minutes at 37° C. Thereafter the pulsed cells were washed once with serum-free medium and suspended for cultivation in X-Vivo 15 T-cell medium (Biowhittaker) supplemented with 10% human AB serum (Biowhittaker) and 6.7 ng/ml IL-7 (R&D systems). The $1 \times 10^7$ SSX2-pulsed PBMC were suspended in 3.75 ml T-cell medium and plated into 5 wells (0.75 ml/well) of a 48-well Nuncclone™ plate (Nunc GmbH & Co KG.). The $2 \times 10^6$ pp65-pulsed PBMC were plated into 1 well (0.75 ml). The remaining PBMC from the patients or donors, respectively, were divided into at least 3 aliquots of $1 \times 10^7$ PBMC and frozen until used for restimulation and in the T-cell assays. The peptide-pulsed PBMC which served both as APC and as a source for the T-cells to be used in the ELISPOT assay, were cultured at 37° C. One day after the stimulation was started, each well was supplemented with 250 µl X-Vivo 15 medium supplemented with 80 U/ml IL-2 (R&D Systems) resulting in a final concentration of 20 U/ml IL-2. The cells were incubated for 6 days under occasional microscopic control. On day 7 and before each ELISPOT assay, respectively, the percentage of CD4$^+$ T-cells in the culture well was determined. On day 7, cells were restimulated with autologous PBMC that had been pulsed with the appropriate peptides under the same conditions as described for day 0/1 at a CD4$^+$/APC ratio of 1:1. On day 14, the first ELISPOT assay was performed. To this end, the cultured cells were harvested from the respective wells and the primed CD4$^+$ cells were used as effectors in the ELISPOT assay. The remaining cells were restimulated once more using conditions as described before. Unless no specific reactivity was shown by day 21, the stimulation was repeated weekly until all CD4$^+$ cells were consumed.

ELISPOT assay

At least three IFN-γ ELISPOT assays were performed on days 14, 21 and 28, respectively. All tests were run in triplicates in order to determine mean values and standard deviations. Assays were performed in nitrocellulose-lined 96-well plates (MAHA S45 by Millipore, Bedford Mass., USA). The wells were pre-coated overnight with PBS (50 μl/well) containing an anti-IFN-γ capture antibody at the dilution recommended in the supplier's instructions (Mabtech AB, Nacka, Sweden). To block unspecific binding, the wells were then incubated with 10% human AB+ serum for 1 h at 37° C. For the priming of effector cells, $2.5 \times 10^4$ CD4+ T-cell were harvested, washed once to remove the cytokines, and were tested for specific recognition of the corresponding antigen. To this end, peptide-primed CD4+ cells were harvested, washed once to remove cytokines, resuspended, and 50 μl of the cell suspension in X-Vivo 15 medium were added to each well.

Four different kinds of APC were used: $1^{st}$, autologous or allogeneic PBMC pulsed with the appropriate peptides as described before, irradiated with 60 Gray (Gy), washed and resuspended at $5 \times 10^4$ cells per 50 μl and well; $2^{nd}$, autologous or allogeneic DC either antigen-pulsed or additionally pulsed with the respective peptides, irradiated with 60 Gy, washed and resuspended at $1 \times 10^4$ per 50 μl and well; $3^{rd}$, allogeneic LCL pulsed with the appropriate peptides as described above, irradiated with 120 Gy, washed and resuspended at $2 \times 10^4$ cells per 50 μl and well; $4^{th}$, allogeneic cells from melanoma cell lines either untreated or pulsed with the respective peptides as described before, irradiated with 120 Gy, washed and suspended at $3 \times 10^4$ cells per 50 μl and well. Effector cells and APC were coincubated for 14-16 h at 37° C.

To prove the DR restriction of the respective T-cell responses, the T-cell receptor/MHC-II interaction was blocked using antibodies against HLA-DR (clone L243), HLA-DP (clone B7/21; both from Becton Dickinson GmbH), anti-pan MHC-II (clone WR18 from SEROTEC, Biozol Diagnostica Vertrieb GmbH, Eching, Germany) and anti-pan MHC-I (clone W6/32 from DaKoCytomation, Hamburg, Germany). For blocking with the appropriate antibody, the APC were suspended in 100 μl pure X-Vivo 15 medium and incubated with the respective antibody (5 μg/ml) for 30 min at 4° C. The APC were washed and resuspended in 150 μl X-Vivo 15 medium. None of the antibodies exhibited any cytotoxic activity at the concentrations used for the blocking experiments, as demonstrated by the absence of inhibition of MHC-I mediated T-cell responses by L243, B7/21, WR18, and SK3, and of MHC-II mediated T-cell responses by W6/32 (data not shown).

For the visualization of the T-cell reaction, the supernatants were removed from the wells and the plates were washed thoroughly. Then 50 μl of the biotinylated IFN-γ detection antibody (Mabtech AB, Nacka, Sweden) diluted 1:1000 in PBS were added to each well. The plates were incubated for 2 h at 37° C. Again plates were washed thoroughly. To enhance the sensitivity of the IFN-γ detection, plates were then incubated for 1 h with alkaline phosphatase conjugated streptavidin (Roche Diagnostics GmbH, Mannheim, Germany) diluted 1:2000 in PBS. After a final thorough washing, the IFN-γ spots were stained using the AP Conjugate Substrate Kit (BIO-RAD laboratories, Hercules Calif., USA) according to the manufacturer's instructions. The numbers of spots were counted using the BIOREADER-3000 Pro (BIO-SYS, Karben, Germany).

Detection of Serum Antibodies Against SSX2

Serum antibodies against HOM-MEL-40/SSX2 were assessed semi-quantitatively by using RAYS as described previously [Mischo, et al., 2003].

Identification of an HLA-DR Binding Epitope.

With the goal of developing an SSX2-derived MHC-II peptide vaccine for a broad spectrum of patients we aimed at identifying peptides with a promiscuous binding pattern for different HLA-DRB1 subtypes. We used the SYFPEITHI algorithm to identify SSX2 peptides with a high binding affinity score for HLA-DRB1 molecules that have a high prevalence in the Caucasian population. This is the case with the DRB1 subtypes *0101, *0301, *0401, *0701, *1101 and *1501 which are expressed by the majority of the Caucasian population.

SYFPEITHI predicted the following 3 peptides derived from SSX2 protein to have a high binding probability: p45-59, p60-74 and p171-185 (Table II). These peptides were synthesized and used for the stimulation of PBMC from unselected breast cancer patients and healthy controls. All patients and healthy controls were tested for all three peptides. All patients with a positive response were tested again between 3 months and one year after the initial analysis and persistence of the T-cell reactivity was confirmed in all cases.

TABLE II

HOM-MEL40/SSX2 derived peptides selected for this study.

| Antigen | Sequence | SEQ ID NO | Position | Binding probability to HLA-DRB1 . . . | | | | | |
|---------|----------|-----------|----------|-------|-------|-------|-------|-------|-------|
|         |          |           |          | *0101 | *0301 | *0401 | *0701 | *1101 | *1501 |
| SSX2    | KIFVYMKRKYEAMT | 42 | p45-59 | 18 | 8 | 16 | 10 | 24 | 0 |
|         | KLGFKATLPPFMCNK | 39 | p60-74 | 25 | 10 | 16 | 26 | 10 | 16 |
|         | RKQLVIYEEISDPEE | 41 | p171-185 | 13 | 18 | 8 | 14 | 6 | 26 |
| pp65    | PLKMLNIPSINVHHY | 45 | p117-131 | 28 | 14 | 26 | 30 | 12 | 24 |
|         | Frequency (%) |    |        | 8.7 | 10 | 8 | 11.7 | 8.3 | 12.1 |

*Indicated are the scores obtained by epitope prediction using the SYFPEITHI [Rammensee, et al., 1999] database. For comparison, the scores of a promiscuous DR-epitope out of the pp65 antigen from the human CMV are shown.

T-cell Responses.

All healthy controls and patients but one (BC401) responded to the CMV-derived peptides and all these responses could be blocked by competition with PADRE, confirming that PADRE binds to the respective HLA-DR subtypes.

No reproducible T-cell responses were observed after stimulation with the SSX2 peptides p60-74 and p171-185, respectively. In contrast, peptide p45-59 proved to be strongly immunogenic. The T-cells from 3/6 (50%) patients (BC355, BC400, and BC403) showed a response upon stimulation with p45-59. In addition, 1/5 (20%) healthy controls (Co17) showed a response upon stimulation with p45-59 (FIG. 4).

Demonstration of HLA-DR Restriction.

Figure 5:
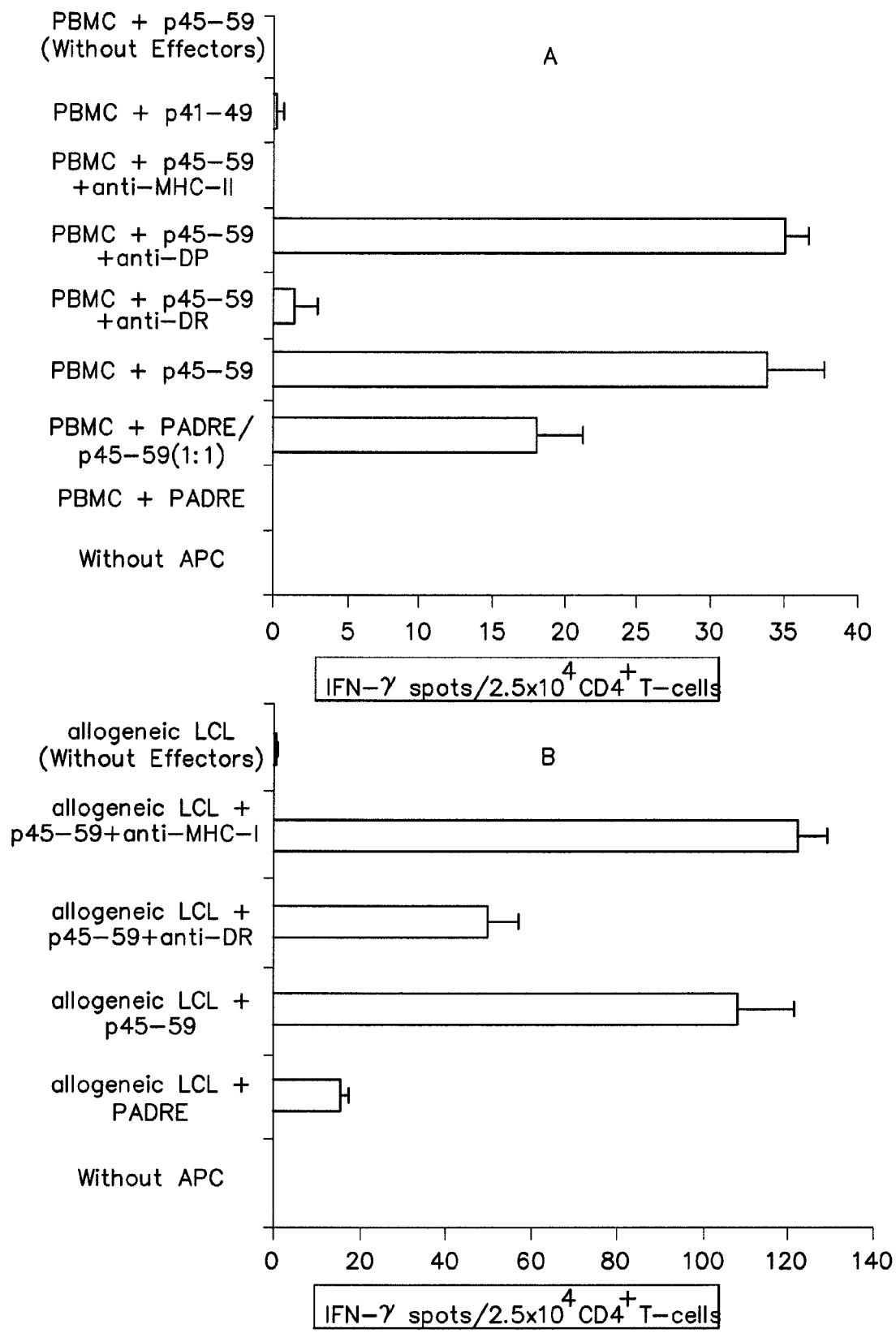
FIG. 5 shows HLA-DR restriction of the T-cell response against the HOM-MEL-40/SSX2 derived peptide p45-59.

The HLA-DR restriction of the reactivity to p45-59 was suggested by the decreased numbers of spots in the ELISPOT assay when the APC were pulsed with a 1:1 mixture of the pan DR-binding peptide (PADRE) and p45-59 peptide compared to pulsing with p45-59 alone. Definite evidence for the DR restriction of the T-cell response against SSX2-derived p45-59 was obtained by blocking the response with an HLA-DR antibody. Restriction by HLA-DP was excluded by demonstrating that the anti-HLA-DP antibody did not interfere with this response. Similarly, blocking with the MHC-I antibody W6/32 had no influence on the reaction (FIG. 5A). A cross-reaction with the HLA-A2 binding peptide p41-49 was also excluded by demonstrating that T-cells primed with p45-59 did not respond to p41-49.

Natural Processing and Presentation of HOM-MEL-40/SSX2 Derived p45-59.

Figure 6B:
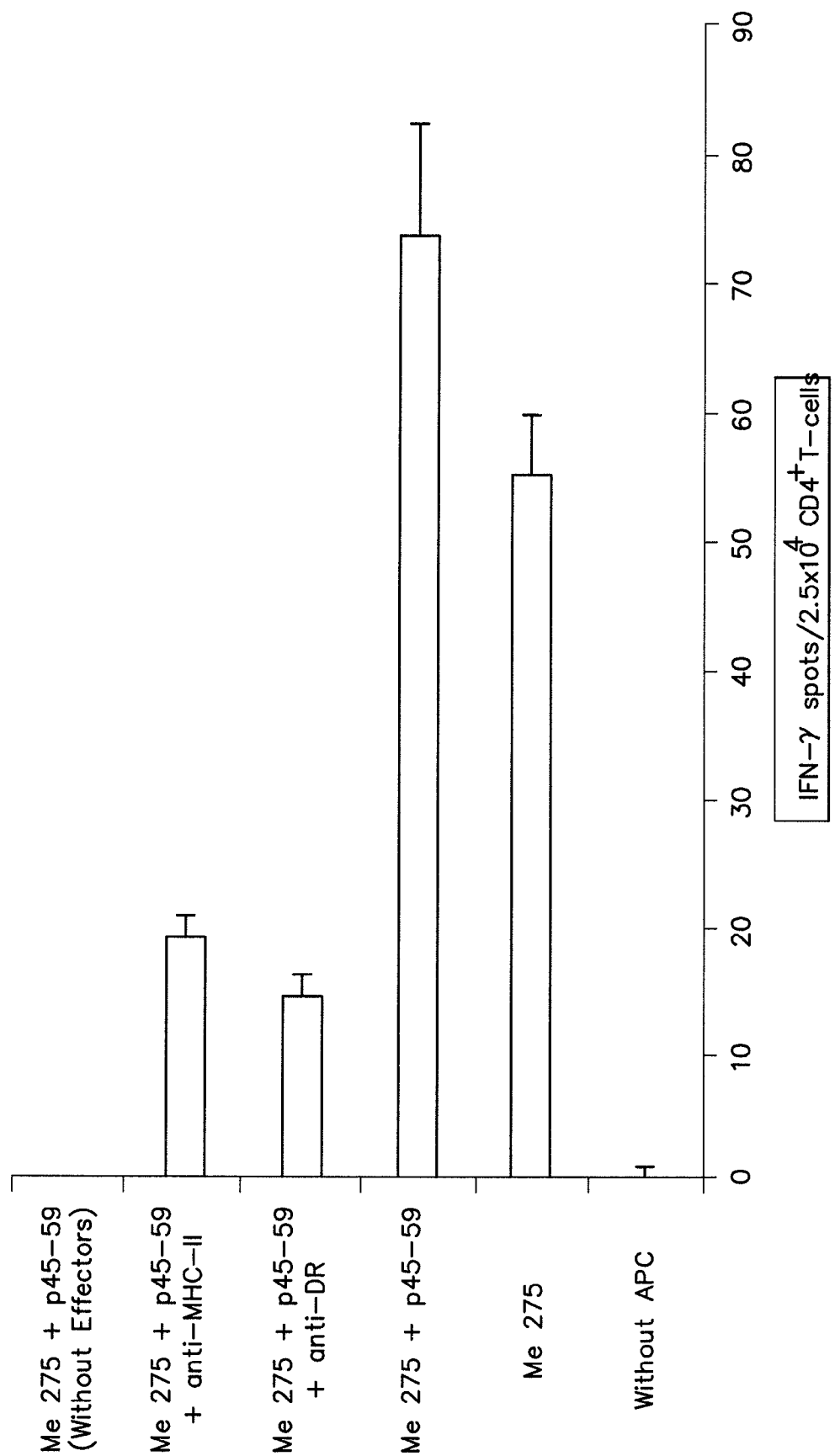
FIG. 6B: IFN-γ response of T-cells from patient BC355 primed with the HOM-MEL-40/SSX2 derived epitope p45-59 after challenge with the SSX2 expressing melanoma-derived cell line Me 275. Effector T-cells from patient BC355 and the melanoma cell line Me 275 share the HLA-DR subtypes B1*1302 and B3*0202 demonstrating that the T-cell response in this experiment is mediated by either B1*1302 or B3*0202.

To demonstrate the natural processing and presentation of p45-59, T-cells that had been prestimulated with the peptide p45-59 were challenged with autologous and allogeneic dendritic cells pulsed with whole-protein SSX2 and whole-protein NY-ESO-1 as a control. As can be seen from FIG. 6A, autologous and allogeneic dendritic cells loaded with whole-protein SSX2 induced a significant T-cell response which could be enhanced by the admixture of the peptide p45-59 used for sensitization. Moreover, when the cell line Me 275 was used instead of DC, a similar picture emerged (FIG. 6B), indicating that p45-59 is naturally processed by these cells.

Determination of HLA-DRB1 Subtypes Expressed by Reactive T-cells.

To further delineate the HLA-DR restriction of the SSX2-derived peptide p45-59, the HLA-DR subtype of all six patients and of 2/5 healthy controls (including the responding healthy control) were determined by HLA-SSP PCR. As can be seen from Table III, reactivity to the SSX2 epitope p45-59 was associated with the HLA-DRB1 subtypes *0701, *1101, *1302, and with B3*0301. This indicates that the observed T-cell reactivity was mediated by the following HLA-DR subtypes: 1st, DRB1*0701, 2nd DRB1*1101, and 3rd B1*1302 and/or B3*0301. Between B1*1302 and B3*0301 cannot be distinguished because they are always strictly linked. The restriction of the patient BC403 was more difficult to delineate. Since T-cells did not respond to Me 290 cells, that share the B1*1501 and B5*0101 subtypes, respectively, with patient BC403, the restriction by these HLA-DR subtypes can be excluded (Table IV). Therefore, the T-cell response of patient BC403 is most likely mediated by HLA-DRB1*1314 and/or B3*0202 (which is strictly linked with the former), but due to the lack of APC (cell lines or LCL) expressing these subtypes, we could not definitely establish the restriction of the observed T-cell response.

TABLE III

HLA-DR configuration, SSX2-expression and anti SSX2 serology from breast cancer patients (BC) and healthy controls (Co) analyzed this study.

| | HLA-DR | | | | | SSX2-expression | SSX2-serology | Response to p45-59 |
|---|---|---|---|---|---|---|---|---|
| | B1 | B1 | B3 | B4 | B5 | | | |
| BC355 | *0701 | *1302 | *0301 | *0101 | — | + | — | + |
| BC388 | *0402 | *1601 | — | *0103 | *0202 | + | — | — |
| BC399 | *0101 | *0701 | — | *0101 | — | + | — | — |
| BC400 | *0701 | *1302 | *0301 | *0103 | — | + | — | + |
| BC401 | *0403 | *1102 | *0202 | *0103 | — | — | — | — |
| BC403 | *1314 | *1501 | *0202 | — | *0101 | + | — | + |
| Co17 | *0701 | *1101 | *0202 | *0103N | — | — | — | + |
| Co70 | | | n.d. | | | — | — | — |
| Co71 | | | n.d. | | | — | — | — |
| Co72 | | | n.d. | | | — | — | — |
| Co73 | *0801 | *1201 | *0202 | — | — | — | — | — |

TABLE IV

Dissection of the DR restriction of the T-cell response against p45-59.

| p45-59 stimulated effector T-cells | | | | T-cell response | APC | | | |
|---|---|---|---|---|---|---|---|---|
| BC355 | HLA-DRB1* | 0701 | 1302 | Yes | 0401 | 0701 | HLA-DRB1* | LCL 40 |
| | B3* | — | 0301 | | — | — | B3* | |

TABLE IV-continued

Dissection of the DR restriction of the T-cell response against p45-59.

| | p45-59 stimulated effector T-cells | | | T-cell response | APC | | | |
|---|---|---|---|---|---|---|---|---|
| | B4* | 0101 | — | | | 0103 | B4* | |
| | HLA-DRB1* | 0701 | 1302 | Yes | | 1302 | HLA-DRB1* | Me 275 |
| | B3* | — | 0301 | | | 0301 | B3* | |
| | B4* | 0101 | — | | | — | B4* | |
| BC403 | HLA-DRB1* | 1314 | 1501 | No | 0301 | 1501 | HLA-DRB1* | Me 290 |
| | B3* | 0202 | — | | 0101 | — | B3* | |
| | B5* | — | 0101 | | — | 0101 | B5* | |
| Co17 | HLA-DRB1* | 0701 | 1101 | Yes | | 1101 | HLA-DRB1* | LCL 7 |
| | B3* | — | 0202 | | | 0202 | B3* | or |
| | B4* | 0103N | — | | | — | B4* | DC 7 |
| | HLA-DRB1* | 0701 | 1101 | Yes | 0401 | 0701 | HLA-DRB1* | LCL 40 |
| | B3* | — | 0202 | | — | — | B3* | |
| | B4* | 0103N | — | | | 0103 | B4* | |
| | HLA-DRB1* | 0701 | 1101 | No | 0101 | 0301 | HLA-DRB1* | SK-MEL- |
| | B3* | — | 0202 | | — | 0202 | B3* | 37 |
| | B4* | 0103N | — | | — | — | B4* | |

Correlation of MHC-II Restricted T-cell and Humoral Anti-HOM-MEL-40/SSX2 Antibody Responses.

None of the six patients tested for a T-cell response against the HOM-MEL-40/SSX2 derived epitope p45-59 had anti-HOM-MEL-40/SSX2 serum antibodies as determined by recombinant antigen expression on yeast surface (RAYS) and none of the five healthy controls was HOM-MEL-40/SSX2 seropositive. Thus, no association between "T-cell responders" against p45-59 and "antibody responders" could be established for these subjects.

Discussion

The reported frequent expression of HOM-MEL-40/SSX2 in a broad range of tumors makes this cancer-testis antigen a potentially interesting target for immunotherapy of a broad spectrum of malignancies. The HOM-MEL-40/SSX2 gene was cloned from a melanoma-derived cDNA library expressed in E. coli that was shown to code for an antigen detectable by high-titered IgG antibodies in the autologous serum from the melanoma patient. High-titered IgG antibodies imply cognate T-cell help; therefore the approach of reverse T-cell immunology should be most promising in patients with high-titered IgG serum antibodies in the respective serum. However, due to the paucity of patients presenting with limited-stage breast cancer (except for patient BC355 who had skin metastases, none had metastatic disease) and having detectable anti-SSX2 antibody levels in their serum, we could not restrict our study to such patients. Nevertheless, we succeeded in demonstrating for the first time that MHC-II restricted responses against SSX2 can be induced in cancer patients, supporting the general concept that $T_H1$ (i.e. interferon-γ producing) T-cell responses can be demonstrated against antigens that are originally detected by their potential to induce a humoral immune response.

We used the SYFPEITHI algorithm for an in silico screening of the entire SSX2 protein for peptides with HLA-DR peptide motifs. Making use of the anchor positions shared by the HLA-DRB1 subtypes *0101, *0301, *0401, *0701, *1101, and *1501 we searched for SSX2 peptides with binding motifs suggesting a promiscuous binding to several subtypes. Of the 3 peptides predicted to fulfill this prerequisite with a high binding score in the SYFPEITHI algorithm, two peptides (p60-74 and p171-185) failed to induce reproducible T-cell responses. Several reasons might be responsible for this failure: the binding scores for the peptides p60-74 and p171-185 are in general inferior compared to the epitope p45-59, and/or natural processing might not occur.

In contrast to p60-74 and p171-185, the SSX2-derived epitope p45-59 induced T-cell responses in 3/6 (50%) breast cancer patients and 1/5 (20%) healthy controls tested. The analysis of the HLA typing of the responding individuals and of the melanoma-derived cell lines and LCL used in this study reveal that the responses against p45-59 are mediated by the DRB1 subtypes *0701, *1101 and B1*1302/B3*0301. While SYFPEITHI would have predicted a high-binding affinity for *1101, this is not the case for 0701. Similarly, B1*1302/B3*0301 is not yet considered in the SYFPEITHI data base. On the other hand, while SYFPEITHI predicts a high binding affinity of the HLA-DRB1 subtypes *0101 and *0401, none of the responding patients expressed the HLA-DRB1*0401 subtype and one patient with the *0101 subtype did not respond to p45-59.

p45-59 mediates a promiscuous binding to at least three HLA-DR subtypes that are expressed by a considerable proportion of the Caucasian population. Other human tumor-associated antigens for which antigenic peptides with limited promiscuity for different HLA-DR subtypes have been reported include HER2/neu [Kobayashi, et al., 2000] and MAGE-A3 [Romero, et al. 2001] and NY-ESO-1 [Zarour, et al., 2003; Mandic, et al., 2003].

Our strategy of "reverse T-cell immunology" for the identification of MHC-II binding peptides of HOM-MEL-40/SSX2 was not restricted to individuals selected for HLA-DR subtypes with a high binding affinity to the respective peptide predicted by the SYFPEITHI algorithm. Because the SYFPEITHI score does not cover all known HLA-DR subtypes, we preferred to test an unselected series of patients and healthy controls and define the MHC-II subtypes a posteriori in individuals demonstrating a T-cell reactivity against the respective peptide. This approach is retrospectively justified by our finding of a T-cell response mediated by HLA-DRB1*1302, which is not yet considered in the SYFPEITHI database. The amino acid sequence of HLA-DRB1*1302 makes it evident that the amino acid G at the position 86 in contrast to V in the case of DRB1*1301 provides a large pocket for a p1 anchor with preference for Y and W (IMGT/HLA database of the EMBL-European Bioinformatics Institute). The assumption that p45-49 uses Y48 as a p1 anchor for binding to HLA-DRB1*0701 and *1101 also suggests a high binding affinity to *1302.

There are other approaches of "reverse T-cell immunology" that can be pursued for the identification of CD4⁺ T-cell stimulating peptides derived from a tumor-associated antigen. One such strategy, employed by Jäger et al. (2000), is to synthesize and test overlapping peptides that cover the whole antigenic protein. This approach, if applied to the analysis of the T-cell response of patients, is hindered by the enormous amounts of cells necessary from a given patient to test the entire battery of peptides. However, as shown in the Examples above, this approach can be used successfully to identify the same or similar peptides as identified by the present method. To narrow down the spectrum of candidate peptides, screening of HLA-DR transgenic mice might be helpful [Zeng, et al., 2002]; however the respective transgenic mice are not commonly available. In this study we followed a different strategy to narrow down the number of SSX2-derived peptides with putative DR-reactivity.

The SSX2 derived peptide p45-59 is partially overlapping with the p41-49 epitope, which has previously been shown to bind to HLA-A*0201 [Ayyoub, et al., 2002; Ayyoub, et al., 2003]. However, T-cells presensitized with p45-59 did not respond to a challenge with p41-49 not even in the context of HLA-A*0201 nor in the context of the HLA-DR subtypes examined in this study, indicating that no cross-reactivity exists between the two peptides. Moreover, treatment of APC from Col7 with anti-pan MHC-I antibody (clone W6/32) did not influence the T-cell response against p45-59 excluding an MHC-I mediated CD8$^+$ T-cell reaction against p45-59 (FIG. 5B).

While the in silico prediction of the potential HLA class-II ligand from any protein sequence based on the identification of appropriately positioned anchor residues specific for a given HLA class-II allele [Rammensee, et al., 1999] allows for the identification of peptides with high binding affinity, many such peptides were shown not to be presented by tumors as demonstrated by the poor recognition of cells expressing the corresponding protein of interest endogenously [Valmori, et al., 1999; Zaks and Rosenberg, 1998; Ayyoub, et al., 2001]. Hence a crucial step for the application of reverse T-cell immunology is the demonstration that the generated T-cell lines can recognize target cells expressing the antigenic protein. The natural processing and presentation of p45-59 was proven by demonstrating that T cells prestimulated with p45-59 recognized both autologous and allogeneic dendritic cells pulsed with the whole HOM-MEL-40/SSX2 protein as well as Me275, a cell line that endogenously expresses HOM-MEL-40/SSX2 and presents it in the context of HLA-DRB1*1302 and B3*0301 as shown by specific blocking of the response by anti-pan-HLA-DR antibody. Thus, p45-59 fulfills all requirements for a CD4$^+$ T-cell stimulating vaccine of patients with a HOM-MEL-40/SSX2-positive cancer.

After NY-ESO-1 [Jager, et al., 2000; Zarour, et al., 2002; Zarour, et al., 2000; Zeng, et al., 2000; Zeng, et al., 2001; Zeng, et al., 2002; Neumann, et al., 2003], SSX2 is now the second of the human CTA originally identified by SEREX, for which both CD8$^+$ and CD4$^+$ T-cell as well as humoral immune responses have been demonstrated. This proves that using SEREX followed by "reverse T-cell immunology" is a straight-forward and successful approach not only for the identification and molecular definition of antigens that are immunogenic in cancer patients, but also for the determination of MHC-I and MHC-II restricted peptide fragments of the respective antigens. Taking NY-ESO-1 and HOM-MEL-40/SSX2 as precedents, the successful definition of both MHC-I and MHC-II binding peptides derived from additional SEREX-defined antigens can be expected.

Example 7

Confirmation of Additional SSX-2 Peptide Recognized by Several HLA-DR Haplotypes The methods described above were used to test the binding of SSX-2 peptides p98-112 and p101-115 (SEQ ID NO:40 and SEQ ID NO:43, respectively). For SSX-2 peptide p98-111, binding was demonstrated to DRB1*0101, DRB1*1101, DRB1*1501, DRB3*0202 and/or DRB5*0101. For SSX-2 peptide p101-115, binding was demonstrated to DRB1*0701, DRB1*0301 and/or DRB3*0202.

Example 8

Materials and Methods

Isolation of SSX-2 Specific CD4$^+$ T Cell Clones, Cells and Tissue Culture.

SSX-2 specific CD4$^+$ T cells were isolated from previously generated cultures from melanoma patients (Ayyoub M, et al., J Clin Invest., 2004; 113 (8): 1225-33) stimulated in vitro with peptide SSX-2 37-58 (SEQ ID NO:10). CD4+ T cells secreting cytokines following peptide stimulation were isolated by cytokine guided magnetic cell sorting using the cytokine secretion detection kit (Miltenyi Biotec, Auburn, Calif., USA) and cloned by limiting dilution culture in the presence of phytohemagglutinin (PHA) (Sigma, St Louis, Mo.), allogeneic irradiated PBMC and recombinant human (rh)IL-2 as described (Valmori D, et al., Cancer Res., 2000; 60: 4499-506). Clones were subsequently expanded by periodic (3-4 weeks) stimulation under the same conditions. Melanoma cell lines and anti HLA-DR (D1.12) and -DP (B7.21.3) antibodies were provided by Dr. D. Rimoldi. Cell lines were maintained in RPMI 1640 (GIBCO, Rockville, Md.) supplemented with 10% heat inactivated fetal calf serum (FCS) (Sigma). Homozygous EBV transformed cell lines were obtained from The National Marrow Donor Program (NMDP) and the American Society for Histocompatibility and Immunogenetics (ASHI) Cell Repository (refer to the American Society for Histocompatability and Immunogenetics (ASHI) website). The NMDP/ASHI Cell Repository is supported by funding from the Office of Naval Research and the American Society for Histocompatibility and Immunogenetics.

Antigen Recognition Assays.

For intracellular cytokine secretion detection, T cells were stimulated in the absence or in the presence of peptides at the indicated dose during 4 h as described previously (Ayyoub M, et al., J Clin Invest., 2004; 113 (8): 1225-33, see examples above). One hour after the beginning of the incubation, Brefeldin A (10 mg/ml, Sigma) was added to inhibit cytokine secretion. After incubation, cells were stained with anti-CD4 mAb (BD Biosciences, San Diego, Calif.) for 20 min at 4° C. and fixed using formaldehyde, permeabilized with saponine (Sigma, 0.1% in PBS 5% FCS), stained with anti IFN-γ mAb (BD Biosciences) and analyzed by flow cytometry. Data analysis was performed using Cell Quest software. IFN-γ secretion was assessed as described (Ayyoub M, et al., J Clin Invest., 2004; 113 (8): 1225-33). T cells (10,000/well) and EBV transformed B cells (EBV) used as antigen-presenting cells (APC, 10,000/well) were incubated in the absence or in the presence of peptides at the indicated dose in 96-well round-bottom plates in 200 ml/well of medium. In some experiments tumor cells were used as APC. Where indicated, tumor cells were transiently transfected with SSX-2 cDNA, cloned into pcDNA3.1 vector, using FuGENE according to the manufacturer's instructions (Roche Diagnostics, Indianapolis, Ind., USA). After 24 h incubation at 37° C., culture supernants were collected and the content of IFN-g determined by ELISA (BioSource International, Camarillo, Calif., USA).

Recombinant proteins and tumor lysates.

SSX-2 protein was expressed in *Escherichia coli* as full-length protein with a six-histidine tag at the amino terminus (Stockert E, et al., J. Exp. Med., 1998; 187 (8): 1349-54). The protein was purified from solubilized inclusion bodies by nickel chelate affinity chromatography (Chelating Sepharose FF; Amersham Pharmacia Biotech) by using a pH gradient and eluted in 8 M urea, 100 mM phosphate, and 10 mM Tris at pH 4.5. The purified protein was reactive with anti-SSX-2 monoclonal antibodies by Western blot analysis; purity was >80% by SDS/PAGE. Where indicated, APC were incubated with proteins for 12 hours and washed prior to their use in antigen recognition assays.

Results

Isolation of SSX-2 Specific CD4+ T Cells from SSX-2 37-58 Peptide Stimulated Cultures from HLA-DR11 Negative Melanoma Patients.

Figure 7A:
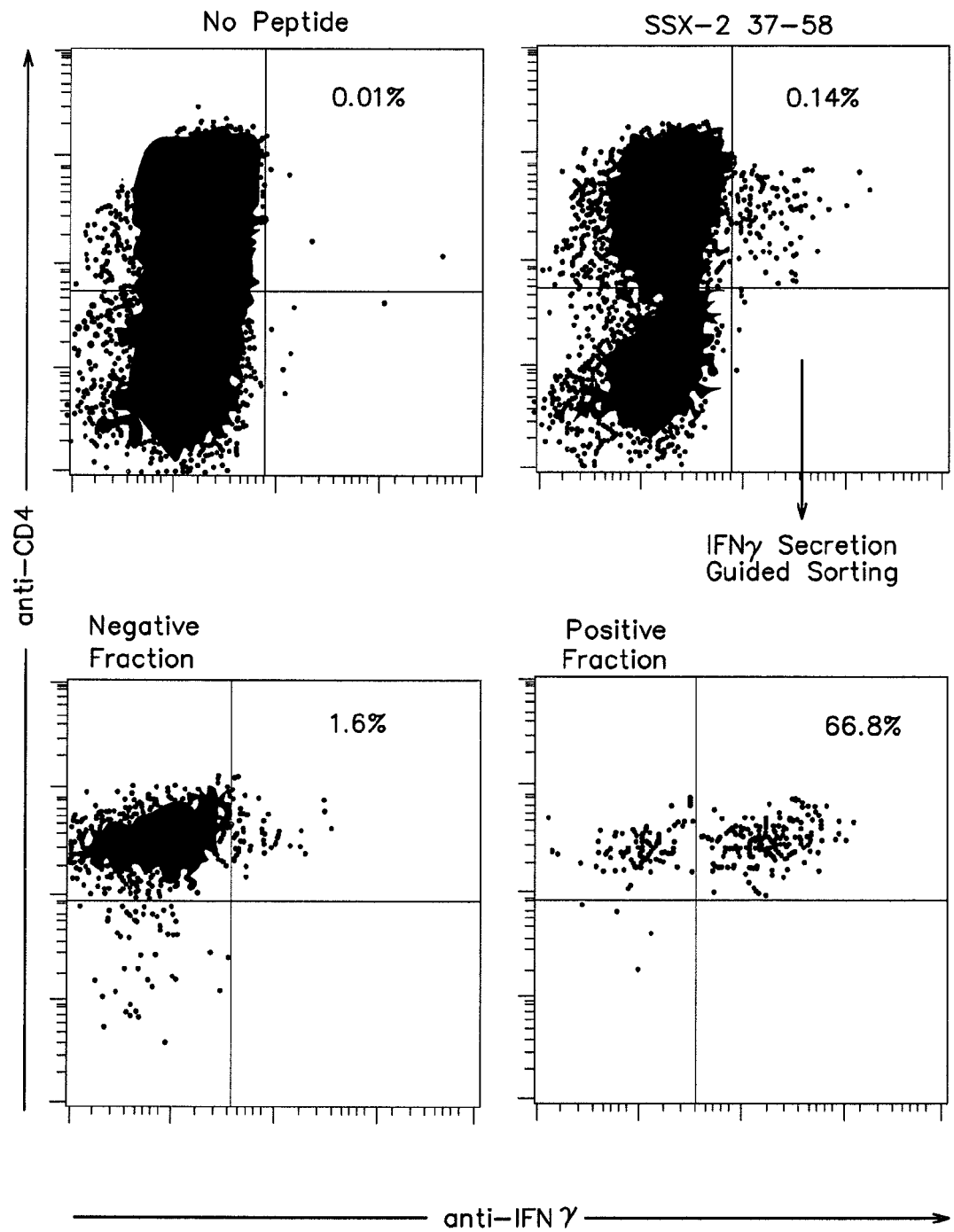
FIG. 7 shows isolation of SSX-2 specific CD4+ T cells from SSX-2 37-58 peptide stimulated cultures from HLA-DR11 negative melanoma patients, assessment of HLA-DR restriction and identification of the restricting allele. (A) The presence of specific CD4+ T cells in the cultures was assessed by intracellular staining with anti-IFN-g mAb after incubation in the absence or in the presence of peptide, as indicated.

We have recently reported the identification of an SSX-2 derived T cell epitope located in the 45-59 region of the protein and recognized by CD4+ T cells from melanoma patients in association with HLA-DR11 (Ayyoub M, et al., J Clin Invest., 2004; 113 (8): 1225-33, see also examples above). The epitope was initially identified as the target of SSX-2 specific CD4+ T cells isolated from an HLA-DR11+ melanoma patient bearing an antigen-expressing tumor. CD4+ T cells were isolated from PBMC stimulated in vitro with autologous monocyte-derived DC loaded with SSX-2 recombinant protein followed by screening with a pool of partially overlapping peptides spanning the entire SSX-2 protein sequence (Ayyoub M, et al., J. Immunol., 2002; 168 (4): 1717-22). One peptide in the pool, SSX-2 37-58, was initially identified as the active peptide and used to assess responsiveness in melanoma patients and healthy donors (Ayyoub M, et al., J Clin Invest., 2004; 113 (8): 1225-33). Interestingly, in addition to HLA-DR11 positive responder patients, 2 HLA-DR11 negative patients bearing SSX-2 expressing tumors responded to in vitro stimulation with peptide SSX-2 37-58. With the aim of identifying the epitope(s) recognized by CD4+ T cells from these patients, SSX-2 37-58 reactive cells were isolated from the peptide stimulated cultures of patients LAU 233 and LAU 331 by cytokine secretion guided magnetic cell sorting (FIG. 7A and not shown) and cloned under limiting dilution conditions as described previously (Valmori D, et al., Cancer Res., 2000; 60: 4499-506). We obtained several clones that were used to characterize the epitope in terms of HLA class II restriction and fine specificity of antigen recognition.

Assessment of HLA-DR Restriction and Identification of the Restricting Allele.

Figure 7B:
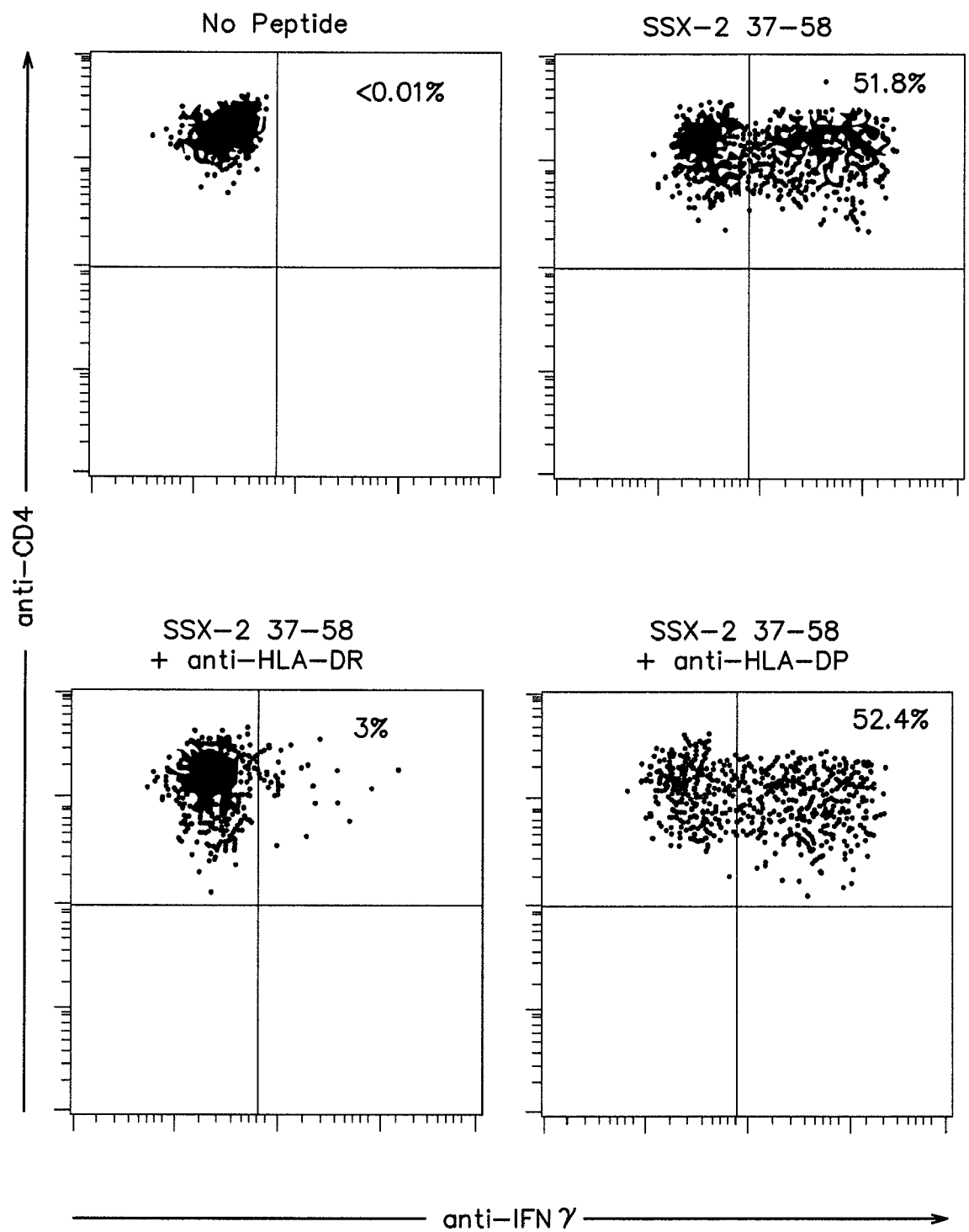
Figure 7C:
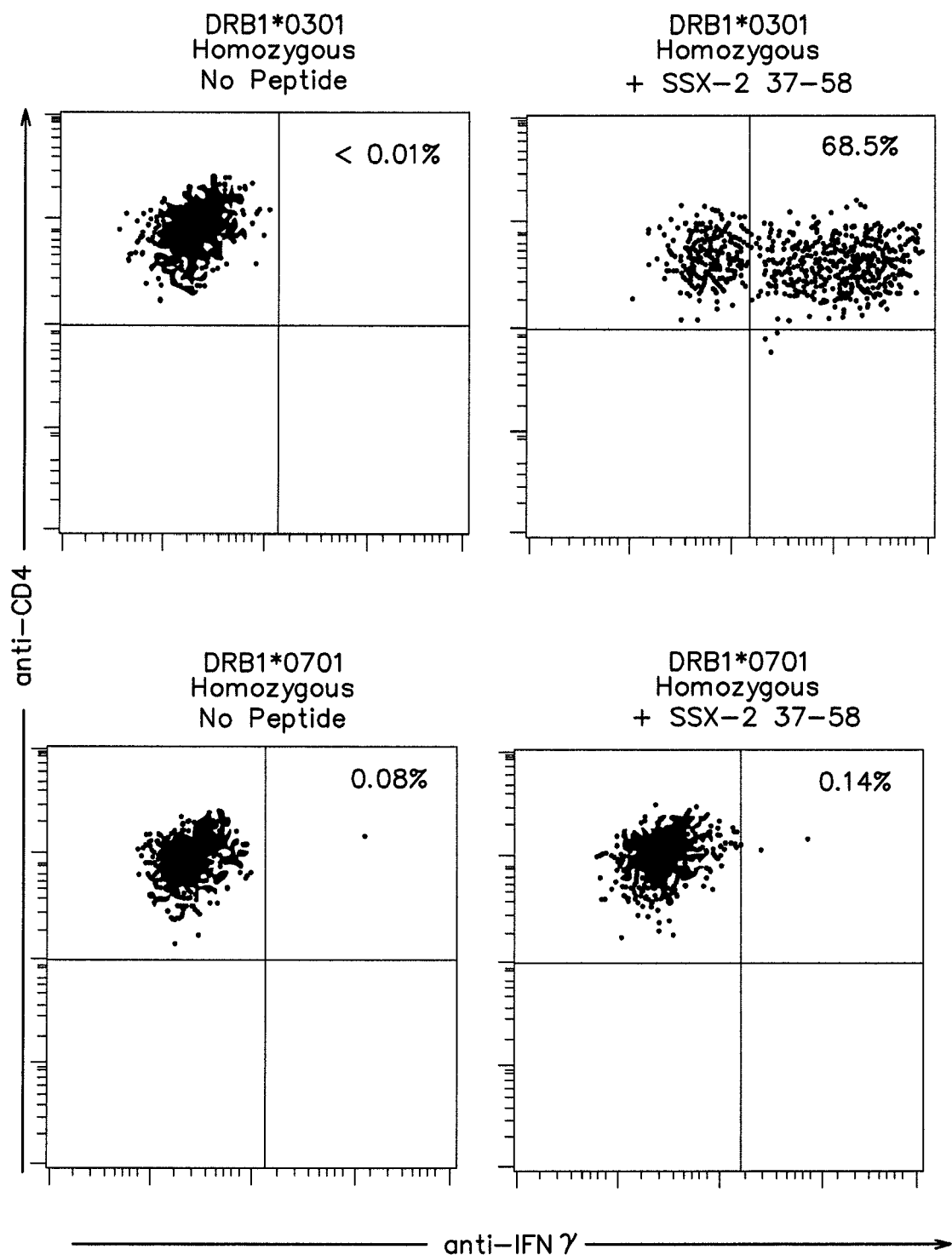

To identify the MHC class II restricting element used by SSX-2 37-58 specific CD4+ T cells from patients LAU 233 and LAU 331, peptide presentation experiments were performed in the presence of antibodies that block the recognition of antigens restricted by different MHC Class II molecules. Anti-HLA-DR antibodies almost completely inhibited antigen recognition, whereas no inhibition was observed in the presence anti-HLA-DP antibodies (FIG. 7B). Similar results were obtained for other clones from LAU 331 and LAU 233. Molecular typing of patients' PBMC revealed that both expressed HLA-DRB1*0301 and DRB1*0701 alleles. To identify the presenting allele we assessed the ability of peptide pulsed HLA-DRB1*0301 or DRB1*0701 homozygous EBV to present the antigen to specific clonal populations (FIG. 7C). Efficient presentation was obtained using the DRB1*0301 homozygous EBV (COX) whereas no significant presentation was observed with the DRB1*0701 homozygous EBV (BH). It is noteworthy that both LAU 331 and LAU 233 expressed two additional HLA-DR alleles, DRB3*0101 and DRB4*0101. Presentation through DRB4*0101 was excluded as this allele was also expressed by the DRB1*0701 homozygous EBV cell line BH that was unable to present the peptide. Presentation through DRB3*0101 was also excluded as no presentation was obtained using the homozygous EBV cell line 0MW (DRB1*1301, DRB3*0101, not shown).

Mapping of the Epitope Recognized by SSX-2 Specific DRB1*0301-Restricted CD4+ T Cells.

Figures 8A, 8B:
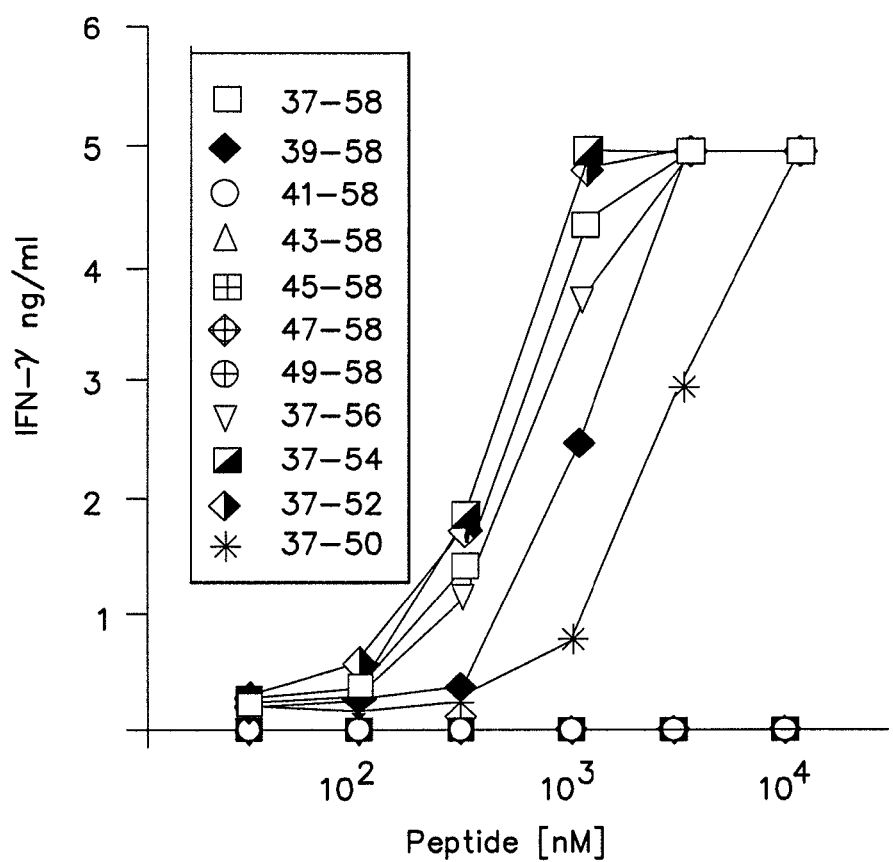

To define the SSX-2 derived peptide recognized by DRB1*0301 restricted specific CD4+ T cells, we initially searched the sequence of the peptides that, in this region of the protein, are predicted to optimally bind to DRB1*0301 using the SYFPEITHI prediction program developed by H-G Rammensee and colleagues (Rammensee H, et al., Immunogenetics, 1999; 50 (3-4): 213-9), (refer to the Institute for Cell Biology, Department of Immunology website for a database of MHC ligands and peptide motifs). Two peptides in the SSX-2 37-58 region were identified as having high DRB1*0301 binding potential. One of them, SSX-2 44-58 (SEQ ID NO:53), was mostly overlapping the previously defined DR11 restricted epitope, whereas the other, SSX-2 37-51 (SEQ ID NO:52) was completely distinct (FIG. 8A). Upon screening of the overall SSX-2 sequence as per the presence of DRB1*0301 binding sequences, SSX-2 37-51 and SSX-2 44-58 ranked 3rd and 4th respectively and SSX-2 37-51 exhibited a higher binding score as compared to SSX-2 44-58.

Mapping of the actual epitope recognized by SSX-2 specific DR3 restricted CD4+ T cells was then assessed experimentally by analyzing the capacity of SSX-2 37-58 relative to that of truncated peptide variants to stimulate IFN-g secretion by specific T cells, in a peptide titration assay (FIG. 8B). The results of this analysis were compared to those obtained with a previously described DR11 restricted T cell clone (Ayyoub M, et al., J Clin Invest., 2004; 113 (8): 1225-33). As summarized in FIG. 8C, progressive truncation of the first 8 amino acids at the N-terminus did not significantly affect recognition by the DR11 restricted clone, but dramatically impacted recognition by the DR3 restricted clones, that was indeed abolished by truncation of the first 4 N-terminal amino acids. In contrast, whereas truncation of C terminal amino acids rapidly resulted in loss of activity in the case of the DR11 restricted clone, antigen recognition by DR3 restricted clones was only minimally affected by truncations at the C-terminus, up to 8 amino acids. In summary, this analysis allowed us to locate the DR3 restricted epitope in the 37-51 region of the SSX-2 protein, consistent with the peptide of higher DR3 binding potential in the binding prediction analysis.

Figure 8C:
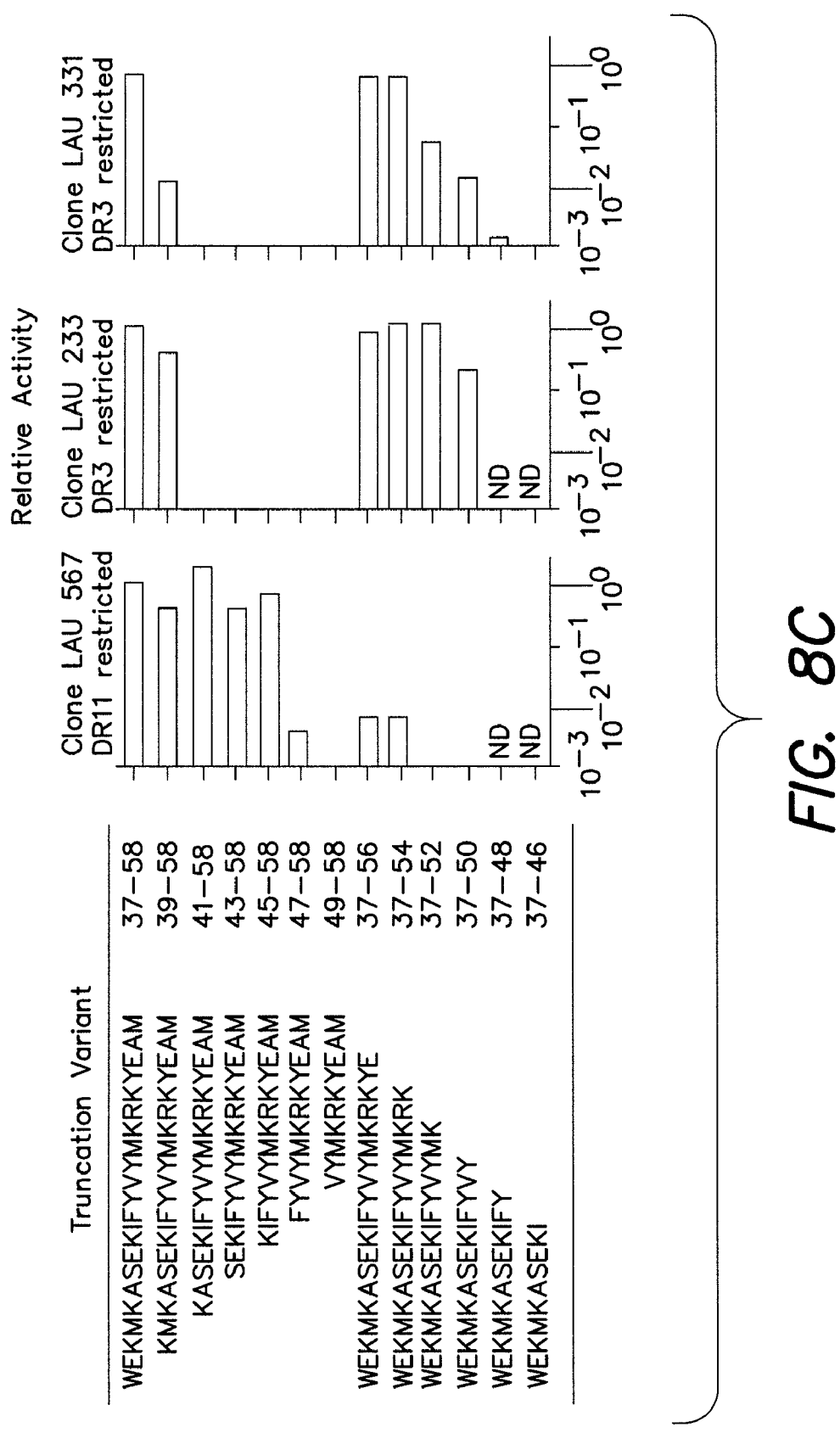

The intermediate size peptides of the truncation variants shown in FIG. 8C are shown in table IV and it is believed that these peptides would show activity with HLA-DR3.

TABLE IV

| Intermediate Peptides | | |
|---|---|---|
| SEQ ID NO: 56 | WEKMKASEKIFYVYMKRKYEA | 37-57 |
| SEQ ID NO: 57 | WEKMKASEKIFYVYMKRKY | 37-55 |

TABLE IV-continued

Intermediate Peptides

| SEQ ID NO: 58 | WEKMKASEKIFYVYMKR | 37-53 |
| --- | --- | --- |
| SEQ ID NO: 59 | WEKMKASEKIFYVYM | 37-51 |
| SEQ ID NO: 60 | WEKMKASEKIFYV | 37-49 |
| SEQ ID NO: 61 | EKMKASEKIFYVYMKRKYEA | 38-57 |
| SEQ ID NO: 62 | EKMKASEKIFYVYMKRKY | 38-55 |
| SEQ ID NO: 63 | EKMKASEKIFYVYMKR | 38-53 |
| SEQ ID NO: 64 | EKMKASEKIFYVYM | 38-51 |
| SEQ ID NO: 65 | EKMKASEKIFYV | 38-49 |
| SEQ ID NO: 66 | KMKASEKIFYVYMKRKYEA | 39-57 |
| SEQ ID NO: 67 | KMKASEKIFYVYMKRKY | 39-55 |
| SEQ ID NO: 68 | EKMKASEKIFYVYMKR | 39-53 |
| SEQ ID NO: 69 | EKMKASEKIFYVYM | 39-51 |
| SEQ ID NO: 70 | KMKASEKIFYV | 39-49 |
| SEQ ID NO: 71 | EKMKASEKIFYVYMKRKYE | 38-56 |
| SEQ ID NO: 72 | EKMKASEKIFYVYMKRK | 38-54 |
| SEQ ID NO: 73 | EKMKASEKIFYVYMK | 38-52 |
| SEQ ID NO: 74 | EKMKASEKIFYVY | 38-50 |
| SEQ ID NO: 75 | EKMKASEKIFY | 38-48 |
| SEQ ID NO: 76 | KMKASEKIFYVYMKRKYE | 39-56 |
| SEQ ID NO: 77 | KMKASEKIFYVYMKRK | 39-54 |
| SEQ ID NO: 78 | EKMKASEKIFYVYMK | 39-52 |
| SEQ ID NO: 79 | EKMKASEKIFYVY | 39-50 |
| SEQ ID NO: 80 | KMKASEKIFY | 39-48 |

Recognition of the Naturally Processed T Cell Epitope by SSX-2 37-51 Specific DR3 Restricted CD4+ T Cells.

Figure 9A:
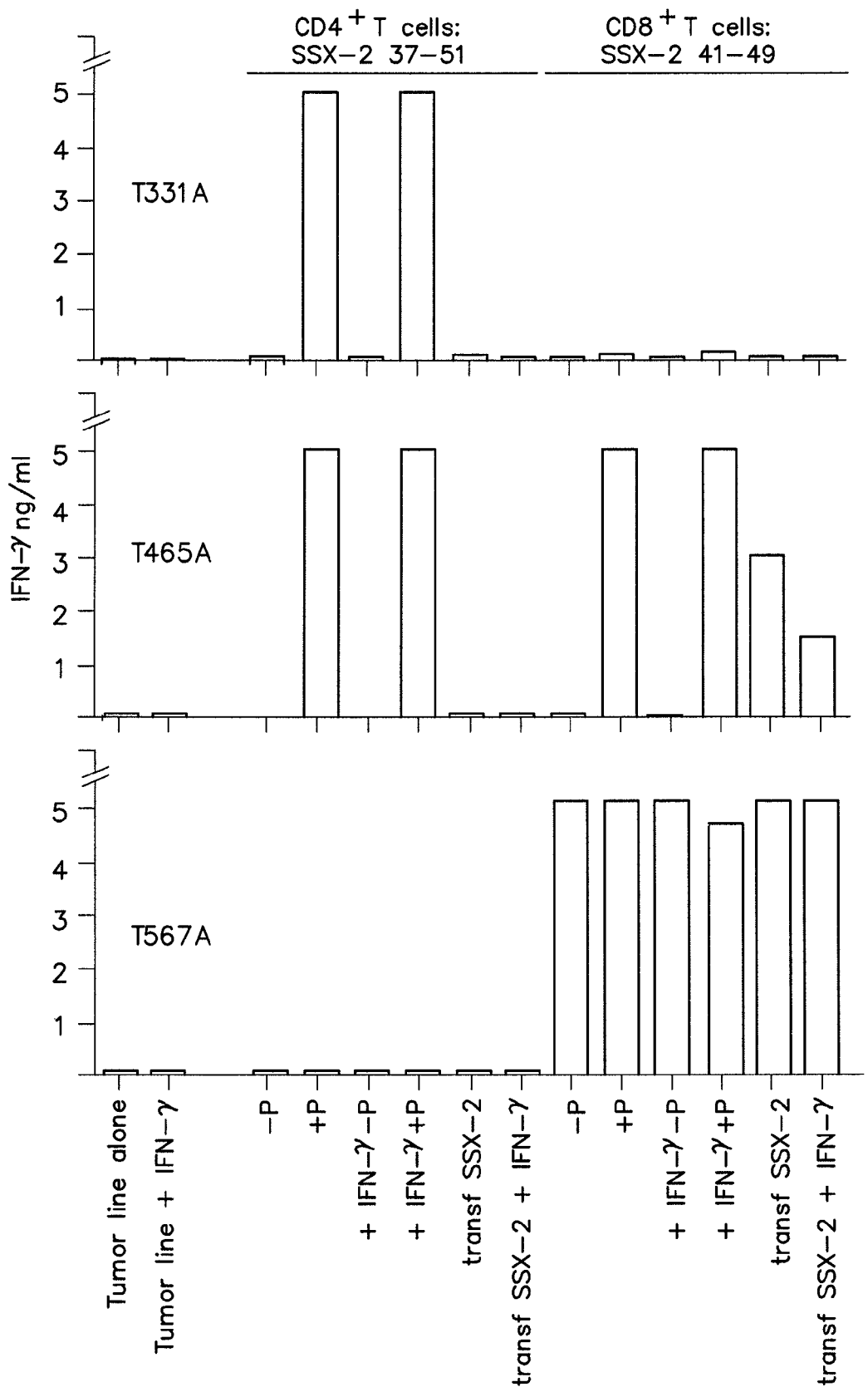

To assess if the T cell epitope recognized by SSX-2 37-51 reactive DR3 restricted CD4+ T cells was naturally presented on the surface of tumor cells, we used 3 melanoma cell lines. One of them was an autologous melanoma cell line from patient LAU 331 (T331A). In addition, we tested a DR3 expressing (T465A) cell line and a DR3 negative cell line (T567A) (FIG. 9A). All tumor cell lines expressed detectable levels of HLA-DR that were further increased upon treatment with IFN-g. Tumor cell lines were tested as such or treated with IFN-g and transfected or not with an SSX-2 encoding plasmid. In addition to DR3 restricted CD4+ T cells, recognition by SSX-2 specific HLA-A2 restricted CD8+ T cells was also assessed as an internal control. As illustrated in FIG. 9, SSX-2 37-51 reactive DR3 restricted CD4+ T cells failed to recognize both naturally expressing and SSX-2 transfected tumor cells in the absence of exogenously added SSX-2 37-51 peptide. In contrast, SSX-2 41-49 specific, A2 restricted, CD8+ T cells efficiently recognized A2+ tumor cells naturally expressing the SSX-2 antigen or upon transfection with the SSX-2 encoding plasmid. Thus, no evidence of antigen presentation to SSX-2 specific CD4+ T cells through the endogenous processing pathway was obtained.

Figures 9B, 9C:
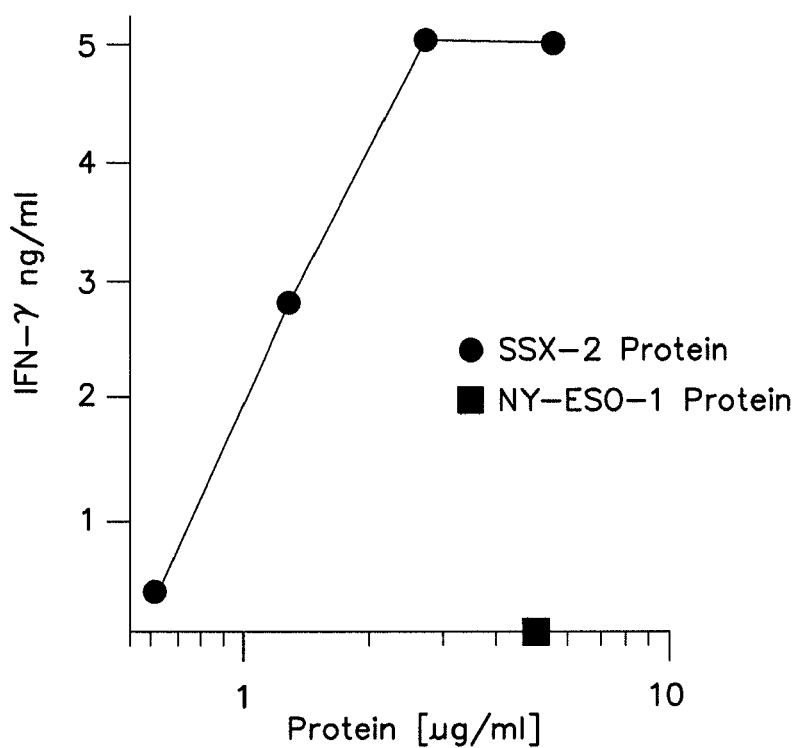

Professional antigen presenting cells (APC), however, were able to efficiently process and present the DR3 epitope to SSX-2 CD4+ T cells through the exogenous pathway. Indeed, as illustrated in FIG. 9C, DR3+EBV cells were able to efficiently process the recombinant SSX-2 protein and present the 37-51 epitope to specific CD4+ T cells, whereas no recognition was obtained using NY-ES 0-1 recombinant protein used as an internal control.

Cross-recognition of Other SSX Antigens by SSX-2 Specific DR3 Restricted CD4+ T Cells.

As a high degree of homology exists between SSX-2 and other SSX family members, it was interesting to assess the ability of SSX-2 specific DR3 restricted CD4+ T cells to recognize homologous peptides in the sequence of other SSX proteins. Using the binding prediction program, we obtained high binding scores for SSX 37-51 homologous peptides indicating that these peptides could potentially represent DR3 restricted epitopes (FIG. 10A). This was the result of the large conservation of the amino acid positions representing anchor residues for binding to DRB1*0301 with only one of these residues (position 6) being polymorphic in the analyzed sequences, but in all cases occupied by an amino acid known, at this position, to favorably impact on binding to DRB1*0301. The actual recognition of SSX 37-51 homologous peptides by DR3 restricted SSX-2 specific CD4+ T cells was then assessed functionally in a peptide titration assay. No cross-recognition was detected in the case of SSX-1 and SSX-3. In contrast, SSX-4 and SSX-5 37-51 homologous peptides were recognized by SSX-2 specific, DR3 restricted CD4+ T cells about 10 and 3 fold less efficiently as compared to the SSX-2 37-51 peptide, respectively (FIG. 10B). However, cross-recognition of the SSX-4 protein (that was available for analysis) was barely detectable (FIG. 10C) indicating that a reduction of only 10 fold in the efficiency of peptide recognition by specific CD4+ T cell has a profound impact on the cross-recognition of the native antigen.

Discussion

Specific expression or over expression of antigens in tumor cells as compared to normal somatic tissues provides the molecular bases for the development of immunotherapeutic approaches for the treatment of cancer. In this context, the analysis of tumor antigen specific immune responses naturally arising in cancer patients is of great interest, as it allows one to narrow the choice of candidate tumor antigens to those that are physiologically relevant, and provides the opportunity to investigate their characteristics as well as the underlying molecular mechanisms leading to their immunogenicity.

Development of the SEREX method (Serological identification of antigens by recombinant expression cloning), in 1995 by M. Pfreundschuh and colleagues, has been key in this regard, allowing the identification of proteins recognized by IgG antibodies from cancer patients' sera. Application of this methodology led to the identification of a group of tumor specific antigens including the NY-ESO, SSX, and SCP-1 antigens (Tureci O, et al., Cancer Res., 1996; 56 (20): 4766-72; Chen Y T, et al., Proc. Natl. Acad. Sci. U.S.A., 1997; 94 (5): 1914-8; Tureci 0, et al., Proc. Natl. Acad. Sci. U.S.A., 1998; 95 (9): 5211-6). High natural immunogenicity of NY-ESO-1 in cancer patients bearing antigen expressing tumors has been confirmed in studies from different groups and, as a result of these analyses, several NY-ESO-1 derived CD8+ and CD4+ T cell epitopes have been identified (Valmori D, et al., Cancer Res., 2000; 60: 4499-506; Zarour H M, et al., Cancer Res., 2000; 60 (17): 4946-52; Zeng G, et al., J. Immunol., 2000; 165 (2): 1153-9; Jäger E, et al., J. Exp. Med., 1998; 187 (2): 265-70; Gnjatic S, et al., Proc. Natl. Acad. Sci. U.S.A., 2000; 97 (20): 10917-22). Based on these findings, several clinical trials using NY-ESO-1-derived immunogens are currently underway.

The SSX-2 encoded antigen (initially named HOM-MEL-40) was cloned by SEREX using the serum from a metastatic melanoma patient (Sahin U, et al., Proc. Natl. Acad. Sci. U.S.A., 1995; 92 (25): 11810-3). Following this initial study, antibodies against SSX-2 were found in 10% of patients with melanoma (Tureci O, et al., Cancer Res., 1996; 56 (20): 4766-72). These results brought attention to the products of the SSX gene family, previously thought to be expressed only in synovial sarcoma, as potential relevant targets of generic cancer vaccines. Confirmation of this came by studies reporting frequent expression of SSX genes in tumors of different histological types including head and neck cancer, ovarian cancer, malignant melanoma (Tureci O, et al., Int. J. Cancer, 1998; 77 (1): 19-23; Tureci O, et al., Cancer Res., 1996; 56 (20): 4766-72), sarcoma (Ayyoub M, et al., Cancer Immunity, 2003; 3: 13; Naka N, et al., Int. J. Cancer, 2002; 98 (4): 640-2) and hepatocellular carcinoma (Chen C H, et al., Cancer Lett., 2001; 164 (2): 189-95).

To implement the development of SSX based cancer vaccines, we undertook the analysis of T cell responses to SSX-2 in melanoma patients bearing antigen-expressing tumors. Based on the concept that tumor specific CD8+ T lymphocytes (CTL) are the major effectors of the immune response against cancer, the elicitation of specific CTL responses against tumor antigens was until recently, the major aim of cancer vaccination trials. Therefore, most studies, including ours, were aimed at the identification of epitopes recognized by tumor specific CTL. In these initial studies we identified an immunodominant CTL epitope restricted by the frequently expressed MHC Class I allele HLA-A2 (Ayyoub M, et al., J. Immunol., 2002; 168 (4):1717-22; Ayyoub M, et al., Cancer Res., 2003; 63: 5601-6; Rubio-Godoy V, et al., Eur. J. Immunol., 2002; 32 (8): 2292-9). More recently, however, the need for more complex and integrated CD4+ and CD8+ T cell responses for tumors regression to occur in vivo has been increasingly recognized (Toes R E, et al., J. Exp. Med., 1999; 189 (5): 753-6). Although the key role of tumor antigen specific CD4+ T cells in mediating a variety of anti-tumor functions has been long acknowledged (Hung K, et al., J. Exp. Med., 1998; 188 (12): 2357-68; James R F, et al., Immunology, 1991; 72 (2): 213-8; Mumberg D, et al., Proc. Natl. Acad. Sci. U.S.A., 1999; 96 (15): 8633-8; Qin Z and Blankenstein T., Immunity, 2000; 12 (6): 677-86; Wang R F., Trends Immunol., 2001; 22 (5): 269-76), the concept that elicitation of vigorous and long lasting tumor specific responses by vaccination might require the participation of CD4+ T cells has been emphasized only recently, mainly because clinical trials of cancer patients vaccination using tumor antigen derived MHC class I restricted peptides alone have overall reported weak and transient antigen specific T cell responses. The desire of incorporating CD4+ T cell epitopes into tumor vaccines has therefore encouraged the development and application of methodologies for the identification of tumor antigen derived, MHC Class II restricted, sequences recognized by specific CD4+ T cells in association with frequently expressed MHC Class II alleles. In addition, the provocative recent observation that at least some tumor antigen specific CD4+ T cells could exert immunoregulatory functions (Wang H Y, et al., Immunity, 2004; 20 (1): 107-18) is further stimulating a growing interest for the analysis of naturally occurring CD4+ T cell responses to tumor antigens.

We have recently reported the identification of two SSX-2 derived CD4+ T cell epitopes (Ayyoub M, et al., J. Immunol., 2004; 172 (11): 7206-11; Ayyoub M, et al., J Clin Invest., 2004; 113 (8): 1225-33). One of them, located in the 37-58 region of the protein and restricted by DR11, is the target of naturally occurring CD4+ T cell responses in the majority of antigen expressing DR11+ melanoma patients analyzed. With the aim of characterizing previously detected specific CD4+ T cell responses to peptide SSX-2 37-58 in two DR1 negative melanoma patients, in this study, we have isolated and assessed SSX-2 37-58 specific clonal populations from these patients. Recognition of the epitope by specific CD4+ T cells from both patients was HLA-DR restricted. Analysis of the molecular typing of the melanoma patients and of partially matched homozygous EBV, in relation to their capacity to present the epitope to specific CD4+ T cells, revealed that recognition was restricted by the DRB1*0301 allele. Of two peptides in the 37-58 region predicted to be good DRB1*0301 binders using the SYFPEITHI prediction program (refer to the Institute for Cell Biology, Department of Immunology for a database of MHC ligands and peptide motifs) we identified peptide SSX-2 37-51 as the one recognized by DR3 restricted CD4+ T cells. The DR3 epitope is therefore clearly distinct from the previously defined DR11 restricted one that is instead located in the C-terminal part (45-59) of the active region. Importantly, assessment of the frequency of DRB1*03 alleles in population groups in the U.S. has revealed frequent expression in several major ethnic groups including 23.4% of Caucasoids, 24.9% of African Americans, 10.4% of Asians/Pacific Islanders, 16.9% of Hispanics and 24.4% of Native Americans (Tang T F, et al., Immunol., 2002; 63 (3): 221-8), DRB1*0301 being the predominant DRB1*03 allele in all populations. Therefore, the identification of the DRB1*0301 restricted epitope significantly increases the fraction of patients potentially able to mount an SSX-2 specific CD4+ T cell response to vaccination with peptides in this region of the protein.

SSX-1 to -5 exhibit high sequence homology, ranging from 88 to 95% at the nucleotide level and from 77 to 91% at the amino acid level (Gure A O, et al., Int. J. Cancer, 1997; 72 (6): 965-71). Homologous peptides in the sequence of SSX proteins other than SSX-2 could also represent DRB1*0301 restricted epitopes as they rank at the highest positions for binding to DRB1*0301 among SSX 15mers due to conservation of most anchor residues. This hypothesis has been confirmed by our recent isolation, in the context of an analysis of SSX-4 specific CD4+ T cell responses in antigen expressing patients, of SSX-4 37-51 specific DR3 restricted CD4+ T cell clonal populations. However, consistent with our previous findings with T cell clones specific for the previously identified SSX-2 epitopes, cross-recognition of SSX homologous sequence by SSX-2 37-51 specific DR3 restricted CD4+ T cells was only partial, limited to the SSX-5 and SSX-4 homologous peptides and no reactivity was detected towards the SSX-4 recombinant protein. Thus, due to limited cross-recognition of SSX homologous sequences, SSX based vaccines should contain individual sequences from the more frequently expressed family members.

Specific CD4+ T cell responses to SSX-2 37-51 were found in the two DR3 expressing melanoma patients bearing SSX-2 positive tumors, but not in 3 DRB1*0301 expressing healthy donors analyzed under identical test conditions (i.e. after two rounds of in vitro stimulation with peptide SSX-2 37-58, not shown), underlining the physiological relevance of the identified epitope. SSX-2 specific DR3 restricted CD4+ T cells failed to recognize SSX-2 expressing tumor cells. In contrast, they recognized the SSX-2 recombinant protein, upon processing and presentation by EBV cells. These results are consistent with those that we have previously obtained for both the DR11 and the DP1 restricted SSX-2 epitopes and support processing and presentation of tumor derived SSX-2 antigen by professional APC, through the exogenous pathway, as being the main mechanism through which natural CD4+ T cell responses to SSX-2 expressing tumors may occur.

It is noteworthy that the newly identified DR3 restricted epitope is located in the very same region of, and actually overlaps, the two previously defined DR11 and A2 restricted epitopes (Ayyoub M, et al., J. Immunol., 2002; 168 (4):1717-22; Ayyoub M, et al., J Clin Invest., 2004; 113 (8): 1225-33). Another epitope restricted by DP1 is located in the close N-terminal region (Gure, A. O., et al., SSX: a multigene family with several members transcribed in normal testis and human cancer, *Int. J. Cancer*, (1997), 72, 965-971). Interestingly, this region of the protein contains some additional peptides with high binding potential for other frequently expressed DR molecules (e.g. 34-48 SEQ ID NO:81 for DRB1*0101, 49-63 SEQ ID NO:82 for DRB1*1501). Retrieval of overlapping immunodominant epitopes in a relatively short amino acid stretch suggests the presence of a potential "hot spot" for T cell recognition in this region of the SSX-2 protein. Hotspots of T cell epitopes have been previously described for responses to different antigens including viral and tumoral antigens (Surman S, et al., Proc. Natl. Acad. Sci. U.S.A., 2001; 98 (8): 4587-92; Zarour H M, et al., Cancer Res., 2002; 62 (1): 213-8; Consogno G, et al., Blood, 2003; 101 (3): 1038-44). Extensive studies have concentrated on the elaboration of approaches for the identification of protein regions that can bind to multiple MHC molecules and evoke a T cell response. This has resulted in the development of programs that can predict peptide binding to a number of frequently expressed MHC class I or II alleles with a high degree of confidence (Rammensee H, et al., Immunogenetics, 1999; 50 (3-4): 213-9) or that can identify short protein regions containing sequences binding multiple MHC class II molecules (Sturniolo T, et al., Nat. Biotechnol., 1999; 17 (6): 555-61). Despite these efforts, however, the rules determining the immunogenicity of a given protein region have mostly remained unveiled. In an interesting study assessing H2-IAb restricted CD4+ T cell responses to an HIV env (gp140) glycoprotein in vaccinated mice, S. Surman and colleagues could identify immunogenic peptides only within four regions of the protein (Surman S, et al., Proc. Natl. Acad. Sci. U.S.A., 2001; 98 (8): 4587-92). Analysis of the immunogenic regions in the context of the crystal structure of the protein showed localization of the former within exposed, non helical strands, indicating that immunodominance of antigenic epitopes could be influenced by their location in the three-dimensional native structure of the protein. Several factors, more or less directly related to the structure of a given protein domain, such as accessibility to fragmentation by proteases in the antigen processing pathway, are likely to be critical for determining the immunogenicity of peptides within defined protein stretches. Hopefully, more extensive comparisons between predicted MHC binding, epitope localization, protein structure and proteolytic patterns will in the future provide the opportunity to validate these concepts and assess their predictive values. Meanwhile, epitope mapping using naturally arising, physiologically relevant, tumor antigen specific T cell clones is useful for the identification of hotspot regions that may prove sufficient for the induction of specific immune responses in the majority of patients.

Other aspects of the invention will be clear to the skilled artisan and need not be repeated here. Each reference cited herein is incorporated by reference in its entirety.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A composition comprising an isolated HLA class I-binding peptide and an isolated SSX-2 HLA class II-binding peptide, wherein the isolated SSX-2 HLA class II-binding peptide comprises an amino acid sequence set forth as SEQ ID NO:54, and wherein the HLA class II binding peptide does not include the full length SSX-2 protein.

2. The composition of claim 1, wherein the HLA class I-binding peptide and the SSX-2 HLA class II-binding peptide are combined as a polytope polypeptide.

3. The composition of claim 1, wherein the isolated SSX-2 HLA class II-binding peptide comprises an amino acid sequence selected from the group consisting of SEQ ID NO:28, SEQ ID NO:29, SEQ ID NO:30, SEQ ID NO:31, SEQ ID NO:52, SEQ ID NO:53 and SEQ ID NO:55.

4. The composition of claim 1, wherein the isolated SSX-2 HLA class II-binding peptide comprises an endosomal targeting signal.

5. The composition of claim 4, wherein the endosomal targeting signal comprises an endosomal targeting portion of human invariant chain Ii.

6. The composition of claim 1, wherein the isolated peptide is non-hydrolyzable.

7. The composition of claim 6, wherein the isolated peptide is selected from the group consisting of peptides comprising D-amino acids, peptides comprising a -psi[CH$_2$NH]-reduced amide peptide bond, peptides comprising a -psi[COCH$_2$]-ketomethylene peptide bond, peptides comprising a -psi[CH(CN)NH]-(cyanomethylene)amino peptide bond, peptides comprising a -psi[CH$_2$CH(OH)]-hydroxyethylene peptide bond, peptides comprising a -psi[CH$_2$O]-peptide bond, and peptides comprising a -psi[CH$_2$S]-thiomethylene peptide bond.

8. The composition of claim 1, wherein the HLA class I-binding peptide is a SSX-2 HLA class I-binding peptide.

* * * * *

SEQUENCE LISTING

```
<160> NUMBER OF SEQ ID NOS: 86

<210> SEQ ID NO 1
<211> LENGTH: 1322
<212> TYPE: DNA
<213> ORGANISM: Homo sapiens

<400> SEQUENCE: 1
gcatgctctg actttctctc tctttcgatt cttccatact cagagtacgc acggtctgat    60
tttctctttg gattcttcca aaatcagagt cagactgctc ccggtgccat gaacggagac   120
gacgcctttg caaggagacc cacggttggt gctcaaatac cagagaagat ccaaaaggcc   180
ttcgatgata ttgccaaata cttctctaag gaagagtggg aaaagatgaa agcctcggag   240
aaaatcttct atgtgtatat gaagagaaag tatgaggcta tgactaaact aggtttcaag   300
gccaccctcc cacctttcat gtgtaataaa cgggccgaag acttccaggg gaatgatttg   360
gataatgacc ctaaccgtgg gaatcaggtt gaacgtcctc agatgacttt cggcaggctc   420
cagggaatct ccccgaagat catgcccaag aagccagcag aggaaggaaa tgattcggag   480
gaagtgccag aagcatctgg cccacaaaat gatgggaaag agctgtgccc ccggggaaaa   540
ccaactacct ctgagaagat tcacgagaga tctggaccca aaggggggga acatgcctgg   600
acccacagac tgcgtgagag aaaacagctg gtgatttatg aagagatcag cgaccctgag   660
gaagatgacg agtaactccc ctcagggata cgacacatgc ccatgatgag aagcagaacg   720
```

```
tggtgacctt tcacgaacat gggcatggct gcggacccct cgtcatcagg tgcatagcaa      780
gtgaaagcaa gtgttcacaa cagtgaaaag ttgagcgtca ttttcttag tgtgccaaga      840 gttcgatgtt agcgtttacg ttgtatttc ttacactgtg tcattctgtt agatactaac      900 atttcattg atgagcaaga catacttaat gcatattttg gtttgtgtat ccatgcacct      960
accttagaaa acaagtattg tcggttacct ctgcatggaa cagcattacc ctcctctctc     1020
cccagatgtg actactgagg gcagttctga gtgtttaatt tcagattttt tcctctgcat     1080
ttacacacac acgcacacaa accacaccac acacacacac acacacacac acacacacac     1140
acacacacac caagtaccag tataagcatc tgccatctgc ttttcccatt gccatgcgtc     1200
ctggtcaagc tcccctcact ctgtttcctg gtcagcatgt actcccctca tccgattccc     1260
ctgtagcagt cactgacagt taataaacct ttgcaaacgt tcaaaaaaaa aaaaaaaaa      1320 aa                                                                     1322
```

<210> SEQ ID NO 2
<211> LENGTH: 188
<212> TYPE: PRT
<213> ORGANISM: Homo sapiens

<400> SEQUENCE: 2

```
Met Asn Gly Asp Asp Ala Phe Ala Arg Arg Pro Thr Val Gly Ala Gln
 1               5                  10                  15

Ile Pro Glu Lys Ile Gln Lys Ala Phe Asp Asp Ile Ala Lys Tyr Phe
            20                  25                  30

Ser Lys Glu Glu Trp Glu Lys Met Lys Ala Ser Glu Lys Ile Phe Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Lys Arg Ala Glu Asp Phe Gln
65                  70                  75                  80

Gly Asn Asp Leu Asp Asn Asp Pro Asn Arg Gly Asn Gln Val Glu Arg
                85                  90                  95

Pro Gln Met Thr Phe Gly Arg Leu Gln Gly Ile Ser Pro Lys Ile Met
            100                 105                 110

Pro Lys Lys Pro Ala Glu Glu Gly Asn Asp Ser Glu Glu Val Pro Glu
        115                 120                 125

Ala Ser Gly Pro Gln Asn Asp Gly Lys Glu Leu Cys Pro Pro Gly Lys
    130                 135                 140

Pro Thr Thr Ser Glu Lys Ile His Glu Arg Ser Gly Pro Lys Arg Gly
145                 150                 155                 160

Glu His Ala Trp Thr His Arg Leu Arg Glu Arg Lys Gln Leu Val Ile
                165                 170                 175

Tyr Glu Glu Ile Ser Asp Pro Glu Glu Asp Asp Glu
            180                 185
```

<210> SEQ ID NO 3
<211> LENGTH: 1466
<212> TYPE: DNA
<213> ORGANISM: Homo sapiens

<400> SEQUENCE: 3

```
gcatgctctg actttctctc tctttcgatt cttccatact cagagtacgc acggtctgat       60 tttctcttg gattcttcca aaatcagagt cagactgctc ccggtgccat gaacggagac      120
gacgcctttg caaggagacc cacggttggt gctcaaatac cagagaagat ccaaaaggcc      180
```

-continued

```
ttcgatgata ttgccaaata cttctctaag gaagagtggg aaaagatgaa agcctcggag    240
aaaatcttct atgtgtatat gaagagaaag tatgaggcta tgactaaact aggtttcaag    300
gccaccctcc cacctttcat gtgtaataaa cgggccgaag acttccaggg gaatgatttg    360
gataatgacc ctaaccgtgg gaatcaggtt gaacgtcctc agatgacttt cggcaggctc    420
cagggaatct ccccgaagat catgcccaag aagccagcag aggaaggaaa tgattcggag    480
gaagtgccag aagcatctgg cccacaaaat gatgggaaag agctgtgccc cccgggaaaa    540
ccaactacct ctgagaagat tcacgagaga tctggaaata gggaggccca agaaaaggaa    600
gagagacgcg gaacagctca tcggtggagc agtcagaaca cacacaacat tggtcgattc    660
agtttgtcaa cttctatggg tgcagttcat ggtaccccca aaacaattac acacaacagg    720
gacccaaaag gggggaacat gcctggaccc acagactgcg tgagagaaaa cagctggtga    780
tttatgaaga gatcagcgac cctgaggaag atgacgagta actcccctca gggatacgac    840
acatgcccat gatgagaagc agaacgtggt gacctttcac gaacatgggc atggctgcgg    900 accectcgtc atcaggtgca tagcaagtga aagcaagtgt tcacaacagt gaaaagttga    960
gcgtcatttt tcttagtgtg ccaagagttc gatgttagcg tttacgttgt attttcttac    1020
actgtgtcat tctgttagat actaacattt tcattgatga gcaagacata cttaatgcat    1080
attttggttt gtgtatccat gcacctacct tagaaaacaa gtattgtcgg ttacctctgc    1140
atggaacagc attaccctcc tctctcccca gatgtgacta ctgagggcag ttctgagtgt    1200
ttaatttcag attttttcct ctgcatttac acacacacgc acacaaacca caccacacac    1260
acacacacac acacacacac acacacacac acacaccaag taccagtata agcatctgcc    1320
atctgctttt cccattgcca tgcgtcctgg tcaagctccc ctcactctgt ttcctggtca    1380
gcatgtactc ccctcatccg attcccctgt agcagtcact gacagttaat aaaccttgc     1440 aaacgttcaa aaaaaaaaaa aaaaaa                                         1466
```

<210> SEQ ID NO 4
<211> LENGTH: 223
<212> TYPE: PRT
<213> ORGANISM: Homo sapiens

<400> SEQUENCE: 4

```
Met Asn Gly Asp Asp Ala Phe Ala Arg Arg Pro Thr Val Gly Ala Gln
1               5                   10                  15

Ile Pro Glu Lys Ile Gln Lys Ala Phe Asp Asp Ile Ala Lys Tyr Phe
            20                  25                  30

Ser Lys Glu Glu Trp Glu Lys Met Lys Ala Ser Glu Lys Ile Phe Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Lys Arg Ala Glu Asp Phe Gln
65                  70                  75                  80

Gly Asn Asp Leu Asp Asn Asp Pro Asn Arg Gly Asn Gln Val Glu Arg
                85                  90                  95

Pro Gln Met Thr Phe Gly Arg Leu Gln Gly Ile Ser Pro Lys Ile Met
            100                 105                 110

Pro Lys Lys Pro Ala Glu Glu Gly Asn Asp Ser Glu Glu Val Pro Glu
        115                 120                 125

Ala Ser Gly Pro Gln Asn Asp Gly Lys Glu Leu Cys Pro Pro Gly Lys
    130                 135                 140
```

```
Pro Thr Thr Ser Glu Lys Ile His Glu Arg Ser Gly Asn Arg Glu Ala
145                 150                 155                 160

Gln Glu Lys Glu Glu Arg Arg Gly Thr Ala His Arg Trp Ser Ser Gln
            165                 170                 175

Asn Thr His Asn Ile Gly Arg Phe Ser Leu Ser Thr Ser Met Gly Ala
        180                 185                 190

Val His Gly Thr Pro Lys Thr Ile Thr His Asn Arg Asp Pro Lys Gly
    195                 200                 205

Gly Asn Met Pro Gly Pro Thr Asp Cys Val Arg Glu Asn Ser Trp
    210                 215                 220
```

<210> SEQ ID NO 5
<211> LENGTH: 1274
<212> TYPE: DNA
<213> ORGANISM: Homo sapiens
<220> FEATURE:
<221> NAME/KEY: misc_feature
<222> LOCATION: (547)..(560)
<223> OTHER INFORMATION: n is a, c, g, or t

<400> SEQUENCE: 5

```
ctctctcttt cgattcttcc atactcagag tacgcacggt ctgatttcct ctttggattc        60
ttccaaaatc agagtcagac tgctcccggt gccatgaacg agacgacgc ctttgcaagg        120 agacccacgg ttggtgctca ataccgagag aagatccaaa aggccttcga tgatattgcc       180
aaatacttct ctaaggaaga gtgggaaaag atgaaagcct cggagaaaat cttctatgtg       240
tatatgaaga gaaagtatga ggctatgact aaactaggtt tcaaggccac cctcccacct       300
ttcatgtgta taaacgggc cgaagacttc caggggaatg atttggataa tgaccctaac        360
cgtgggaatc aggttgaacg tcctcagatg actttcggca ggctccaggg aatctccccg       420
aagatcatgc ccaagaagcc agcagaggaa ggaaatgatt cggaggaagt gccagaagca       480
tctggcccac aaaatgatgg gaaagagctg tgccccccgg gaaaaccaac tacctctgag       540
aagattnnnn nnnnnnnnnn gacccaaaag gggggaacat gcctggaccc acagactgcg       600
tgagagaaaa cagctggtga tttatgaaga gatcagcgac cctgaggaag atgacgagta       660
actcccctcg gggatacgac acatgcccat gatgagaagt agaacgtggt gacctttcac       720
gaacataggc atggctgcgg acccctcgtc atcaggtgca tagcaagtga agcaagtgt        780 tcacaacagt gaaaagttga gcgtcgtttt tcttagtgtg acaagagttc gatgttagtg       840
tttccattgt attttcttac agtgtgccat tctgttagat attagcgttt tcattgatga       900
gcaagacatg cttaatgtgt atttcggttt gtgtatccat gcacctacct cagaaagcaa       960
gtatagtcag gtattctctc catagaacag cactaccctc ctctctcccc agatgtgact      1020
actgagggca gatctgagtg tttaatttcc gattttcccc tctgcattta cacaccagac      1080
acacaaacac acacacacag acacacacac acacagacac accaagtacc agtataagca      1140
tctcccatat gcttttcccc attgccatga gtcctggtca agcccccctt caatttgttt      1200
cctgttcagc atgtactccc ctcctctgat tccccgtatc agtcactgac agttaataca      1260
cctttgcaaa cgtt                                                         1274
```

<210> SEQ ID NO 6
<211> LENGTH: 169
<212> TYPE: PRT
<213> ORGANISM: Homo sapiens
<220> FEATURE:
<221> NAME/KEY: misc_feature
<222> LOCATION: (152)..(156)
<223> OTHER INFORMATION: Xaa can be any naturally occurring amino acid

<400> SEQUENCE: 6

Met Asn Gly Asp Asp Ala Phe Ala Arg Arg Pro Thr Val Gly Ala Gln
1               5                   10                  15

Ile Pro Glu Lys Ile Gln Lys Ala Phe Asp Asp Ile Ala Lys Tyr Phe
            20                  25                  30

Ser Lys Glu Glu Trp Glu Lys Met Lys Ala Ser Glu Lys Ile Phe Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Lys Arg Ala Glu Asp Phe Gln
65                  70                  75                  80

Gly Asn Asp Leu Asp Asn Asp Pro Asn Arg Gly Asn Gln Val Glu Arg
                85                  90                  95

Pro Gln Met Thr Phe Gly Arg Leu Gln Gly Ile Ser Pro Lys Ile Met
            100                 105                 110

Pro Lys Lys Pro Ala Glu Glu Gly Asn Asp Ser Glu Glu Val Pro Glu
        115                 120                 125

Ala Ser Gly Pro Gln Asn Asp Gly Lys Glu Leu Cys Pro Pro Gly Lys
    130                 135                 140

Pro Thr Thr Ser Glu Lys Ile Xaa Xaa Xaa Xaa Xaa Thr Gln Lys Gly
145                 150                 155                 160

Gly Thr Cys Leu Asp Pro Gln Thr Ala
                165

<210> SEQ ID NO 7
<211> LENGTH: 22
<212> TYPE: PRT
<213> ORGANISM: Artificial sequence
<220> FEATURE:
<223> OTHER INFORMATION: SSX-2 peptide

<400> SEQUENCE: 7

Met Asn Gly Asp Asp Ala Phe Ala Arg Arg Pro Thr Val Gly Ala Gln
1               5                   10                  15

Ile Pro Glu Lys Ile Gln
            20

<210> SEQ ID NO 8
<211> LENGTH: 22
<212> TYPE: PRT
<213> ORGANISM: Artificial sequence
<220> FEATURE:
<223> OTHER INFORMATION: SSX-2 peptide

<400> SEQUENCE: 8

Val Gly Ala Gln Ile Pro Glu Lys Ile Gln Lys Ala Phe Asp Asp Ile
1               5                   10                  15

Ala Lys Tyr Phe Ser Lys
            20

<210> SEQ ID NO 9
<211> LENGTH: 22
<212> TYPE: PRT
<213> ORGANISM: Artificial sequence
<220> FEATURE:
<223> OTHER INFORMATION: SSX-2 peptide

<400> SEQUENCE: 9

Phe Asp Asp Ile Ala Lys Tyr Phe Ser Lys Glu Glu Trp Glu Lys Met
1               5                   10                  15

```
Lys Ala Ser Glu Lys Ile
            20

<210> SEQ ID NO 10
<211> LENGTH: 22
<212> TYPE: PRT
<213> ORGANISM: Artificial sequence
<220> FEATURE:
<223> OTHER INFORMATION: SSX-2 peptide

<400> SEQUENCE: 10

Trp Glu Lys Met Lys Ala Ser Glu Lys Ile Phe Tyr Val Tyr Met Lys
1               5                   10                  15

Arg Lys Tyr Glu Ala Met
            20

<210> SEQ ID NO 11
<211> LENGTH: 22
<212> TYPE: PRT
<213> ORGANISM: Artificial sequence
<220> FEATURE:
<223> OTHER INFORMATION: SSX-2 peptide

<400> SEQUENCE: 11

Val Tyr Met Lys Arg Lys Tyr Glu Ala Met Thr Lys Leu Gly Phe Lys
1               5                   10                  15

Ala Thr Leu Pro Pro Phe
            20

<210> SEQ ID NO 12
<211> LENGTH: 22
<212> TYPE: PRT
<213> ORGANISM: Artificial sequence
<220> FEATURE:
<223> OTHER INFORMATION: SSX-2 peptide

<400> SEQUENCE: 12

Leu Gly Phe Lys Ala Thr Leu Pro Pro Phe Met Cys Asn Lys Arg Ala
1               5                   10                  15

Glu Asp Phe Gln Gly Asn
            20

<210> SEQ ID NO 13
<211> LENGTH: 22
<212> TYPE: PRT
<213> ORGANISM: Artificial sequence
<220> FEATURE:
<223> OTHER INFORMATION: SSX-2 peptide

<400> SEQUENCE: 13

Asn Lys Arg Ala Glu Asp Phe Gln Gly Asn Asp Leu Asp Asn Asp Pro
1               5                   10                  15

Asn Arg Gly Asn Gln Val
            20

<210> SEQ ID NO 14
<211> LENGTH: 19
<212> TYPE: PRT
<213> ORGANISM: Artificial sequence
<220> FEATURE:
<223> OTHER INFORMATION: SSX-2 peptide

<400> SEQUENCE: 14

Asp Pro Asn Arg Gly Asn Gln Val Glu Arg Pro Gln Met Thr Phe Gly
1               5                   10                  15
```

Arg Leu Gln

<210> SEQ ID NO 15
<211> LENGTH: 22
<212> TYPE: PRT
<213> ORGANISM: Artificial sequence
<220> FEATURE:
<223> OTHER INFORMATION: SSX-2 peptide

<400> SEQUENCE: 15

Pro Gln Met Thr Phe Gly Arg Leu Gln Gly Ile Ser Pro Lys Ile Met
1               5                   10                  15

Pro Lys Lys Pro Ala Glu
            20

<210> SEQ ID NO 16
<211> LENGTH: 22
<212> TYPE: PRT
<213> ORGANISM: Artificial sequence
<220> FEATURE:
<223> OTHER INFORMATION: SSX-2 peptide

<400> SEQUENCE: 16

Pro Lys Ile Met Pro Lys Lys Pro Ala Glu Glu Gly Asn Asp Ser Glu
1               5                   10                  15

Glu Val Pro Glu Ala Ser
            20

<210> SEQ ID NO 17
<211> LENGTH: 22
<212> TYPE: PRT
<213> ORGANISM: Artificial sequence
<220> FEATURE:
<223> OTHER INFORMATION: SSX-2 peptide

<400> SEQUENCE: 17

Asn Asp Ser Glu Glu Val Pro Glu Ala Ser Gly Pro Gln Asn Asp Gly
1               5                   10                  15

Lys Glu Leu Cys Pro Pro
            20

<210> SEQ ID NO 18
<211> LENGTH: 22
<212> TYPE: PRT
<213> ORGANISM: Artificial sequence
<220> FEATURE:
<223> OTHER INFORMATION: SSX-2 peptide

<400> SEQUENCE: 18

Gln Asn Asp Gly Lys Glu Leu Cys Pro Pro Gly Lys Pro Thr Thr Ser
1               5                   10                  15

Glu Lys Ile His Glu Arg
            20

<210> SEQ ID NO 19
<211> LENGTH: 22
<212> TYPE: PRT
<213> ORGANISM: Artificial sequence
<220> FEATURE:
<223> OTHER INFORMATION: SSX-2 peptide

<400> SEQUENCE: 19

Pro Thr Thr Ser Glu Lys Ile His Glu Arg Ser Gly Pro Lys Arg Gly
1               5                   10                  15

```
Glu His Ala Trp Thr His
            20

<210> SEQ ID NO 20
<211> LENGTH: 22
<212> TYPE: PRT
<213> ORGANISM: Artificial sequence
<220> FEATURE:
<223> OTHER INFORMATION: SSX-2 peptide

<400> SEQUENCE: 20

Pro Lys Arg Gly Glu His Ala Trp Thr His Arg Leu Arg Glu Arg Lys
1               5                   10                  15

Gln Leu Val Ile Tyr Glu
            20

<210> SEQ ID NO 21
<211> LENGTH: 20
<212> TYPE: PRT
<213> ORGANISM: Artificial sequence
<220> FEATURE:
<223> OTHER INFORMATION: SSX-2 peptide

<400> SEQUENCE: 21

Arg Glu Arg Lys Gln Leu Val Ile Tyr Glu Glu Ile Ser Asp Pro Glu
1               5                   10                  15

Glu Asp Asp Glu
            20

<210> SEQ ID NO 22
<211> LENGTH: 20
<212> TYPE: PRT
<213> ORGANISM: Artificial sequence
<220> FEATURE:
<223> OTHER INFORMATION: SSX-2 peptide

<400> SEQUENCE: 22

Lys Met Lys Ala Ser Glu Lys Ile Phe Tyr Val Tyr Met Lys Arg Lys
1               5                   10                  15

Tyr Glu Ala Met
            20

<210> SEQ ID NO 23
<211> LENGTH: 18
<212> TYPE: PRT
<213> ORGANISM: Artificial sequence
<220> FEATURE:
<223> OTHER INFORMATION: SSX-2 peptide

<400> SEQUENCE: 23

Lys Ala Ser Glu Lys Ile Phe Tyr Val Tyr Met Lys Arg Lys Tyr Glu
1               5                   10                  15

Ala Met

<210> SEQ ID NO 24
<211> LENGTH: 16
<212> TYPE: PRT
<213> ORGANISM: Artificial sequence
<220> FEATURE:
<223> OTHER INFORMATION: SSX-2 peptide

<400> SEQUENCE: 24

Ser Glu Lys Ile Phe Tyr Val Tyr Met Lys Arg Lys Tyr Glu Ala Met
1               5                   10                  15
```

```
<210> SEQ ID NO 25
<211> LENGTH: 14
<212> TYPE: PRT
<213> ORGANISM: Artificial sequence
<220> FEATURE:
<223> OTHER INFORMATION: SSX-2 peptide

<400> SEQUENCE: 25

Lys Ile Phe Tyr Val Tyr Met Lys Arg Lys Tyr Glu Ala Met
1               5                   10

<210> SEQ ID NO 26
<211> LENGTH: 12
<212> TYPE: PRT
<213> ORGANISM: Artificial sequence
<220> FEATURE:
<223> OTHER INFORMATION: SSX-2 peptide

<400> SEQUENCE: 26

Phe Tyr Val Tyr Met Lys Arg Lys Tyr Glu Ala Met
1               5                   10

<210> SEQ ID NO 27
<211> LENGTH: 10
<212> TYPE: PRT
<213> ORGANISM: Artificial sequence
<220> FEATURE:
<223> OTHER INFORMATION: SSX-2 peptide

<400> SEQUENCE: 27

Val Tyr Met Lys Arg Lys Tyr Glu Ala Met
1               5                   10

<210> SEQ ID NO 28
<211> LENGTH: 20
<212> TYPE: PRT
<213> ORGANISM: Artificial sequence
<220> FEATURE:
<223> OTHER INFORMATION: SSX-2 peptide

<400> SEQUENCE: 28

Trp Glu Lys Met Lys Ala Ser Glu Lys Ile Phe Tyr Val Tyr Met Lys
1               5                   10                  15

Arg Lys Tyr Glu
            20

<210> SEQ ID NO 29
<211> LENGTH: 18
<212> TYPE: PRT
<213> ORGANISM: Artificial sequence
<220> FEATURE:
<223> OTHER INFORMATION: SSX-2 peptide

<400> SEQUENCE: 29

Trp Glu Lys Met Lys Ala Ser Glu Lys Ile Phe Tyr Val Tyr Met Lys
1               5                   10                  15

Arg Lys

<210> SEQ ID NO 30
<211> LENGTH: 16
<212> TYPE: PRT
<213> ORGANISM: Artificial sequence
<220> FEATURE:
<223> OTHER INFORMATION: SSX-2 peptide

<400> SEQUENCE: 30

Trp Glu Lys Met Lys Ala Ser Glu Lys Ile Phe Tyr Val Tyr Met Lys
```

<210> SEQ ID NO 31
<211> LENGTH: 14
<212> TYPE: PRT
<213> ORGANISM: Artificial sequence
<220> FEATURE:
<223> OTHER INFORMATION: SSX-2 peptide

<400> SEQUENCE: 31

Trp Glu Lys Met Lys Ala Ser Glu Lys Ile Phe Tyr Val Tyr
1               5                   10

<210> SEQ ID NO 32
<211> LENGTH: 14
<212> TYPE: PRT
<213> ORGANISM: Artificial sequence
<220> FEATURE:
<223> OTHER INFORMATION: SSX-2 peptide

<400> SEQUENCE: 32

Lys Ile Ile Tyr Val Tyr Met Lys Arg Lys Tyr Glu Ala Met
1               5                   10

<210> SEQ ID NO 33
<211> LENGTH: 14
<212> TYPE: PRT
<213> ORGANISM: Artificial sequence
<220> FEATURE:
<223> OTHER INFORMATION: SSX-2 peptide

<400> SEQUENCE: 33

Lys Ile Ser Tyr Val Tyr Met Lys Arg Lys Tyr Glu Ala Met
1               5                   10

<210> SEQ ID NO 34
<211> LENGTH: 14
<212> TYPE: PRT
<213> ORGANISM: Artificial sequence
<220> FEATURE:
<223> OTHER INFORMATION: SSX-2 peptide

<400> SEQUENCE: 34

Lys Ile Val Tyr Val Tyr Met Lys Arg Lys Tyr Glu Ala Met
1               5                   10

<210> SEQ ID NO 35
<211> LENGTH: 14
<212> TYPE: PRT
<213> ORGANISM: Artificial sequence
<220> FEATURE:
<223> OTHER INFORMATION: SSX-2 peptide

<400> SEQUENCE: 35

Lys Ile Ser Tyr Val Tyr Met Lys Arg Asn Tyr Glu Ala Met
1               5                   10

<210> SEQ ID NO 36
<211> LENGTH: 14
<212> TYPE: PRT
<213> ORGANISM: Artificial sequence
<220> FEATURE:
<223> OTHER INFORMATION: SSX-2 peptide

<400> SEQUENCE: 36

Lys Ile Ser Tyr Val Tyr Met Lys Arg Asn Tyr Lys Ala Met
1               5                   10

<210> SEQ ID NO 37
<211> LENGTH: 14
<212> TYPE: PRT
<213> ORGANISM: Artificial sequence
<220> FEATURE:
<223> OTHER INFORMATION: SSX-2 peptide

<400> SEQUENCE: 37

Lys Ile Ser Cys Val His Met Lys Arg Lys Tyr Glu Ala Met
1               5                   10

<210> SEQ ID NO 38
<211> LENGTH: 14
<212> TYPE: PRT
<213> ORGANISM: Artificial sequence
<220> FEATURE:
<223> OTHER INFORMATION: SSX-2 peptide

<400> SEQUENCE: 38

Lys Ile Val Tyr Val Tyr Met Lys Leu Asn Tyr Glu Val Met
1               5                   10

<210> SEQ ID NO 39
<211> LENGTH: 15
<212> TYPE: PRT
<213> ORGANISM: Artificial sequence
<220> FEATURE:
<223> OTHER INFORMATION: SSX-2 peptide

<400> SEQUENCE: 39

Lys Leu Gly Phe Lys Ala Thr Leu Pro Pro Phe Met Cys Asn Lys
1               5                   10                  15

<210> SEQ ID NO 40
<211> LENGTH: 15
<212> TYPE: PRT
<213> ORGANISM: Artificial sequence
<220> FEATURE:
<223> OTHER INFORMATION: SSX-2 peptide

<400> SEQUENCE: 40

Gln Met Thr Phe Gly Arg Leu Gln Gly Ile Ser Pro Lys Ile Met
1               5                   10                  15

<210> SEQ ID NO 41
<211> LENGTH: 15
<212> TYPE: PRT
<213> ORGANISM: Artificial sequence
<220> FEATURE:
<223> OTHER INFORMATION: SSX-2 peptide

<400> SEQUENCE: 41

Arg Lys Gln Leu Val Ile Tyr Glu Glu Ile Ser Asp Pro Glu Glu
1               5                   10                  15

<210> SEQ ID NO 42
<211> LENGTH: 15
<212> TYPE: PRT
<213> ORGANISM: Artificial sequence
<220> FEATURE:
<223> OTHER INFORMATION: SSX-2 peptide

<400> SEQUENCE: 42

Lys Ile Phe Tyr Val Tyr Met Lys Arg Lys Tyr Glu Ala Met Thr
1               5                   10                  15

<210> SEQ ID NO 43

-continued

```
<211> LENGTH: 15
<212> TYPE: PRT
<213> ORGANISM: Artificial sequence
<220> FEATURE:
<223> OTHER INFORMATION: SSX-2 peptide

<400> SEQUENCE: 43

Phe Gly Arg Leu Gln Gly Ile Ser Pro Lys Ile Met Pro Lys Lys
1               5                   10                  15

<210> SEQ ID NO 44
<211> LENGTH: 9
<212> TYPE: PRT
<213> ORGANISM: Artificial sequence
<220> FEATURE:
<223> OTHER INFORMATION: SSX-2 peptide

<400> SEQUENCE: 44

Tyr Ala Phe Arg Ala Ser Ala Lys Ala
1               5

<210> SEQ ID NO 45
<211> LENGTH: 15
<212> TYPE: PRT
<213> ORGANISM: Homo sapiens

<400> SEQUENCE: 45

Pro Leu Lys Met Leu Asn Ile Pro Ser Ile Asn Val His His Tyr
1               5                   10                  15

<210> SEQ ID NO 46
<211> LENGTH: 42
<212> TYPE: DNA
<213> ORGANISM: Artificial sequence
<220> FEATURE:
<223> OTHER INFORMATION: SSX-2 peptide

<400> SEQUENCE: 46
aaaatcttct atgtgtatat gaagagaaag tatgaggcta tg                          42

<210> SEQ ID NO 47
<211> LENGTH: 45
<212> TYPE: DNA
<213> ORGANISM: Artificial sequence
<220> FEATURE:
<223> OTHER INFORMATION: SSX-2 peptide

<400> SEQUENCE: 47
aaaatcttct atgtgtatat gaagagaaag tatgaggcta tgact                       45

<210> SEQ ID NO 48
<211> LENGTH: 66
<212> TYPE: DNA
<213> ORGANISM: Artificial sequence
<220> FEATURE:
<223> OTHER INFORMATION: SSX-2 peptide

<400> SEQUENCE: 48
tgggaaaaga tgaaagcctc ggagaaaatc ttctatgtgt atatgaagag aaagtatgag       60
gctatg                                                                 66

<210> SEQ ID NO 49
<211> LENGTH: 60
<212> TYPE: DNA
<213> ORGANISM: Artificial sequence
<220> FEATURE:
<223> OTHER INFORMATION: SSX-2 peptide
```

<210> SEQ ID NO 49
<211> LENGTH: 60
<212> TYPE: DNA
<213> ORGANISM: Artificial sequence
<220> FEATURE:
<223> OTHER INFORMATION: SSX-2 peptide

<400> SEQUENCE: 49
aagatgaaag cctcggagaa aatcttctat gtgtatatga agagaaagta tgaggctatg    60

<210> SEQ ID NO 50
<211> LENGTH: 54
<212> TYPE: DNA
<213> ORGANISM: Artificial sequence
<220> FEATURE:
<223> OTHER INFORMATION: SSX-2 peptide

<400> SEQUENCE: 50
aaagcctcgg agaaaatctt ctatgtgtat atgaagagaa agtatgaggc tatg    54

<210> SEQ ID NO 51
<211> LENGTH: 48
<212> TYPE: DNA
<213> ORGANISM: Artificial sequence
<220> FEATURE:
<223> OTHER INFORMATION: SSX-2 peptide

<400> SEQUENCE: 51
tcggagaaaa tcttctatgt gtatatgaag agaaagtatg aggctatg    48

<210> SEQ ID NO 52
<211> LENGTH: 15
<212> TYPE: PRT
<213> ORGANISM: Artificial sequence
<220> FEATURE:
<223> OTHER INFORMATION: SSX-2 peptide

<400> SEQUENCE: 52

Trp Glu Lys Met Lys Ala Ser Glu Lys Ile Phe Tyr Val Tyr Met
1               5                   10                  15

<210> SEQ ID NO 53
<211> LENGTH: 15
<212> TYPE: PRT
<213> ORGANISM: Artificial sequence
<220> FEATURE:
<223> OTHER INFORMATION: SSX-2 peptide

<400> SEQUENCE: 53

Glu Lys Ile Phe Tyr Val Tyr Met Lys Arg Lys Tyr Glu Ala Met
1               5                   10                  15

<210> SEQ ID NO 54
<211> LENGTH: 12
<212> TYPE: PRT
<213> ORGANISM: Artificial sequence
<220> FEATURE:
<223> OTHER INFORMATION: SSX-2 peptide

<400> SEQUENCE: 54

Trp Glu Lys Met Lys Ala Ser Glu Lys Ile Phe Tyr
1               5                   10

<210> SEQ ID NO 55
<211> LENGTH: 10
<212> TYPE: PRT
<213> ORGANISM: Artificial sequence
<220> FEATURE:
<223> OTHER INFORMATION: SSX-2 peptide

<400> SEQUENCE: 55

Trp Glu Lys Met Lys Ala Ser Glu Lys Ile
1               5                   10

<210> SEQ ID NO 56
<211> LENGTH: 21
<212> TYPE: PRT
<213> ORGANISM: Artificial sequence
<220> FEATURE:
<223> OTHER INFORMATION: SSX-2 peptide

<400> SEQUENCE: 56

Trp Glu Lys Met Lys Ala Ser Glu Lys Ile Phe Tyr Val Tyr Met Lys
1               5                   10                  15

Arg Lys Tyr Glu Ala
            20

<210> SEQ ID NO 57
<211> LENGTH: 19
<212> TYPE: PRT
<213> ORGANISM: Artificial sequence
<220> FEATURE:
<223> OTHER INFORMATION: SSX-2 peptide

<400> SEQUENCE: 57

Trp Glu Lys Met Lys Ala Ser Glu Lys Ile Phe Tyr Val Tyr Met Lys
1               5                   10                  15

Arg Lys Tyr

<210> SEQ ID NO 58
<211> LENGTH: 17
<212> TYPE: PRT
<213> ORGANISM: Artificial sequence
<220> FEATURE:
<223> OTHER INFORMATION: SSX-2 peptide

<400> SEQUENCE: 58

Trp Glu Lys Met Lys Ala Ser Glu Lys Ile Phe Tyr Val Tyr Met Lys
1               5                   10                  15

Arg

<210> SEQ ID NO 59
<211> LENGTH: 15
<212> TYPE: PRT
<213> ORGANISM: Artificial sequence
<220> FEATURE:
<223> OTHER INFORMATION: SSX-2 peptide

<400> SEQUENCE: 59

Trp Glu Lys Met Lys Ala Ser Glu Lys Ile Phe Tyr Val Tyr Met
1               5                   10                  15

<210> SEQ ID NO 60
<211> LENGTH: 13
<212> TYPE: PRT
<213> ORGANISM: Artificial sequence
<220> FEATURE:
<223> OTHER INFORMATION: SSX-2 peptide

<400> SEQUENCE: 60

Trp Glu Lys Met Lys Ala Ser Glu Lys Ile Phe Tyr Val
1               5                   10

<210> SEQ ID NO 61
<211> LENGTH: 20
<212> TYPE: PRT
<213> ORGANISM: Artificial sequence
<220> FEATURE:
<223> OTHER INFORMATION: SSX-2 peptide

<400> SEQUENCE: 61

Glu Lys Met Lys Ala Ser Glu Lys Ile Phe Tyr Val Tyr Met Lys Arg
1               5                   10                  15

Lys Tyr Glu Ala
            20

<210> SEQ ID NO 62
<211> LENGTH: 18
<212> TYPE: PRT
<213> ORGANISM: Artificial sequence
<220> FEATURE:
<223> OTHER INFORMATION: SSX-2 peptide

<400> SEQUENCE: 62

Glu Lys Met Lys Ala Ser Glu Lys Ile Phe Tyr Val Tyr Met Lys Arg
1               5                   10                  15

Lys Tyr

<210> SEQ ID NO 63
<211> LENGTH: 16
<212> TYPE: PRT
<213> ORGANISM: Artificial sequence
<220> FEATURE:
<223> OTHER INFORMATION: SSX-2 peptide

<400> SEQUENCE: 63

Glu Lys Met Lys Ala Ser Glu Lys Ile Phe Tyr Val Tyr Met Lys Arg
1               5                   10                  15

<210> SEQ ID NO 64
<211> LENGTH: 14
<212> TYPE: PRT
<213> ORGANISM: Artificial sequence
<220> FEATURE:
<223> OTHER INFORMATION: SSX-2 peptide

<400> SEQUENCE: 64

Glu Lys Met Lys Ala Ser Glu Lys Ile Phe Tyr Val Tyr Met
1               5                   10

<210> SEQ ID NO 65
<211> LENGTH: 12
<212> TYPE: PRT
<213> ORGANISM: Artificial sequence
<220> FEATURE:
<223> OTHER INFORMATION: SSX-2 peptide

<400> SEQUENCE: 65

Glu Lys Met Lys Ala Ser Glu Lys Ile Phe Tyr Val
1               5                   10

<210> SEQ ID NO 66
<211> LENGTH: 19
<212> TYPE: PRT
<213> ORGANISM: Artificial sequence
<220> FEATURE:
<223> OTHER INFORMATION: SSX-2 peptide

<400> SEQUENCE: 66

Lys Met Lys Ala Ser Glu Lys Ile Phe Tyr Val Tyr Met Lys Arg Lys
1               5                   10                  15

Tyr Glu Ala

<210> SEQ ID NO 67

```
<211> LENGTH: 17
<212> TYPE: PRT
<213> ORGANISM: Artificial sequence
<220> FEATURE:
<223> OTHER INFORMATION: SSX-2 peptide

<400> SEQUENCE: 67

Lys Met Lys Ala Ser Glu Lys Ile Phe Tyr Val Tyr Met Lys Arg Lys
1               5                   10                  15

Tyr

<210> SEQ ID NO 68
<211> LENGTH: 16
<212> TYPE: PRT
<213> ORGANISM: Artificial sequence
<220> FEATURE:
<223> OTHER INFORMATION: SSX-2 peptide

<400> SEQUENCE: 68

Glu Lys Met Lys Ala Ser Glu Lys Ile Phe Tyr Val Tyr Met Lys Arg
1               5                   10                  15

<210> SEQ ID NO 69
<211> LENGTH: 14
<212> TYPE: PRT
<213> ORGANISM: Artificial sequence
<220> FEATURE:
<223> OTHER INFORMATION: SSX-2 peptide

<400> SEQUENCE: 69

Glu Lys Met Lys Ala Ser Glu Lys Ile Phe Tyr Val Tyr Met
1               5                   10

<210> SEQ ID NO 70
<211> LENGTH: 11
<212> TYPE: PRT
<213> ORGANISM: Artificial sequence
<220> FEATURE:
<223> OTHER INFORMATION: SSX-2 peptide

<400> SEQUENCE: 70

Lys Met Lys Ala Ser Glu Lys Ile Phe Tyr Val
1               5                   10

<210> SEQ ID NO 71
<211> LENGTH: 19
<212> TYPE: PRT
<213> ORGANISM: Artificial sequence
<220> FEATURE:
<223> OTHER INFORMATION: SSX-2 peptide

<400> SEQUENCE: 71

Glu Lys Met Lys Ala Ser Glu Lys Ile Phe Tyr Val Tyr Met Lys Arg
1               5                   10                  15

Lys Tyr Glu

<210> SEQ ID NO 72
<211> LENGTH: 17
<212> TYPE: PRT
<213> ORGANISM: Artificial sequence
<220> FEATURE:
<223> OTHER INFORMATION: SSX-2 peptide

<400> SEQUENCE: 72

Glu Lys Met Lys Ala Ser Glu Lys Ile Phe Tyr Val Tyr Met Lys Arg
1               5                   10                  15
```

Lys

```
<210> SEQ ID NO 73
<211> LENGTH: 15
<212> TYPE: PRT
<213> ORGANISM: Artificial sequence
<220> FEATURE:
<223> OTHER INFORMATION: SSX-2 peptide

<400> SEQUENCE: 73

Glu Lys Met Lys Ala Ser Glu Lys Ile Phe Tyr Val Tyr Met Lys
1               5                   10                  15

<210> SEQ ID NO 74
<211> LENGTH: 13
<212> TYPE: PRT
<213> ORGANISM: Artificial sequence
<220> FEATURE:
<223> OTHER INFORMATION: SSX-2 peptide

<400> SEQUENCE: 74

Glu Lys Met Lys Ala Ser Glu Lys Ile Phe Tyr Val Tyr
1               5                   10

<210> SEQ ID NO 75
<211> LENGTH: 11
<212> TYPE: PRT
<213> ORGANISM: Artificial sequence
<220> FEATURE:
<223> OTHER INFORMATION: SSX-2 peptide

<400> SEQUENCE: 75

Glu Lys Met Lys Ala Ser Glu Lys Ile Phe Tyr
1               5                   10

<210> SEQ ID NO 76
<211> LENGTH: 18
<212> TYPE: PRT
<213> ORGANISM: Artificial sequence
<220> FEATURE:
<223> OTHER INFORMATION: SSX-2 peptide

<400> SEQUENCE: 76

Lys Met Lys Ala Ser Glu Lys Ile Phe Tyr Val Tyr Met Lys Arg Lys
1               5                   10                  15

Tyr Glu

<210> SEQ ID NO 77
<211> LENGTH: 16
<212> TYPE: PRT
<213> ORGANISM: Artificial sequence
<220> FEATURE:
<223> OTHER INFORMATION: SSX-2 peptide

<400> SEQUENCE: 77

Lys Met Lys Ala Ser Glu Lys Ile Phe Tyr Val Tyr Met Lys Arg Lys
1               5                   10                  15

<210> SEQ ID NO 78
<211> LENGTH: 15
<212> TYPE: PRT
<213> ORGANISM: Artificial sequence
<220> FEATURE:
<223> OTHER INFORMATION: SSX-2 peptide

<400> SEQUENCE: 78

Glu Lys Met Lys Ala Ser Glu Lys Ile Phe Tyr Val Tyr Met Lys
```

```
<210> SEQ ID NO 79
<211> LENGTH: 13
<212> TYPE: PRT
<213> ORGANISM: Artificial sequence
<220> FEATURE:
<223> OTHER INFORMATION: SSX-2 peptide

<400> SEQUENCE: 79

Glu Lys Met Lys Ala Ser Glu Lys Ile Phe Tyr Val Tyr
1               5                   10

<210> SEQ ID NO 80
<211> LENGTH: 10
<212> TYPE: PRT
<213> ORGANISM: Artificial sequence
<220> FEATURE:
<223> OTHER INFORMATION: SSX-2 peptide

<400> SEQUENCE: 80

Lys Met Lys Ala Ser Glu Lys Ile Phe Tyr
1               5                   10

<210> SEQ ID NO 81
<211> LENGTH: 15
<212> TYPE: PRT
<213> ORGANISM: Artificial sequence
<220> FEATURE:
<223> OTHER INFORMATION: SSX-2 peptide

<400> SEQUENCE: 81

Lys Glu Glu Trp Glu Lys Met Lys Ala Ser Glu Lys Ile Phe Tyr
1               5                   10                  15

<210> SEQ ID NO 82
<211> LENGTH: 15
<212> TYPE: PRT
<213> ORGANISM: Artificial sequence
<220> FEATURE:
<223> OTHER INFORMATION: SSX-2 peptide

<400> SEQUENCE: 82

Val Tyr Met Lys Arg Lys Tyr Glu Ala Met Thr Lys Leu Gly Phe
1               5                   10                  15

<210> SEQ ID NO 83
<211> LENGTH: 15
<212> TYPE: PRT
<213> ORGANISM: Artificial sequence
<220> FEATURE:
<223> OTHER INFORMATION: SSX-1 peptide (37-51)

<400> SEQUENCE: 83

Trp Lys Lys Met Lys Tyr Ser Glu Lys Ile Ser Tyr Val Tyr Met
1               5                   10                  15

<210> SEQ ID NO 84
<211> LENGTH: 15
<212> TYPE: PRT
<213> ORGANISM: Artificial sequence
<220> FEATURE:
<223> OTHER INFORMATION: SSX-3 peptide (37-51)

<400> SEQUENCE: 84

Trp Glu Lys Met Lys Val Ser Glu Lys Ile Val Tyr Val Tyr Met
1               5                   10                  15
```

```
<210> SEQ ID NO 85
<211> LENGTH: 15
<212> TYPE: PRT
<213> ORGANISM: Artificial sequence
<220> FEATURE:
<223> OTHER INFORMATION: SSX-4 peptide (37-51)

<400> SEQUENCE: 85

Trp Glu Lys Met Lys Ser Ser Glu Lys Ile Val Tyr Val Tyr Met
1               5                   10                  15

<210> SEQ ID NO 86
<211> LENGTH: 15
<212> TYPE: PRT
<213> ORGANISM: Artificial sequence
<220> FEATURE:
<223> OTHER INFORMATION: SSX-5 peptide (37-51)

<400> SEQUENCE: 86

Trp Glu Lys Met Lys Ala Ser Glu Lys Ile Phe Ile Val Tyr Met
1               5                   10                  15
```